(12) United States Patent
Palacios et al.

(10) Patent No.: US 12,000,773 B2
(45) Date of Patent: Jun. 4, 2024

(54) SYSTEMS AND METHODS FOR SCREENING NUTRIENTS OR CHEMICAL COMPOSITIONS USING DIVERSIFIERS FOR NOISE REDUCTION

(71) Applicant: Hyperspectral Corp., Alexandria, VA (US)

(72) Inventors: David M. Palacios, Pasadena, CA (US); Harry Hopper, Alexandria, VA (US)

(73) Assignee: Hyperspectral Corp., Alexlandria, VA (US)

( * ) Notice: Subject to any disclaimer, the term of this patent is extended or adjusted under 35 U.S.C. 154(b) by 274 days.

(21) Appl. No.: 17/645,450

(22) Filed: Dec. 21, 2021

(65) Prior Publication Data

US 2023/0121237 A1 Apr. 20, 2023

Related U.S. Application Data

(60) Provisional application No. 63/255,774, filed on Oct. 14, 2021.

(51) Int. Cl.
| | |
|---|---|
| *G01N 21/25* | (2006.01) |
| *G01N 15/06* | (2006.01) |
| *G01N 15/075* | (2024.01) |
| *G01N 21/31* | (2006.01) |
| *G01N 21/39* | (2006.01) |
| *G01N 21/51* | (2006.01) |

(Continued)

(52) U.S. Cl.
CPC ....... *G01N 21/255* (2013.01); *G01N 15/0606* (2013.01); *G01N 21/314* (2013.01); *G01N 21/39* (2013.01); *G06N 20/00* (2019.01); *G01N 15/075* (2024.01); *G01N 2021/513* (2013.01); *G01N 33/569* (2013.01)

(58) Field of Classification Search
CPC ............ G01N 15/0606; G01N 15/075; G01N 21/255; G01N 21/314; G01N 21/39; G01N 33/569; G01N 2021/513; G06N 20/00
See application file for complete search history.

(56) References Cited

U.S. PATENT DOCUMENTS

| | | | |
|---|---|---|---|
| 7,652,765 B1 * | 1/2010 | Geshwind | G01J 3/2823 356/330 |
| 8,277,384 B2 * | 10/2012 | Fine | A61B 5/0261 600/502 |
| 11,448,598 B1 * | 9/2022 | Bhartia | G01N 21/359 |

(Continued)

*Primary Examiner* — Blake C Riddick
(74) *Attorney, Agent, or Firm* — Ahmann Kloke LLP

(57) ABSTRACT

A system comprising at least one light source configured to generate a light at specific wavelengths and project the light over an optical path, a sample device, the sample device configured to receive a sample obtained from a person, the sample device being transparent and being at least partially within the optical path, a diversifier including occlusions for scattering coherent light received from the light source along the optical path, a first detector configured to receive the light over the optical path and from at least a portion of the diversifier, the detector configured to detect spectral intensities of the light, and a second detector configured to receive at least a portion of the light form the optical path before the light passes through the diffuser, the second detector configured to detect spectral intensities of the light.

18 Claims, 53 Drawing Sheets

(51) Int. Cl.
*G01N 33/569* (2006.01)
*G06N 20/00* (2019.01)

(56) References Cited

U.S. PATENT DOCUMENTS

| | | | |
|---|---|---|---|
| 2005/0270528 A1* | 12/2005 | Geshwind | G06V 20/13 |
| | | | 356/330 |
| 2006/0009685 A1* | 1/2006 | Finarov | A61B 5/6838 |
| | | | 600/344 |
| 2006/0013454 A1* | 1/2006 | Flewelling | G06T 11/00 |
| | | | 382/128 |
| 2008/0180664 A1* | 7/2008 | Backman | G01N 21/49 |
| | | | 356/317 |
| 2009/0103852 A1* | 4/2009 | Hamamoto | A61B 5/097 |
| | | | 385/12 |
| 2011/0270113 A1* | 11/2011 | Heyne | G01N 21/39 |
| | | | 250/343 |
| 2015/0238135 A1* | 8/2015 | Bambot | G01N 21/474 |
| | | | 600/407 |
| 2015/0285685 A1* | 10/2015 | Wax | G01B 9/02091 |
| | | | 356/456 |
| 2016/0377596 A1* | 12/2016 | Kusaba | G01N 21/3504 |
| | | | 600/532 |
| 2017/0045441 A1* | 2/2017 | Nciri | G01J 3/4406 |
| 2017/0319073 A1* | 11/2017 | DiMaio | A61B 5/0075 |
| 2018/0067036 A1* | 3/2018 | Swartzlander, Jr. | |
| | | | G01N 15/0211 |
| 2018/0085003 A1* | 3/2018 | Goldring | A61B 5/746 |
| 2018/0348119 A1* | 12/2018 | Hwang | G01N 21/49 |
| 2019/0226984 A1* | 7/2019 | Lee | G01N 21/255 |
| 2020/0209060 A1* | 7/2020 | Rosen | G01J 3/0208 |
| 2020/0355605 A1* | 11/2020 | Causey, III | A61B 5/157 |
| 2021/0123858 A1* | 4/2021 | O'Rourke | G01N 21/39 |
| 2021/0208062 A1* | 7/2021 | Linden | G01N 33/497 |
| 2021/0310939 A1* | 10/2021 | Brauer | G01N 21/255 |
| 2023/0036551 A1* | 2/2023 | Sabry | G01J 3/0208 |

* cited by examiner

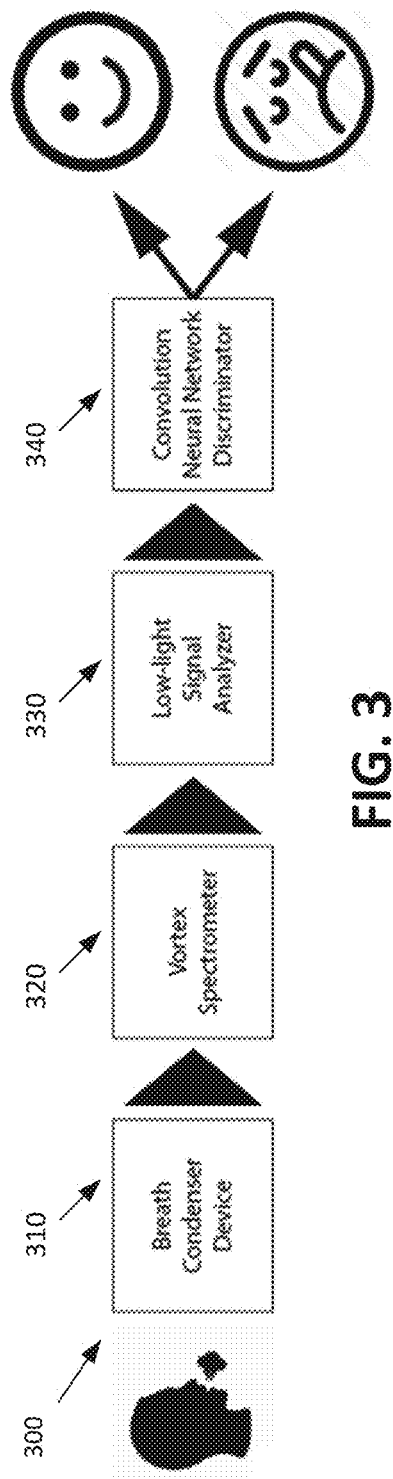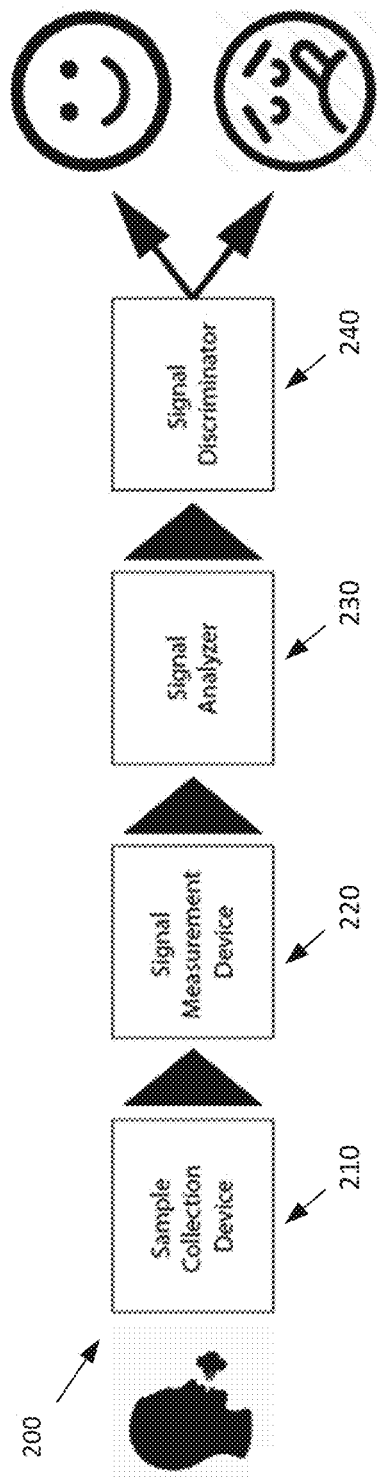

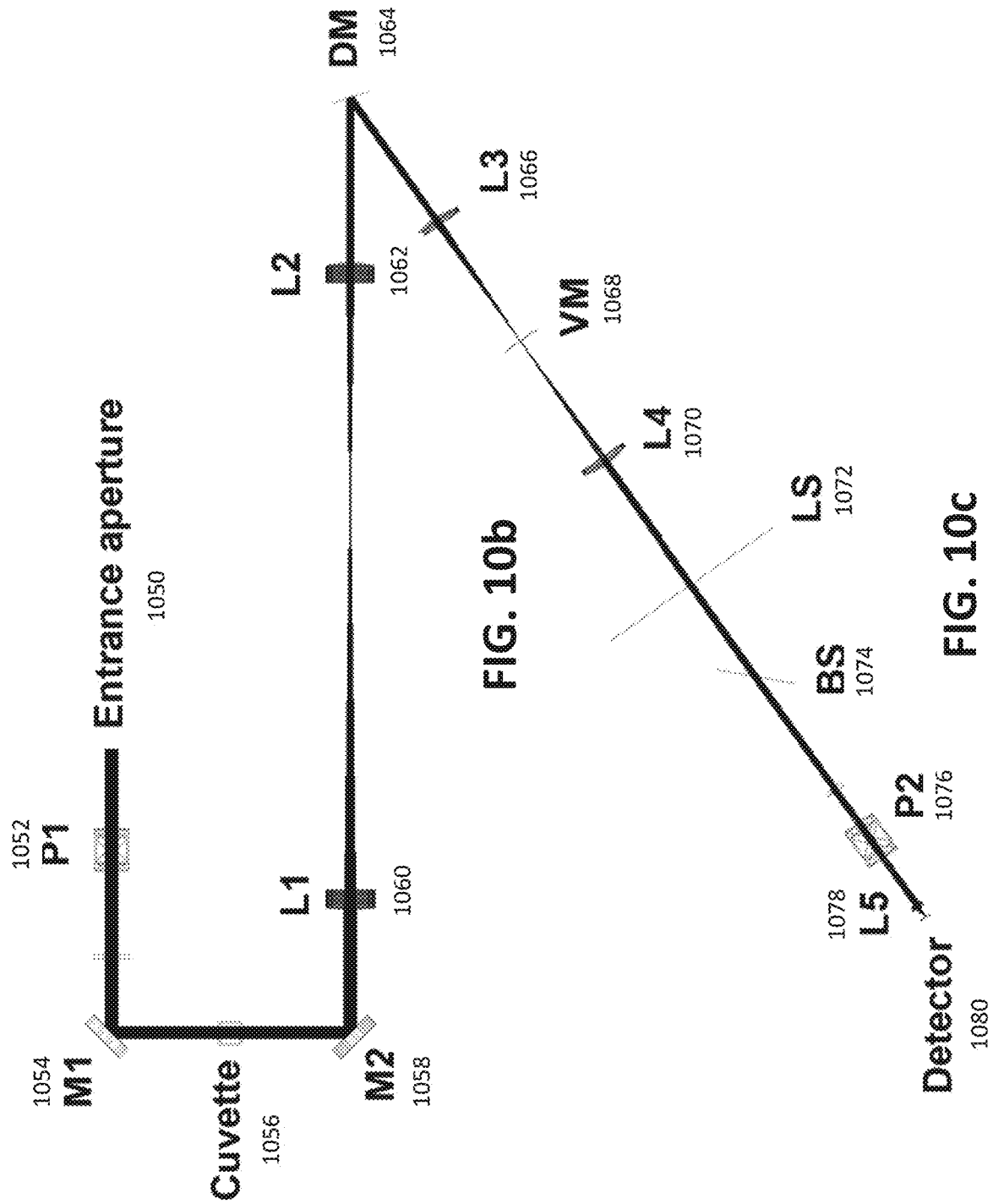

SYSTEMS AND METHODS FOR SCREENING NUTRIENTS OR CHEMICAL COMPOSITIONS USING DIVERSIFIERS FOR NOISE REDUCTION

CROSS-REFERENCE TO RELATED APPLICATIONS

This application claims priority to U.S. Provisional Patent Application No. 63/255,774, filed on Oct. 14, 2021 and entitled "SYSTEMS AND METHODS FOR SCREENING ASYMPTOMATIC VIRUS EMITTERS USING DIVERSIFIERS FOR NOISE REDUCTION", which is incorporated in its entirety herein by reference.

TECHNICAL FIELD

This disclosure pertains to secure systems for noninvasive health screening and, more specifically, a spectrometer with a vortex mask to improve signal detection of infection of noninvasively acquired samples.

BACKGROUND

During a pandemic and the aftermath, it is vital to identify infected people so that they can be effectively quarantined to reduce the spread of the virus. Multiple testing methods have been developed to diagnose viral infections, including polymerase chain reaction (PCR), enzyme-linked immunosorbent assay, immunofluorescent assay, and others. However, these methods are impractical when it comes to wide-scale screening because of lack of speed, lack of accuracy, lack of resources, and cost. As seen with the COVID-19 pandemic, when attempting to screen large populations, reagent supplies become depleted, and current testing methodologies take days to return a result back to a patient. Due to the limited supply of test equipment, testing is performed on people who actively present symptoms and self-identify. The testing is primarily used to verify the diagnosis.

Relying on a person to present symptoms is a significant challenge for containment because of the reliance on a person's immune system's response to the virus (such as running a fever or developing a persistent dry cough). In the case of COVID-19, infected people may be contagious but asymptomatic during the virus' long incubation period (e.g., 2-14 days). The long incubation period has made the virus nearly impossible to contain and has required governments to take strong action to reduce the spread. These strong actions include orders for long-term shelter-in-place and social distancing until a vaccine can be developed and deployed globally (12-18 months).

These problems can be common for many different pathogens. There are many bacterium and viruses, for example, that may be asymptomatic for a period of time but may have serious health consequences. Further, many bacterium and viruses may be highly infectious either before or after symptoms appear. Testing for any number of pathogens can be invasive, uncomfortable, and/or painful. In addition, many tests for a specific pathogen may be inaccurate or slow. Moreover, the potency or effectiveness of many compounds (e.g., reagents) used to test pathogens may change due to age, exposure to environmental conditions, and/or improper handling.

SUMMARY

An example system comprising at least one light source configured to generate a light of at least one wavelength and project the light over an optical path, a sample device, the device containing a sample obtained from exhalation of a person, the sample device being transparent and being at least partially within the optical path, a vortex mask being within the optical path and configured to receive the light after the light passes through at least a portion of the sample device, the vortex mask including a series of concentric circles etched in a substrate, the vortex mask configured to provide destructive interference of coherent light received from the at least one light source, a detector configured to detect and measure wavelength intensities from the light in the optical path, the wavelength intensities being impacted by the light passing through the sample, the detector receiving the light that remained after passing through the vortex mask, and a processor configured to provide measurement results based on the wavelength intensities.

In some embodiments, the system further comprises a discriminator configured to analyze the measurement results and identify a category associated with the measurement results. The discriminator may utilize logistic regression to categorize the measurement results.

The sample may be obtained from a breathalyzer provided to a person. In one example, the breathalyzer cools a cuvette which condenses the sample of an exhalation of the user within the sample device, the sample device being removable from the breathalyzer.

The system may further comprise a lyot mask (e.g., lyot stop) positioned in the optical path and configured to receive light from the vortex mask and provide the light towards the detector, the lyot mask configured to relocate residual light away from a region of the image plane, thereby reducing light noise from the at least one or more light sources and improving sensitivity to off-axis scattered light. The lyot mask may be, for example, a lyot-plane phase mask.

The vortex mask may be an optical vortex coronagraph that uses a phase-mask in which the phase-shift varies azimuthally around a center to mask out light along the center axis of the optical path of the spectrometer but allows light from off axis.

In various embodiments, the system comprises two light sources, each configured to provide a different wavelength. Alternately, the system may include a single light source that generates several wavelengths, the system further comprising a diffraction grating to separate out different wavelengths for propagating down the optical path.

In some embodiments, the at least one light source generates wavelengths at 735 nm, 780 nm, 810 nm, and 860 nm. The discriminator may assess features based on intensities of those wavelengths to make categories. In some embodiments, the sample may indicate infection by COVID-19.

An example method may comprise generating, by at least one light source, a light of at least one wavelength and project the light over an optical path, receiving, by a sample device, the light from the at least one optical source, the device containing a sample obtained from exhalation of a person, the sample device being transparent and being at least partially within the optical path, providing destructive interference of coherent light passed through the sample device using a vortex mask, the vortex mask including a series of concentric circles etched in a substrate, measuring, by a detector, wavelength intensities of the light after having passed through the vortex mask, and providing measurement results based on wavelength intensities.

BRIEF DESCRIPTION OF THE DRAWINGS

FIG. 2 is a generalized approach in some embodiments.

FIG. 3 is another example approach in some embodiments.

FIG. 10C is another example of an optical path of a spectrometer in some embodiments.

Figure 1:
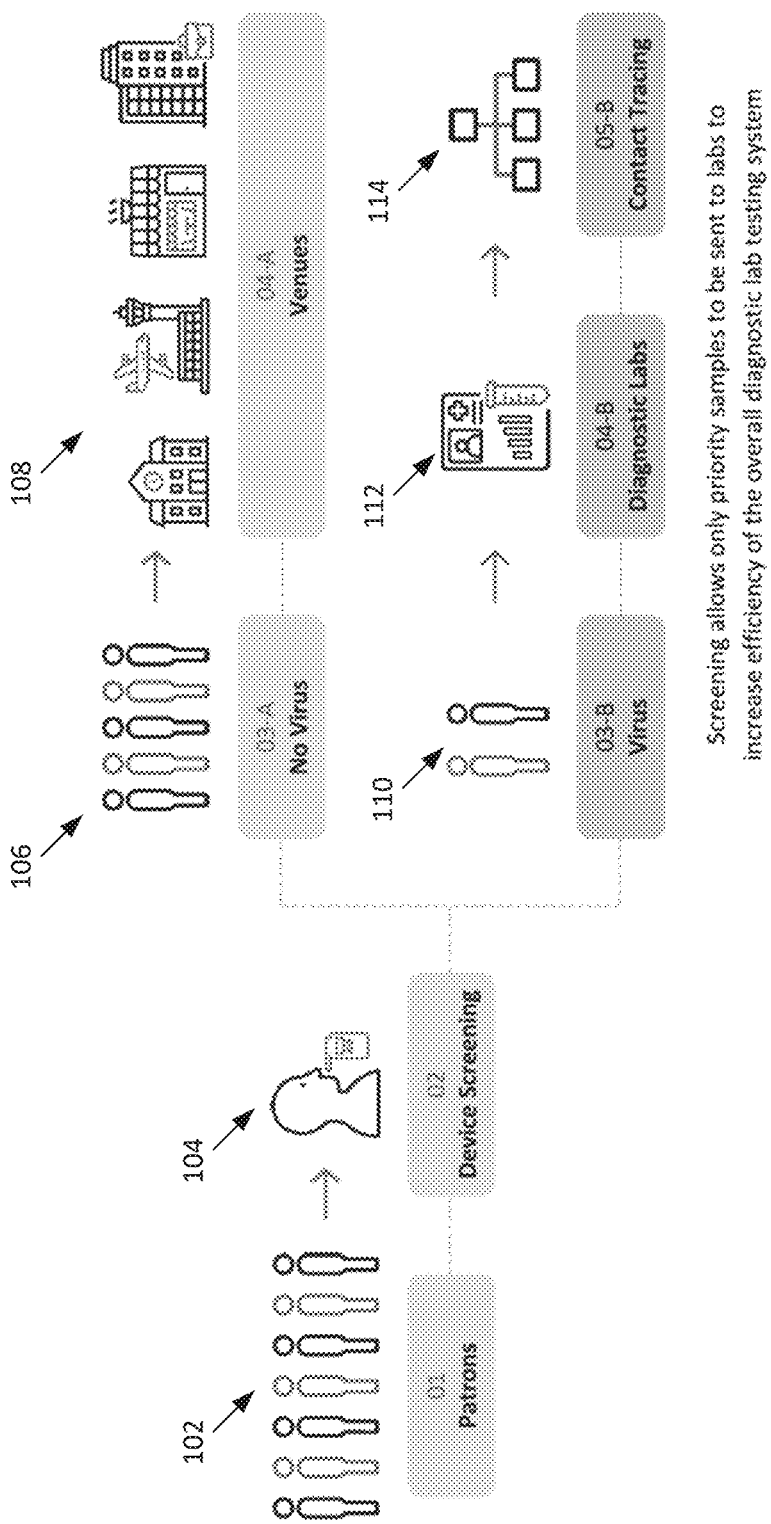
FIG. 1 depicts an environment for screening any number of patrons for infection in some embodiments.

The health screening device 104 may be non-invasive and requires no reagents. In various embodiments, the health screening device 104 or a system that assesses results from the health screening device 104, may return results within minutes or seconds. In one example, the health screening device 104 includes a deployable breathalyzer and spectrometer in communication with a discriminator (e.g., a cloud-based or local device) that determines the presence of infection. In other examples, the health screening device 104 includes a cuvette to collect a saliva sample or a device (e.g., fogging glass discussed herein) to receive a swab sample or saliva sample. The samples may be measured using a spectrometer as discussed herein and the results analyzed as also discussed herein. This system may allow for fast testing of large volumes of people with near real-time feedback on par with current airport security measures. The discriminator may be or include an artificial intelligence system (e.g., a convolutional neural network) or statistical classifier (e.g., a performing logistic regression).

In the example of environment 100, any number of patrons may be assessed at any number of locations. For example, patrons 102 may be screened prior to being allowed to enter to an office, place of employment, or venue 108. In another example, patrons 102 may be screened prior to being allowed to enter into any venue 108 such as an airport, plane, bus, bus terminal, train, train station, subway, subway station, retail store, restaurant, sports venue, concert venue, or the like. Because the health screening device 104 is noninvasive and may work quickly to detect infection, many geographically remote patrons may be effectively screened to enable them to engage in activities that may otherwise be unwise.

The results of the health screening device 104 may be assessed to determine if a patron is infected or not infected. Patrons that are determined not to be infected 106 may engage in activities that bring themselves into proximity with others (e.g., work, travel, entertainment, and the like). Patrons that are determined to be infected patrons 110, may be advised to maintain social distancing, receive treatment, and/or isolate themselves until they are no longer infected. Infected patrons 110 may be further tested by diagnostic labs 112 and/or be the subject of contact tracing 114 to identify other individuals that may be infected and may transmit the infection to others.

Due to the noninvasive nature and the speed of testing by the health screening device 104, infected patrons 110 may be repeatedly tested (e.g., every day), until it is determined that they have overcome the infection.

It will be appreciated with the increasing difficulty of obtaining traditional test kits (e.g., due to a limitation of the availability of certain reagents), health professionals may utilize the systems and methods described herein to determine infection and only use more traditional test kits on those with strong symptoms and/or those that are identified as being infected by the systems and methods described herein. Alternately, the systems and methods described herein may replace traditional testing.

FIG. 2 is a generalized approach 200 in some embodiments. Several examples include receiving a breath sample using a breath condenser device. While these examples and some figures depict collecting a breath sample, it will be appreciated that a patron's saliva or swab sample may be collected instead of a breath sample. Samples (e.g., breath, saliva, or swab) may be utilized with one or more of the systems and methods described herein.

In step 210, a sample collection device (e.g., health screening device 104) receives breath (e.g., an exhalation) from a patron. As discussed herein, a patron is a person. The patron may or may not be sick with a viral infection. The patron may or may not show symptoms of infection. The sample collection device may be any collection device configured to receive an exhalation (e.g., breath) of a patron. The sample collection device may include or be coupled to a spectrometer. The spectrometer may be configured to project different wavelengths through particles of the breath of the patron in order to generate spectral components that may be measured.

In some examples, the sample collection device may include a breath collection chamber and/or a substrate. The breath collection chamber and/or substrate may be transparent or semi-transparent member configured to collect particles from the breath of the patron. A spectrometer may project any number of wavelengths through the breath collection chamber and/or the substrate. The spectrometer may include or be coupled to a vortex mask in order to reduce or eliminate undesired wavelengths and/or wavelength intensities of the light that passed through the collection chamber and/or the substrate. The vortex mask may include or be an optical vortex coronagraph that uses a phase-mask in which the phase-shift varies azimuthally around the center. The vortex mask may use interference to mask out light along the center axis of the optical path of the spectrometer but allows light from off axis through. This enables scattered, incoherent light that interacted with components in the exhalation of the patron to pass through.

The signal measurement device 220 may be or include the spectrometer configured to receive the assess wavelength energy absorbed and transmitted through the breath sample. In one example, a spectrometer may receive and project light into a chamber through an entrance aperture. The entrance aperture may be a lit which may vignette the light. In various embodiments, the spectrometer may include a filter to limit bandwidth of light entering the chamber. The light may reflect from a collimating mirror as a collimated beam towards a diffraction grating which may split photons by wavelength through an optical path. The diffraction grating may project the separated light through an exit slit or filter to control which wavelength is projected through the sample. In another example, the diffraction grating may spread the light across a focusing mirror which directs light at each wavelength through the breath collection chamber or the substrate to the detector. Light strikes the individual pixels of the detector. The detector may detect the transmittance and/or absorbance of the breath sample (i.e., the intensity of light along any number of wavelengths absorbed or transmitted).

The signal analyzer 230 may receive measurements from the detector of the signal measurement device 220 and provide an analysis of the measurements. The signal analyzer 230 may assess the measurements to identify information of interest (e.g., intensity of light absorbed and/or transmitted at specific wavelengths) while ignoring or assessing information from other wavelengths. The presence of certain wavelengths of a certain intensity in addition to or without other wavelengths may indicate the presence of proteins associated with one or more viruses.

The signal discriminator 240 may receive the analysis of the signal analyzer 230 to provide a category or indication of the presence of infection. In one example, the signal discriminator 240 may indicate whether a patron is infected or not infected. In another example, the signal discriminator 240 may indicate whether a patron is likely infected or not likely infected. In some embodiments, the signal discriminator 240 may indicate whether the infection status of the patron is unknown (e.g., if the analysis and/or discrimination is uncertain).

The signal discriminator 240 may be or utilize a logistic regression analysis model, model fitting, thresholding, an AI model (e.g., a neural network), and/or the like. In some embodiments, the signal discriminator maybe or utilize statistical and/or mathematical models to provide categories.

FIG. 3 is another example approach 300 in some embodiments. A breath condenser device 310 (e.g., breathalyzer 400 discussed herein) receives breath from a patron. A breath condenser device 310 may be configured to receive a person's breath from over a spigot, straw, or some other orifice. The breath from the patron may be collected on a transparent or semitransparent substrate (e.g., the breath may condense on the substrate). The breath condenser device 310 may have a heat sink, fan, coolant, and/or other elements to assist in the condensation of the user's breath.

The breath condenser device 310 may be any collection device configured to receive the breath of a patron and perform analysis on components and/or particles contained in the breath of the patron. The breath condenser device may include or be coupled to a spectrometer. The spectrometer may be configured to project different wavelengths through particles of the breath of the patron in order to generate spectral components that may be measured.

In various embodiments, the breath condenser device 310 is replaced with a fogging window for the patron to breath on (e.g., exhale), a cuvette to receive the patron's saliva, or the like.

Measurements on the condensed substrate may be taken using a vortex spectrometer 320. A vortex spectrometer 320 is a spectrometer with a vortex mask. The spectrometer 320 may be any spectrometer configured to project light at one or more wavelengths through the breath sample to a detector to make measurements based on absorption and/or transmittance.

The vortex mask, further discussed herein, may be a grating of concentric circles configured to create destructive interference and eliminate undesired light. This effect amplifies the desired signal from the proteins and/or viruses contained within the breath sample. As a result, a signal that is typically too faint to detect and is otherwise blocked out by other signals (i.e., noise) becomes detectable.

The low-light signal analyzer 330 may be a signal measurement device and/or a signal analyzer configured to work in conjunction with the vortex mask to identify faint signals that are created or influenced by the presence of proteins and/or viruses in the breath samples. The low-light signal analyzer 330 may be or include the spectrometer configured to receive the assess wavelength energy absorbed and transmitted through the breath sample.

The low-light signal analyzer 330 assess the measurements to identify information of interest (e.g., intensity of light absorbed and/or transmitted at specific wavelengths) while ignoring or assessing information from other wavelengths. The presence of certain wavelengths of a certain intensity in addition to or without other wavelengths may indicate the presence of proteins associated with one or more viruses.

The convolutional neural network discriminator 340 may receive the analysis from the low-light signal analyzer 330 to provide a category or indication of the presence of infection. As discussed regarding FIG. 2, a signal discriminator may be any device or include any approach for assisting in categorizing infection. In this example, the signal discriminator is a convolutional neural network discriminator 340.

The convolutional neural network discriminator 340 may be trained based on at least a subset of measurements and analysis generated from any number of peoples' condensed breath and the known results (e.g., infection confirmed and/or lack of infection confirmed through lab testing or other means). Once trained, the convolutional neural network discriminator 340 may be tested against a subset of analysis and measurements of people to compare the prediction to known truth. The convolutional neural network discriminator 340 is further described herein.

In one example, the signal discriminator 240 may indicate whether a patron is infected or not infected. In another example, the signal discriminator 240 may indicate whether a patron is likely infected or not likely infected. In some embodiments, the signal discriminator 240 may indicate whether the infection status of the patron is unknown (e.g., if the analysis and/or discrimination is uncertain).

The signal discriminator 240 may be or utilize an AI model (e.g., a neural network) that is trained and curated. In some embodiments, the signal discriminator maybe or utilize statistical and/or mathematical models to provide categories.

Figure 4A:
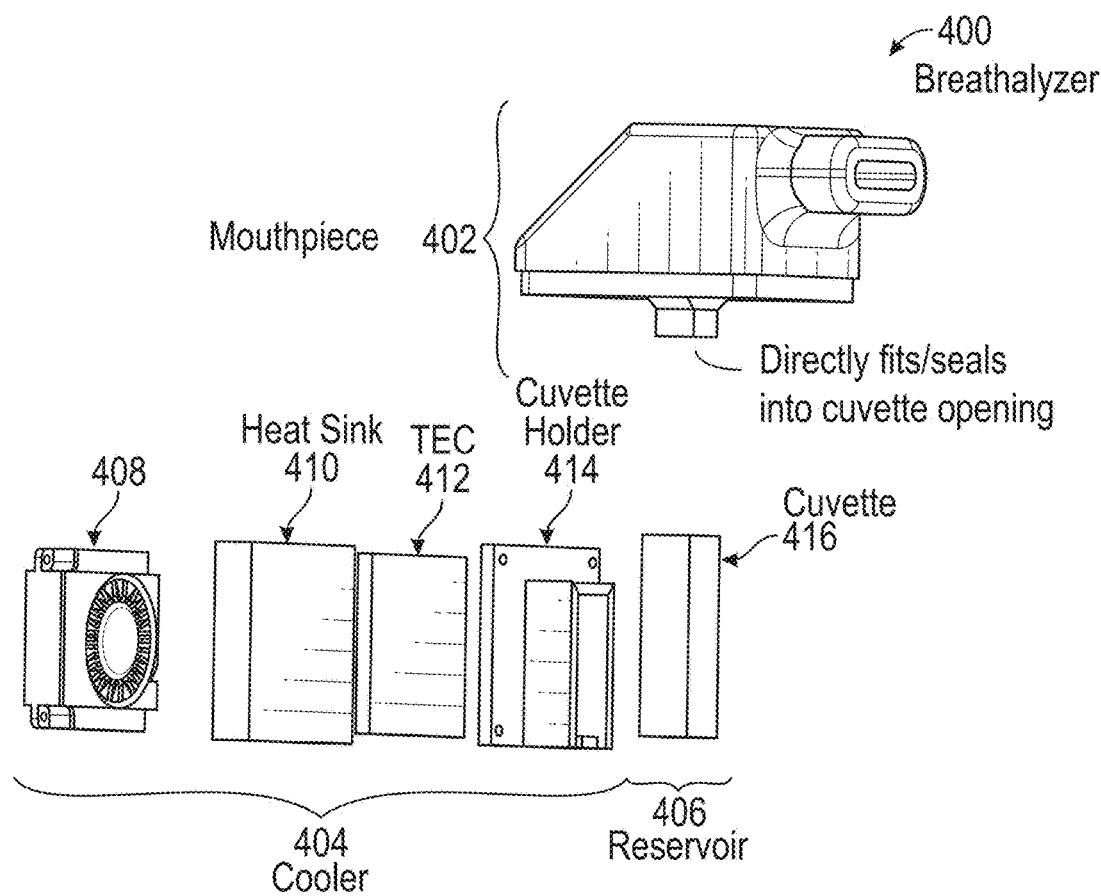
FIG. 4A depicts an example breathalyzer in some embodiments.

FIG. 4A depicts an example breathalyzer 400 in some embodiments. The breathalyzer 400 may enable a patron to breath through a mouthpiece 402. The breathalyzer 400 may receive a sample of the patron's breath. A spectrometer may receive the sample for analysis. The sample may be rejected from the breathalyzer 400 or may the breathalyzer 400 may be coupled to or within the spectrometer.

In the example breathalyzer 400 of FIG. 4A, the breathalyzer 400 is hand-sized. The breathalyzer 400 may include a mouthpiece 402, a cooler 404, and a reservoir 406. The example breathalyzer 400 is configured to receive the breath of the patron through the mouthpiece 402 and preserve samples from the breath of the patron in the reservoir 406. It will be appreciated that there may be many ways in which to collect and hold the breath sample. In this example, the cooler 404 assists to collect particles of interest of the breath of the patron by cooling the cuvette and allowing the particles (e.g., within or bound to moisture in the breath sample) to collect on a surface inside the cuvette.

In the example of the breathalyzer 400, the cooler 404 includes a fan 408, a heat sink 410, a thermoelectric cooler (TEC) 412, and a cuvette holder 414. The reservoir 406 includes the cuvette 416. The breathalyzer 400 may be hand-sized or be able to be manipulated and/or controlled with one or two hands. The breathalyzer 400 may include an outer housing that houses the cooler 404 and/or the reservoir 406. The mouthpiece 402 may be coupled to the housing. The housing may be made of plastic or other material. The outer housing may hold the components of the cooler 404 and the reservoir 406. The outer housing may also include a portal or lid which can be opened and the cuvette 416 removed from the breathalyzer 400. A new cuvette 416 may also be inserted into the breathalyzer 400 through the portal or lid.

In various embodiments, the mouthpiece 402 may include a conduit that is sealed directly to the cuvette 416 opening or through a conduit or other component that allows for a direct air path from the mouthpiece 402 to the cuvette 416. In various embodiments, the mouthpiece 402 is removable from the housing of the breathalyzer 400 and may be replaced or cleaned after being used by one or more patrons.

In one example, a patron may blow through a hole in the mouthpiece to direct air into the cuvette 416. A sample of the patron's breath may be held in the cuvette 416. The cuvette 416 may be ejected and/or the mouthpiece replaced with a new mouthpiece prior to the next patron breathing into the breathalyzer 400.

In various embodiments, the conduit and/or the mouthpiece 402 may include pressure release air passages to allow air to escape as the patron blows through the mouthpiece 402. In various embodiments, the cuvette 416 may include an air escape conduit to allow air to pass through the cuvette 416 and collect the sample. The air escape conduit may include a filter to prevent virus particles or the like from escaping the breathalyzer 400. In some embodiments, the air escae conduit may include a flap or other technique to prevent air from flowing from the outside the breathalyzer 400 back into the cuvette 416.

The cuvette 416 may be an optically clear container for holding samples (e.g., samples of the patron's breath). The cuvette 416 may be transparent or hold a removable sample substrate that is transparent. In various embodiments, the cuvette 416 is removable from the breathalyzer 400. In various embodiments, the cuvette 416 may be placed within a spectrometer or within the light beams of a spectrometer in order for a detector and analyzer to analyze absorption and/or transmittance.

In various embodiments, a spectrometer (e.g., a vortex spectrometer) may include a lid or portal to allow the cuvette 416 to be inserted and/or removed from the optical path of the spectrometer. The cuvette may be replaced with another cuvette containing a different breath sample from a different patron after each analysis. In some embodiments, multiple tests are run on the same cuvette to enable multiple measurements (e.g., "data snapshots"). This process may be used in conjunction with "lucky imaging" discussed herein to improve accuracy.

The cooler 404 may contain a fan 408 that directs air into or air out of the breathalyzer 400. The fan may be powered by a battery that is now shown in FIG. 4A or 4B. The battery may also power the TEC 412. The battery may run on any batteries such as commercial batteries, retail batteries, lithium ion, polymer, and/or the like.

A heat sink 410 may include a block of thermo-conductive material with or without fins to pull heat from the TEC 412. The fan 408 may remove heat form the heat sink 410 to assist in cooling. In various embodiments, the outer housing of the breathalyzer 400 may include slits or other air passages to allow hot air to pass out of the breathalyzer 400.

The TEC 412 may be any thermoelectric cooler that operates by the Peltier effect by creating a temperature difference between two electrical junctions. As voltage is applied across joined conductors, a current is induced that flows through the junctions of two conductors. Heat is removed at one junction (thereby creating cooling in that junction) and collects in the other. Heat is then transferred from the heated junction to the heat sink 410 which is subsequently cooled by the fan 408. It will be appreciated that the TEC 412 is optional (e.g., the cuvette 416 and/or the cuvette holder 414 may be in contact with the heat sink 410).

The cuvette holder 414 may be coupled between the cuvette 416 and the TEC 412. The cuvette holder 414 may be in contact with the TEC 412 to pull heat away from the cuvette 416. The TEC 412 may removably hold the cuvette 416 into position and enable the cuvette 416 to be removed and replaced (e.g., through the outer housing). The cuvette holder 414 may include a conductive surface to pull heat away from the cuvette 416.

In various embodiments, the cuvette 416 is cooled which will cause the breath sample of the patron to condense along the inside walls or substrate of the cuvette 416.

While the breathalyzer 400 is depicted as hand-sized, it will be appreciated that samples of the breath of a patron may be taken in any number of ways. For example, the patron may breath into a mouthpiece which directs the patron's breath to pane of transparent plastic (e.g., within or outside of a cuvee). The pane of transparent plastic may subsequently be used within a spectrometer (e.g., the mouthpiece may be coupled by a conduit to the pane of transparent plastic which may be within or coupled to a spectrometer). After the sample is analyzed by the spectrometer or digital device in communication with the spectrometer, then the pane of transparent plastic may be replaced or washed (e.g., with an alcohol solution or the like) to prepare for the next patron.

As discussed herein, the systems and methods described herein are not limited to utilizing breath samples of a breathalyzer.

Figure 4B:
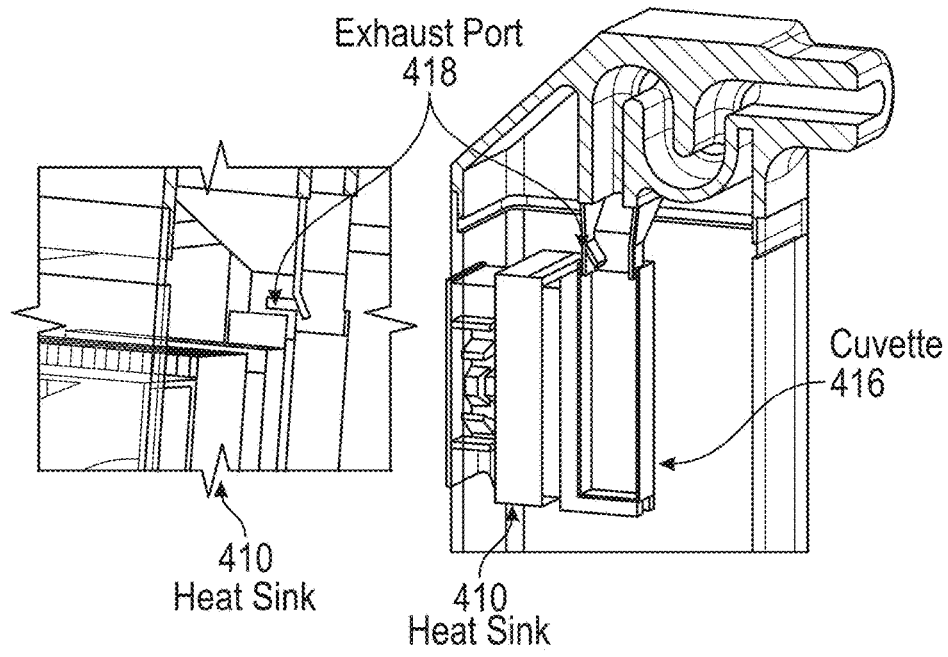
FIG. 4B is another view of the breathalyzer in some embodiments.

FIG. 4B is another view of the breathalyzer 400 in some embodiments. FIG. 4B depicts the breathalyzer 400 coupled. The cuvette 416 and/or the mouthpiece 402 may include an exhaust port 418 to assist with air escape and allow the sample to be collected. The exhaust port 418 may include a filter to prevent virus particles or the like from escaping the breathalyzer 400. In some embodiments, the exhaust port 418 may include a flap or other technique to prevent air from flowing from the outside the breathalyzer 400 back into the cuvette 416. The exhaust port 418 may allow for air from the breath of the patron to escape and be pushed out of the breathalyzer 400 by the fan 408 (e.g., through slits or openings of the outer housing which may or may not be filtered).

While a breathalyzer 400 is depicted in FIG. 4A and FIG. 4B, it will be appreciated that a sample of a patron may be taken in many different ways and used with systems described herein. For example, a patron may breath into the breathalyzer 400, provide a swab and the swab used to apply the patients fluids to a transparent substrate, or provide saliva which is applied to the transparent substrate. Any or all of these approaches may be used with the spectrometer with a vortex mask as described herein.

Figure 5:
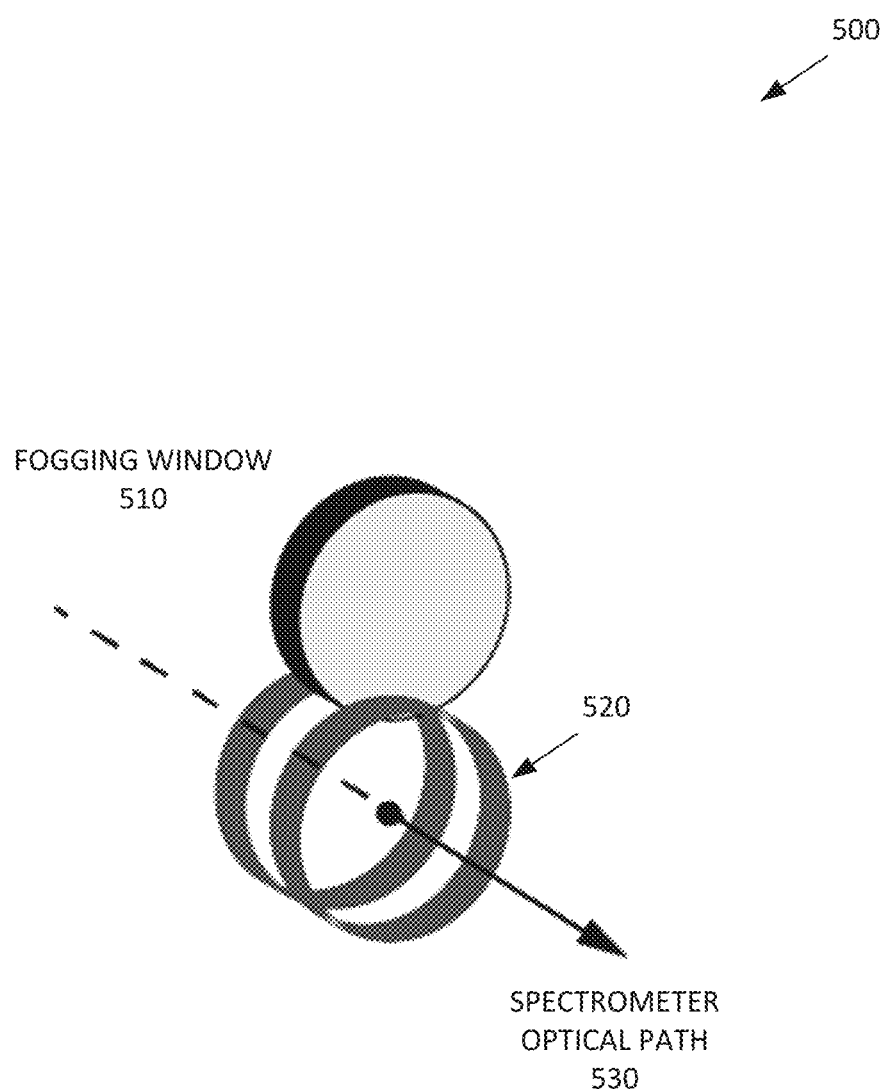
FIG. 5 depicts transparent substrates for collecting a sample a patron.

FIG. 5 depicts transparent substrates 500 for collecting a sample a patron. The transparent substrates 500 may be utilized to collect a breath sample (e.g., the patron exhaling on at least one of the transparent substrates 500), a saliva sample (e.g., applying the patron's saliva to at least one of the transparent substrates 500), or a swab sample (e.g., applying the residue from a swab sample on at least one of the transparent substrates 500).

The transparent substrates 500 may include a fogging window 510 and transparent members 520. In one example, the patron may breath or exhale on the fogging window 510. The transparent members 520 and/or the fogging window 510 may be cooled to collect moisture and particles from the user's sample.

The fogging window 510 may be coupled (e.g., rotationally coupled to a pin at or near a common edge) to the transparent members 520. In some embodiments, the fogging window 510 may be rotationally coupled to the transparent members 520. In one example, the fogging window 510 may be rotationally coupled by a peg or a point connected to both the transparent members 520 (e.g., along an edge) to allow the fogging window 510 to rotate out of being between the transparent members 520. In one example, the fogging window 510 may be rotated away from the transparent members 520 to allow a patron to exhale on the fogging window 510 without exhaling on the transparent members 520. After the fogging window 510 has collected a sample of the patron's breath, the fogging window 510 may rotate along the coupling point between the transparent members 520.

The transparent substrates 500 may then be inserted or coupled to a spectrometer. The spectrometer optical path 530 is a path for light projected by the spectrometer to a detector. In some embodiments, the spectrometer may have a portal or lid that allows the transparent substrates 500 to be inserted for analysis (e.g., as the sample cell) and then removed to make room for another set of transparent substrates 500 containing another breath sample from another patron.

The transparent members 520 may be made of any transparent material including, for example, glass or plastic. There may be any number transparent members 520 (e.g., one or more)

In some embodiments, the transparent substrates 500 and/or the fogging window 510 may be contained in the breathalyzer 400 and/or the cuvette 416. In other embodiments, the transparent substrates 500 may be unrelated to the breathalyzer 400. In this example, the transparent substrates 500 may be handled by a health professional wearing gloves and allow the patron to exhale on the fogging window 510.

There may be any number of fogging windows 510. For example, the transparent substrates 500 may include pairs of transparent members 520 with a fogging window 510 between each pair (e.g., four fogging windows 510 fogging window 510 between a pair of transparent members 520). Each fogging window 510 may be rotationally coupled to an axis to enable each fogging window 510 to rotate out from between the transparent members 520 independent of other plane windows 510.

In another example, there may be any number of fogging windows connected by the common pin. While one of the fogging windows 510 may be between the two transparent members 520, the other two fogging windows 510 may be outside the two transparent members 520. A first fogging window 510 between the two transparent members 520 may be placed within an optical path of a spectrometer. After measurements are taken, the transparent substrates 500 may be removed and the fogging window 510 rotated such that a second fogging windows 510 may be placed between the two transparent members 520 and placed within the spectrometer. After measurements of the second sample of the second fogging window 510 is taken, the transparent substrates 500 may be removed and the second fogging window 510 rotated such that a third fogging window 510 may be placed between the two transparent members 520 and placed within the spectrometer for additional measurements. Each fogging window 510 may contain a sample from a different patron or, in some embodiments, each fogging window 510 may contain a different breath sample from a different patron.

After analysis, the fogging window 510 and or the transparent members 520 may be cleaned or washed (e.g., using an alcohol-based solution, soap, and/or the like).

While FIGS. 2-5 refer to a breath analyzer, as discussed herein, some embodiments of systems and methods discussed herein utilize swabs or saliva samples from patients. The spectrometer may be a high-resolution transmission spectrometer associated with control software which measures in the ultraviolet to near-infrared ranges.

In some embodiments, the spectrometer measures the attenuation of the light passed through a clinical sample. The attenuance is a physical property of the sample directly related to its chemical and physical composition which comprises contributions due to absorption, scattering, and fluorescence.

For example, in the presence of COVID-19 infection, saliva and nasal swab samples collected from patients exhibit high loads of SARS-CoV-2 virions, the whole virus responsible for COVID-19. Additionally, samples contain high concentrations of proteins which did not self-assemble into viable virions, human proteins expressed in response to an active or latent SARS-CoV-2 infection, and detritus from damaged human cells caused by viral infection. These constituents enforce a chemically and biologically unique signature in collected samples which can be detected spectroscopically when they reach sufficient concentration. The unique chemical and protein composition of SARS-CoV-2 positive samples provide several channels which translate into optical response.

The first mechanism is physical scattering: whole SARS-CoV-2 particles are large nanoparticles of around 100 nm diameter, placing them in a size range where Mie scattering provides diagnostic information about the size of the scattering particle and its dielectric environment—principally in the ultraviolet to visible range. The second mechanism comes from the virus's chemical and protein composition and the composition of proteins produced by the body in response to infection: chemical specific absorption structure is imprinted onto the optical response.

The spectrometer and the assay making use of the spectrometer may be designed to perform high resolution attenuance measurements sensitive to these two proposed mechanisms while reducing and controlling for measurement variances. In various embodiments, the spectrometer uses a twofold approach to improving the signal-to-noise when viewed as an end-to-end system. The first example approach is to levy controls on the assay and data collection process to minimize variation between samples. In some embodiments, the spectrometer may utilize statistical denoising, matching filters, and inference algorithms as the analytical stage in the assay.

Because of differences in the physical size and chemical composition of different types of particles, each type of particle present in a sample displays different degrees of absorption, fluorescence and scattering when interacting with light at a particular wavelength. Considered across the range of wavelengths the spectrometer may measure, the combination of these interaction processes on the transmitted light imprints a signature of the composition of the sample: the set of spectral features.

Figure 6:
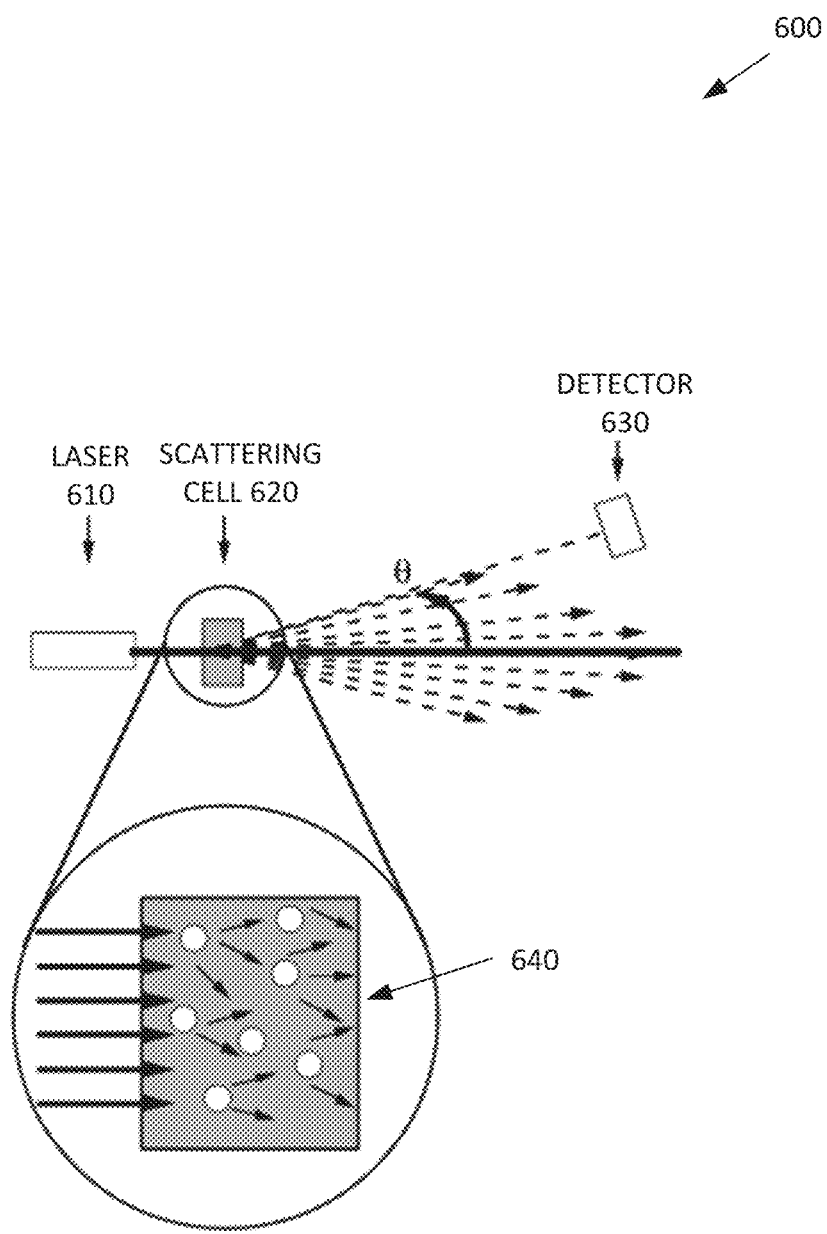
FIG. 6 depicts an absorption and scattering diagram in some embodiments.

FIG. 6 depicts an absorption and scattering diagram 600 in some embodiments. The absorption scattering diagram 600 may depict a process that occurs within the spectrometer. In this example, a laser 610 may project light along an optical path through the scattering cell 620. Scattering cell 620 may contain, for example, the cuvette 416, the transparent substrates 500, or the like. Light from the laser 610 may be absorbed and scattered as depicted in view 640. A detector 630 may be positioned such that the detector receives scattering of light at the desired wavelength.

Figure 7:
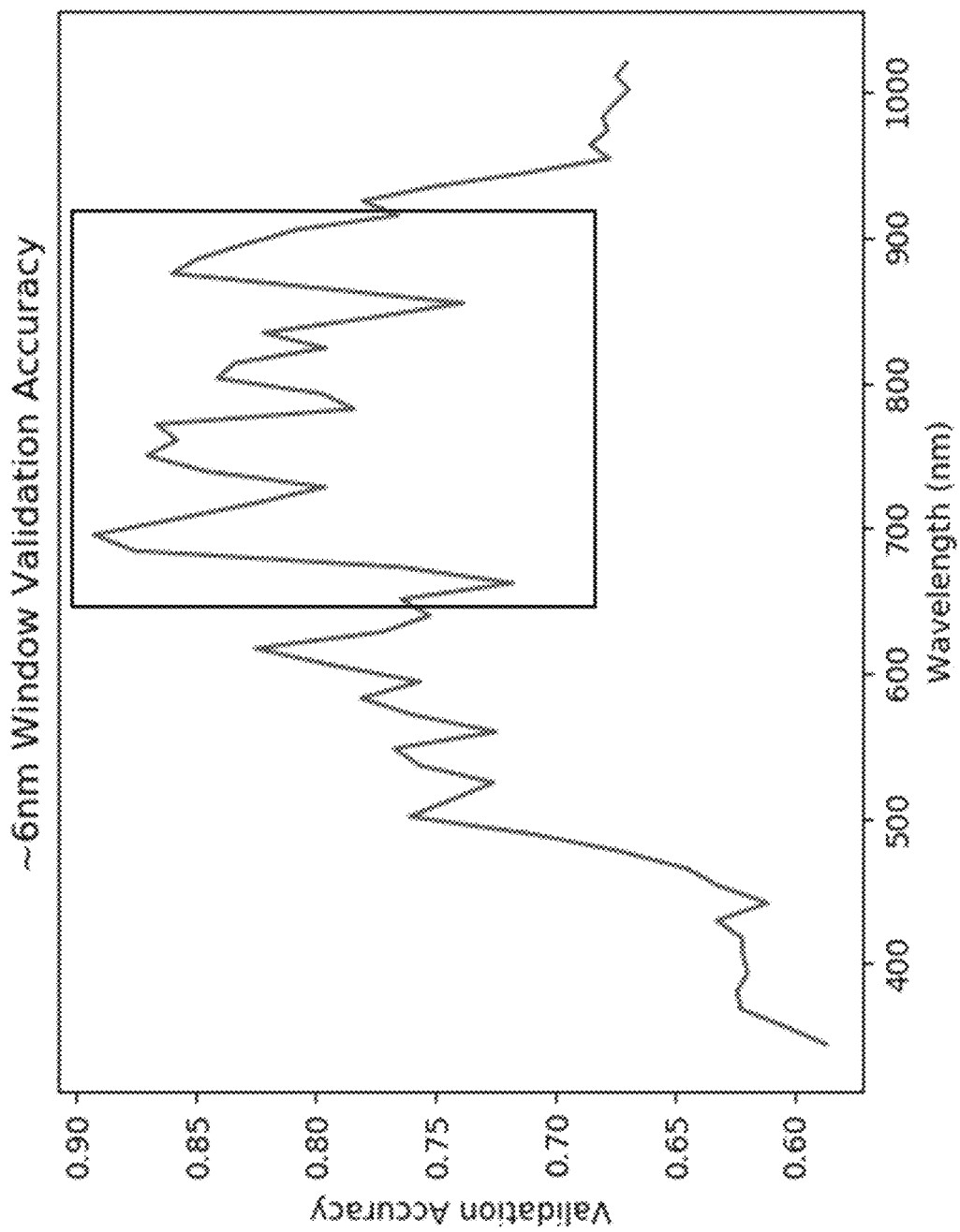
FIG. 7 depicts a window validation accuracy graph in some embodiments.

FIG. 7 depicts a window validation accuracy graph in some embodiments. In some embodiments, the output of the spectrometer may be or appear similar to the graph 700. In some embodiments, peaks of wavelength intensities at 735 nm, 780 nm, 810 nm, and 860 nm may suggest or indicate infection.

Figure 8:
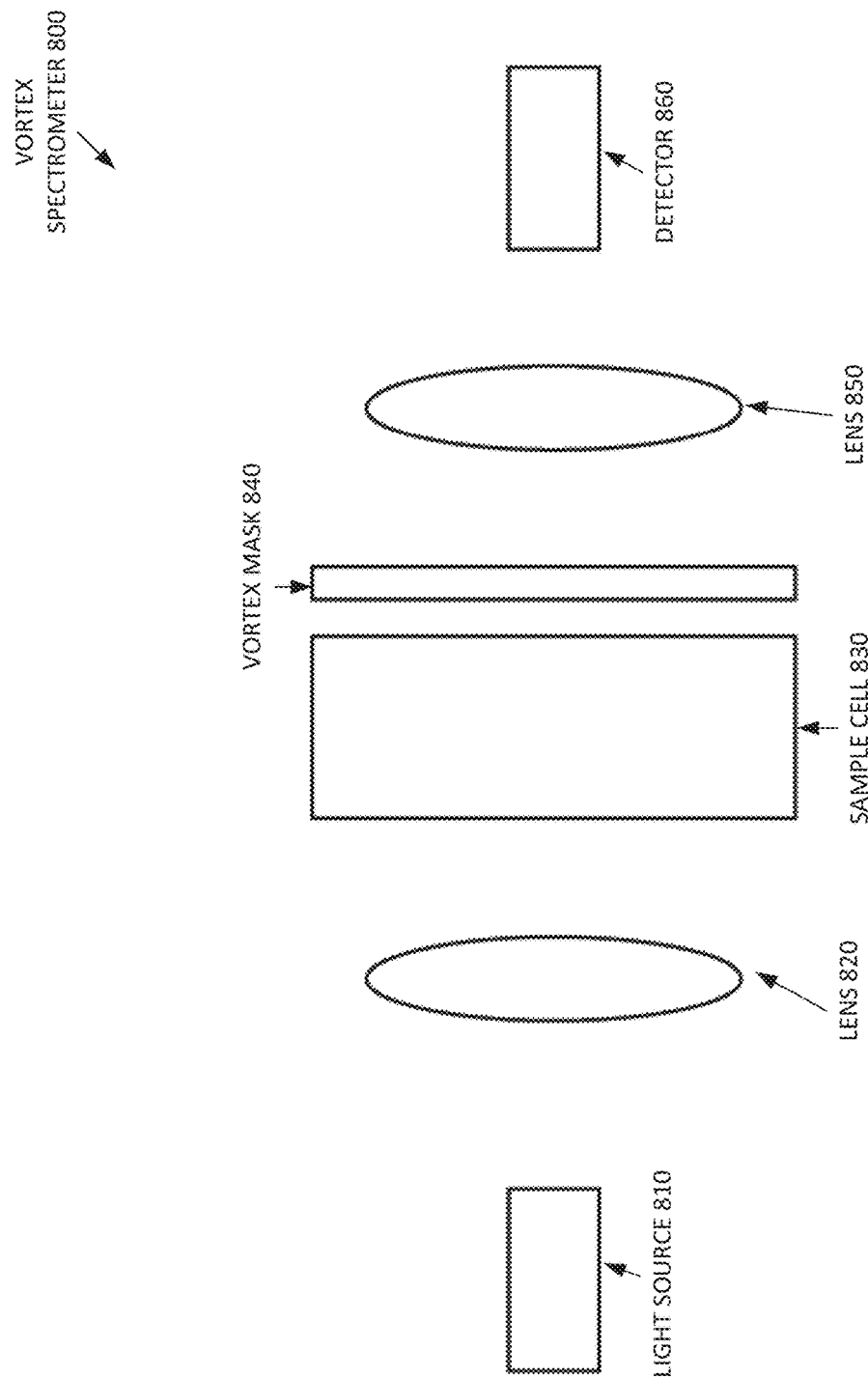
FIG. 8 depicts an example vortex spectrometer in some embodiments.

FIG. 8 depicts an example vortex spectrometer 800 in some embodiments. The spectrometer depicted in FIG. 8 is simplified. It may be appreciated that the spectrometer may include an aperture for controlling wavelengths, filters, beam splitters, diffraction grating, and the like as discussed herein.

The hardware of the vortex spectrometer 800 may be responsible for shaping and directing light through the collected sample, resolving the light by wavelength, and measuring the intensity. In various embodiments, light source (e.g., a standard tungsten-halogen source) emits broad bandwidth light spanning from the ultraviolet to near-infrared ranges which passes through the sample and cuvette. The vortex spectrometer 800 may measure the amount of absorption, scattering and fluorescence of wavelengths of light from the ultraviolet to the near-infrared by the sample, this combination of phenomena is collectively known as the spectral features of the sample. The vortex spectrometer 800 may count the arrival of particles of light on a sensor to produce the transmission spectrum. High reliability for the optical system may be achieved by using optical fiber coupling of the major components, with free space propagation of light through the sample, cuvette, and collimation and refocusing lenses.

The vortex spectrometer 800 of FIG. 8 includes a light source 810 (e.g., standard tungsten-halogen source or laser), first lens 820, sample cell 830, vortex mask 840, a second lens 850, and a detector 860. Light from a broadband light source 810 may be collimated by lens 820. The collimated light passes through a sample cell (e.g., containing the condensed breath of a patron), a vortex mask 840, and the second lens 850 before passing to the detector 860.

When the light passes through a scattering medium containing particles larger than the wavelength, light is scattered. The most intense scattering usually occurs in the forward direction. Light scattered along the optical axis is often difficult to distinguish from the superimposed unscattered laser beam, especially when there is a dilute concentration of weak scatterers. This scattered light may interfere with the light of the principle beam and, as a result, speckle (i.e., noise) may be formed.

In some cases, particular wavelengths may be absorbed by the scattering media. This occurs because the light at those particular wavelengths excite the rotational or vibrational state of the molecules in the media. Therefore, the chemical makeup of an absorbing media may be based on the spectral absorption signature that is present. If the medium is weakly scattering (i.e., there are few scatterers), the absorption signature may be overwhelmed by the strong on-axis unscattered light source. Therefore, in order to optimize the characterization of the scattering molecules, a light suppression technique may be utilized to attenuate the strong on-axis source while leaving the weaker scattered signal intact.

An optical vortex 840 is a dark null of destructive interference that occurs at a spiral phase dislocation in a beam of spatially coherent light. The phase of a transmitted light beam may be twisted and light from opposite sides of the mask may coherently destructively interfere to form a dark null in the transmitted intensity pattern, much like the eye of a hurricane.

The vortex mask 840 may assist to create destructive interference of the light source, thereby enabling improved sensitivity of fainter signals. In one example of the optical path shown in FIG. 8, light is projected from the light source 810 through the breath collection chamber and/or transparent member. The light then passes through the vortex mask 840 to be detected by the detector 860 which may digitizes the signal as a function of wavelength and provides the signal for further analysis and/or display.

In some embodiments, divergent light may be collimated by a concave mirror and directed into a grating to disperse the spectral components of the light at slightly varying angles which may be focused by a second concave mirror and imaged onto a detector.

The vortex mask 840 may be a vortex coronagraph configured to reduce unwanted glare from a spectrometer light source. As discussed herein, the spectrometer may include or be coupled to a vortex mask in order to reduce or eliminate undesired wavelengths and/or light intensities of the light that passed through the sample cell 830. The vortex mask 840 may include or be an optical vortex coronagraph that uses a phase-mask in which the phase-shift varies azimuthally around the center. The vortex mask 840 may use interference to mask out light along the center axis of the optical path of the spectrometer but allows light from off axis.

A vortex mask 840 may be used to create an optical vortex to reduce or eliminate unwanted light from the spectrometer light sources. Without reducing undesirable light from the spectrometer light sources, many signals may otherwise be too faint to be detected (e.g., faint signals from desired absorption or transmittance is overwhelmed by the other signals caused by the light sources).

In some embodiments, the vortex mask 840 may be or utilize an optical vortex coronagraph. An example optical vortex coronagraph uses a helical phase of the form $ei\phi$, with $\phi=l\theta$, where l is the topological charge and $\theta$ is the focal plane azimuthal coordinate. In optical systems, vortices manifest themselves as dark donut of destructive interference that occur at phase singularities. For example, $E(\rho, \phi, z, t) = A(\rho, z) \exp(il\theta) \exp(i\omega t - ikz)$ where $(\rho, \phi, z)$ are cylindrical coordinates, $A(\rho, z)$ is a circularly symmetric amplitude function and $k=2\pi/\lambda$, is the wavenumber of a monochromatic field of wavelength $\lambda$.

In some embodiments, the optical vortex coronagraph may utilize a rotationally symmetric half wave plate which can generate an azimuthal phase spiral reaching an even multiple of 2pi radian.

The vortex mask 840 may include an optical vortex induced by an achromatic subwavelength grating. In some embodiments, the vortex mask 840 maybe an annular groove phase mask coronagraph. As discussed herein, without the vortex mask 840, detection of faint sources around significant noise may be difficult due to the large ratio between them.

In various embodiments, the vortex mask 840 is not a pure amplitude mask, a pure phase mask, a single pupil achromatic nulling interferometer, or a monochromatic pupil plane mask. In one example, the vortex mask 840 may be an annular groove phase mask coronagraph. The vortex mask 840 may include a focal plane that is divided into four equal areas centered on an optical axis. Unlike a mask where two of the focal planes are on a diagonal providing a $\pi$ phase shift to cause destructive interference inside a geometric pupil area, the vortex mask 840 utilizes subwavelength gratings while suppressing "dead zones" (e.g., where potential circumstellar signal or companion is attenuated by up to 4 magnitudes). The vortex mask 840 may include concentric circular subwavelength gratings.

Figure 9A:
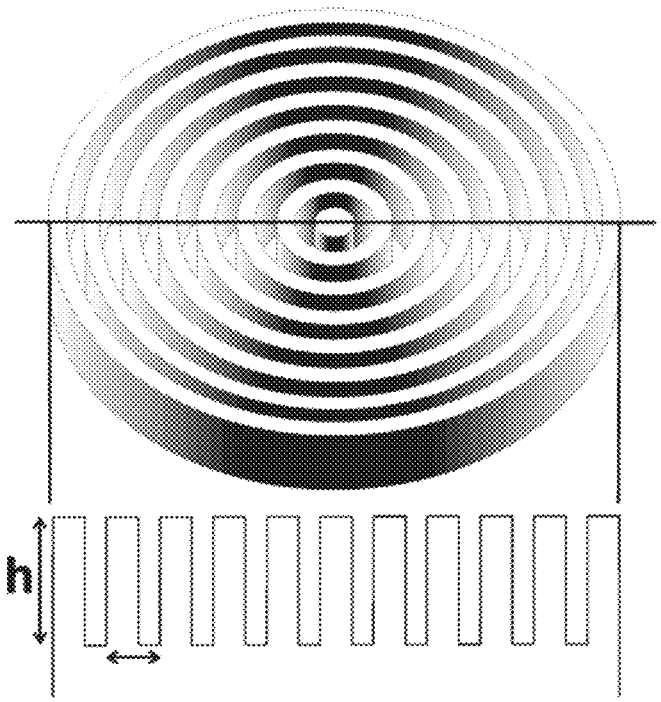
FIG. 9A depicts an example coronagraph scheme including a concentric circular surface relief grating with rectangular grooves with depth h and a periodicity of A.

The vortex mask 840 may include a focal plane microcomponent including a concentric circular surface-relief grating with rectangular grooves of depth h and equally separated by a period A. FIG. 9A depicts an example coronagraph scheme including a concentric circular surface relief grating with rectangular grooves with depth h and a periodicity of A. in some embodiments, the vortex mask 840 may be a vectorial phase mask (i.e., the vortex mask 840 induces a differential phase shift between the local polarization states of the incident natural (or polarized) light).

When the period A of the grating is smaller than the wavelength of the incident light, the vortex mask 840 does not diffract as a classical spectroscopic grating. Incident energy is enforced to propagate only in the zeroth order, leaving incident wavefronts free from any further aberrations. In various embodiments, the subwavelength gratings of the vortex mask 840 may be Zeroth Order Gratings.

Figure 9B:
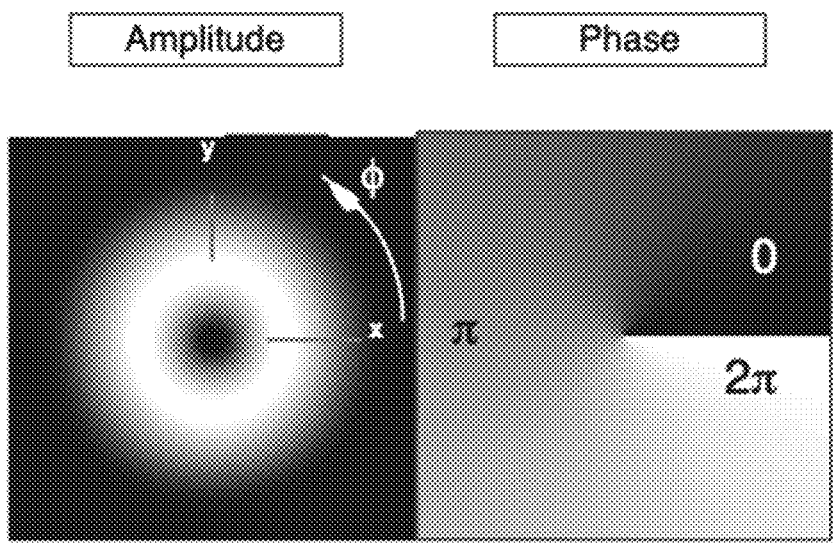
FIG. 9B includes images of amplitude and phase caused by the vortex mask in some embodiments.

By controlling the geometry of the grating structure, the vortex mask 840 may be tuned (e.g., to make the form birefringence proportional to the wavelength in order to achromatize the subsequent differential $\pi$ phase shift between two polarization states). This may create an optical vortex where phases possess a screw dislocation inducing a phase singularity. The central singularity forces the intensity to vanish by a total destructive interference, creating a dark core. This dark core propagates and is conserved along the optical axis. In various embodiments, the vortex mask 840 creates an optical vortex in the focal plane, filtering in the relayed pupil plane and making the detection in a final image plane. FIG. 9B includes images of amplitude and phase caused by the vortex mask 840 in some embodiments.

In various embodiments, the vortex mask 840 may be fabricated by imprinting the concentric annular mask in a resin coated on a chosen substrate material. For example, fabrication may be performed, in part, by laser direct writing or e-beam lithography. This process may define the lateral dimensions of the Zeroth Order Gratings (ZOG). This pattern may then be uniformly transferred in the substrate by an appropriate reactive plasma ion beam etching down to the desired depth.

In some embodiments, a space-variant half-wave plate may be used to generate the optical vortex. In one example, a beam of light containing an optical vortex is described by an electric field distribution that may be expressed E (x, y, z)=A(x, y, z)exp (i$\Phi$(x, y, z))exp (im$\theta$) where A and $\phi$ are arbitrary amplitude and phase functions respectively. $\theta$ is an angle about the vortex core located at ($x_v$, $y_v$): $x-x_v$=cos $\theta$ and $y-y_v$=sin $\theta$, and m is an integer called the vortex charge (or vortex topological charge). There are various techniques to convert a given input beam into an output contained an arbitrary distribution of optical vortices. In this example, this method makes use of a space variant half-wave retarder and a circularly polarized input beam. For convenience, the input beam is right circularly polarized.

A conventional half-wave plate may convert a right circularly polarized beam into a left circularly polarized beam without introducing a spatially varying phase on the output beam. This may be accomplished with a birefringent material such as a nematic liquid crystal. In this example, the refractive index depends on the linear polarization components of the beam. The horizontal and vertical polarization components of the right circularly polarized input beam may be represented by variable $E_{x,in}$=1 and $E_{y,in}$=−i, where i=$\sqrt{-1}$. The output beam may have horizontal and vertical components that are a linear combination of the input components. For a half-wave retarder with the fast crystal axis making an angle $\theta'$ with respect to the x-axis, the output field may be expressed:

$$\begin{bmatrix} E_{x,out} \\ E_{y,out} \end{bmatrix} = \begin{bmatrix} \cos\theta' & -\sin\theta' \\ \sin\theta' & \cos\theta' \end{bmatrix} \begin{bmatrix} \exp(i\pi/2) & 0 \\ 0 & \exp(-i\pi/2) \end{bmatrix} \begin{bmatrix} \cos\theta' & \sin\theta' \\ -\sin\theta' & \cos\theta' \end{bmatrix} \begin{bmatrix} E_{x,in} \\ E_{y,in} \end{bmatrix}$$

when $$\theta' = \frac{\pi}{4},$$

$E_{x,out}$=1 and $E_{y,out}$=i, which describes left circular polarization. The principle of a space-variant half-wave retarder can be reduced making use of the trigonometric identity tan (2u)=2 tan u/(1−tan$^2$ u):

$$\begin{bmatrix} E_{x,out} \\ E_{y,out} \end{bmatrix} = ie^{-\phi} \begin{bmatrix} 1 \\ i \end{bmatrix}$$

where tan $\phi$=tan 2$\theta'$, or equivalently, $\phi$=2$\theta'$. The spatial phase distribution of the output left circularly polarized beam may be controlled by spatially varying the angle of the crystal fast axis. For example, for a vortex of charge m=−2 having a spatial phase distribution exp (−i2$\theta$), the fast axis of the crystal may be spatially oriented by the exact angular coordinate $\theta'$=$\theta$, where $\theta$ corresponds to the (x,y) location of the material: x=cos $\theta$, y=sin $\theta$. Likewise, for a vortex beam of charge m=−4, the fast axis is rotated by an amount $\theta'$=2$\theta$.

The half-wave phase factors in the equation above, exp (±i$\pi$/2) may be achieved when the following birefringent material condition is satisfied: $\pi(n_e-n_o)L/\lambda=\pi/2$ where $n_o$ and $n_e$ are the ordinary and extraordinary refractive indexes, respectively, L is the thickness of the material, and $\lambda$ is the wavelength of light. This "half-wave" condition can only be satisfied at a single wavelength. The conversion efficiency of the right circularly polarized input beam to the left circularly polarized output beam having a vortex phase decreases as a function of wavelength. To rectify this shortcoming and for efficiency across a band of wavelength, an achromatic half-wave retarder may be used.

Broadband wave retarders may be constructed by stacking multiple layers of the same birefringent material at different orientations. Achromatic and superachromatic wave plates may be constructed from three more layers. A three-layer achromatic half-wave plate is described below. The electric field vector may be described with Jones matrix formalism:

$$\begin{bmatrix} E_{x,out} \\ E_{y,out} \end{bmatrix} = \begin{bmatrix} C_{1,1} & C_{1,2} \\ C_{2,1} & C_{2,2} \end{bmatrix} \begin{bmatrix} B_{1,1} & B_{1,2} \\ B_{2,1} & B_{2,2} \end{bmatrix} \begin{bmatrix} A_{1,1} & A_{1,2} \\ A_{2,1} & A_{2,2} \end{bmatrix}$$

$$\begin{bmatrix} E_{x,in} \\ E_{y,in} \end{bmatrix} = \begin{bmatrix} M_{1,1} & M_{1,2} \\ M_{2,1} & M_{2,2} \end{bmatrix} \begin{bmatrix} E_{x,in} \\ E_{y,in} \end{bmatrix}$$

Where $$\begin{bmatrix} A_{1,1} & A_{1,2} \\ A_{2,1} & A_{2,2} \end{bmatrix} = \begin{bmatrix} \cos\theta_a & -\sin\theta_a \\ \sin\theta_a & \cos\theta_a \end{bmatrix} \begin{bmatrix} \exp(i\gamma_a) & 0 \\ 0 & \exp(-i\gamma_a) \end{bmatrix} \begin{bmatrix} \cos\theta_a & \sin\theta_a \\ -\sin\theta_a & \cos\theta_a \end{bmatrix}$$

$$\begin{bmatrix} B_{1,1} & B_{1,2} \\ B_{2,1} & B_{2,2} \end{bmatrix} = \begin{bmatrix} \cos\theta_b & -\sin\theta_b \\ \sin\theta_b & \cos\theta_b \end{bmatrix} \begin{bmatrix} \exp(i\gamma_b) & 0 \\ 0 & \exp(-i\gamma_b) \end{bmatrix} \begin{bmatrix} \cos\theta_b & \sin\theta_b \\ -\sin\theta_b & \cos\theta_b \end{bmatrix}$$

$$\begin{bmatrix} C_{1,1} & C_{1,2} \\ C_{2,1} & C_{2,2} \end{bmatrix} = \begin{bmatrix} \cos\theta_c & -\sin\theta_c \\ \sin\theta_c & \cos\theta_c \end{bmatrix} \begin{bmatrix} \exp(i\gamma_c) & 0 \\ 0 & \exp(-i\gamma_c) \end{bmatrix} \begin{bmatrix} \cos\theta_c & \sin\theta_c \\ -\sin\theta_c & \cos\theta_c \end{bmatrix}$$

Although the ordinary $n_o$ and the extraordinary $n_e$ refractive indexes vary with wavelength, for first order design purposes the birefringence $\Delta n=n_e-n_o$ is often assumed to be nearly constant. The wavelength-dependent phase retardance Y' or a layer of thickness L may be expressed: $2\gamma=\Delta\Phi(\lambda)=2\pi(n_e-n_o)L/\lambda\approx 2\pi L\Delta n(1-\delta\lambda/\lambda)/\lambda_0$ where $\lambda=\lambda_0+\delta\lambda$ and $\lambda_0$ is a central design wavelength for the achromatic retarder.

The waveplate may be achromatized if $\gamma_a = \gamma_c$ and $\theta_a = \theta_c$. In effect, the first and last materials may be the same and the orientations are parallel. The final conditions are that cos $2\theta_b = -\gamma_{b,0}/2\gamma_{a,0}$ and $\gamma_{b,0} = \pi/2$. Hence cos $2\theta_b = -\pi/4\gamma_{a,0}$.

Figure 9C:
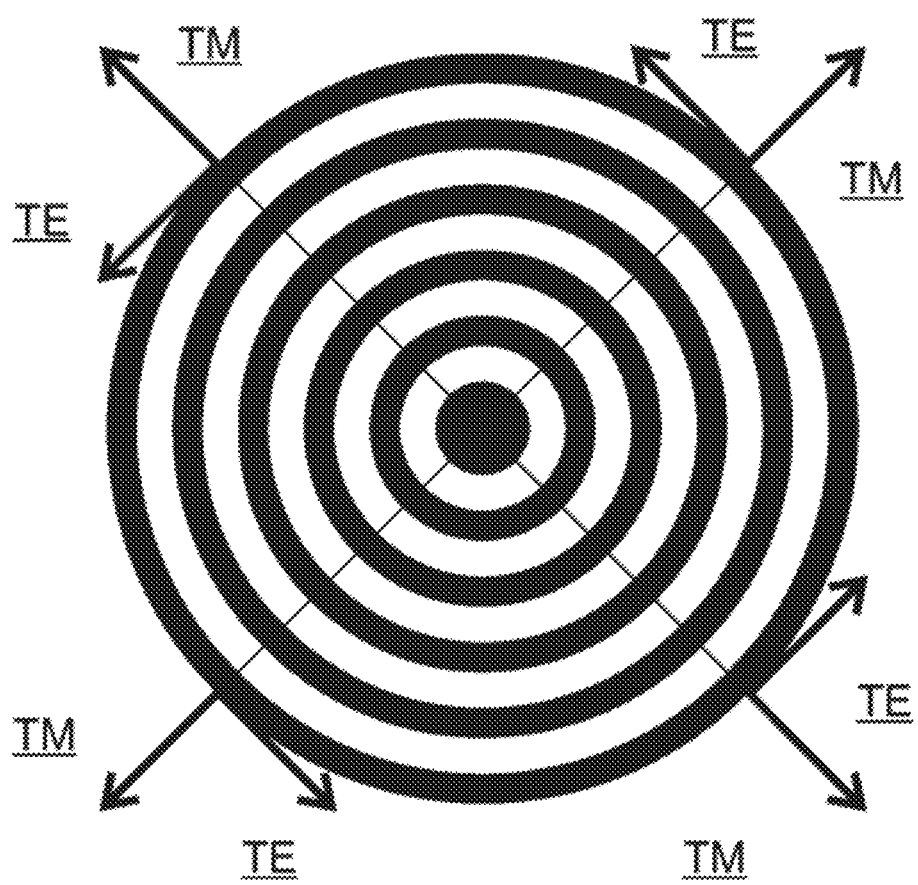
FIG. 9C depicts an example of a vortex mask which can be seen as a polarization FQ-PM.

FIG. 9C depicts an example of a vortex mask which can be seen as a polarization FQ-PM. The parallel potentially interfering polarization states are out of phase according to the FQ-PM focal plane phase shift distribution. ΦTE and ΦTM are the output phases of the polarization components TE and TM such that ΔΦTE−TM=|ΦTE−ΦTM|=π. While some constructions and configurations of AGPMs have been used for astronomy, none have been used for spectroscopy for detection of information in faint signals with significant noise.

The vortex mask 840 may be complemented by a diaphragm in the relayed pupil plane ("lyot stop") to suppress diffracted light.

Figure 10A:
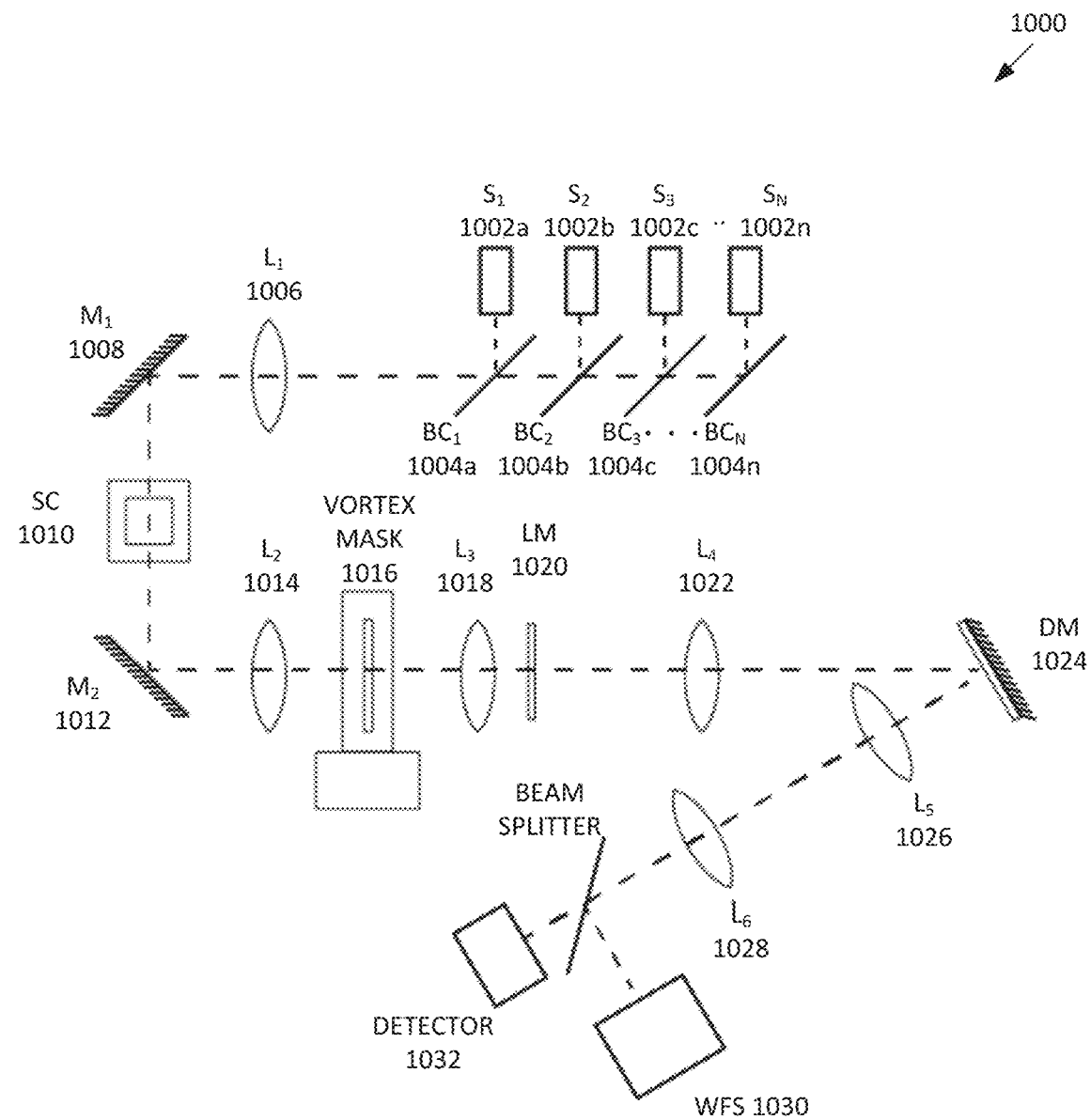
FIG. 10A depicts an example simplified spectrometer optical path in some embodiments.

FIG. 10A depicts an example simplified spectrometer optical path 1000 in some embodiments. One or more light sources may project desired wavelengths along the optical path 1000 through the sample 1010 and then through a vortex mask 1016 to a detector 1032. The vortex mask 1016 may assist with improved signal measurement and signal boosting. As such, measurements of the resulting signal enable a discriminator to detect viruses and/or substances related to viruses (e.g., proteins) to detect infections that were previously too faint to detect.

In various embodiments, the optical path 1000 includes a vortex mask 1016 but not a lyot mask 1020. In other embodiments, the optical path 1000 includes a vortex mask and a lyot mask.

Light sources 1002a-n each project light at a different wavelength. In some embodiments, a single laser projects coherent light through a differential grating to separate the wavelengths. In other embodiments, different light sources may project different wavelengths (1002a may be a different wavelength from 1004b and the like). Each Sn may be a different and distinct wavelength as compared to all other sources.

Example wavelengths include, for example, 860 nm, 810 nm, 780 nm, and 735 nm. These wavelengths may, for example, be useful in detecting evidence of COVID-19 infection in a breath sample collected from patron.

The light sources 1002a-n may be or include five co-boresighted laser sources that create a light source with an 8 mm collimated beam (or other diameter beam may be produced such as 3 mm, 4 mm, 5 mm, 6 mm, 7 mm, 9 mm, or 10 mm for example). Each light source 1002a-n may be or include an FC fiber connected to an achromatic collimator that sets the output beam width. In one example, light sources 1002a-n are diode laser sources of various wavelengths. Collimated light from each light source 1002a-n is reflected from the surface of a 55/45 beam splitter or beam comber (BC1-BC4).

Beam combiners 1004a-1004n each may allow some wavelengths to pass while reflecting at least one wavelength (e.g., combining optical wavelengths). In one example, beam combiner 1004a may reflect light at a first wavelength from source 1002a and the beam combiner 1004a may allow other wavelengths to pass through (e.g., light from sources 1002b-1002n). The light from each source may be projected through lens 1006. Lens 1006 may be a collimator to collimate the light received from the light sources.

Reflective surfaces 1008 and 1012 may reflect all light from the sources. In one example, light from sources 1002a-1002n is reflected by reflective surface 1008 through sample chamber 1010. The sample chamber 1010 may contain a sample (e.g., breath, saliva, or swab sample) from a patron. In various embodiments, the sample chamber 1010 is or contains the cuvette 416. In another example, the sample chamber 1010 is or contains transparent substrates 500. The light from the sources pass through the sample chamber 1010 and then is reflective by reflective surfaces 1012.

The second section of the optical path 1000 propagates the collimated beam through a scattering sample of the sample chamber 1010. In one example, a collimated beam from the light source is reflected perpendicularly from reflective surface M1 1008 through a sample cuvette holder (i.e., the sample chamber 1010). In this example, the entrance aperture of the sample chamber 1010 has a 9 mm diameter. The sample chamber 1010 may contain a sample in a liquid medium and may have a width of 10 mm perpendicular to the beam and a length parallel to the beam of 2 mm.

In one example, the sample chamber 1010 may be filled with approximately 1 ml of liquid so the full 8 mm beam passes through the sample. The residual collimated beam and the light scattered off the sample may then reflected perpendicularly off of reflective surface M2 1012 and exits to the next section of the optical path.

Light then is further focused by lens 1014 on the vortex mask 1016. The lens 1018 may focus the light on the optional lyot mask 1020 and/or may collimate the light received from the vortex mask 1016.

Optional LM mask 1020 may be a lyot-mask (e.g., lyot stop) such as a lyot-plane phase mask, which enables improved contrast performance. The lyot-plane phase mask may relocate residual light away from a region of the image plane, thereby reducing light noise from the sources of the spectrometer and improves sensitivity to off-axis scattered light.

It may be appreciated that, in some embodiments, the spectrometer includes a vortex mask 1016, a lyot mask 1020, or both (e.g., the spectrometer may include a lyot mask 1020 but not a vortex mask 1016, a lyot mask 1020 and a vortex mask 1016, or vortex mask 1016 but not a lyot mask 1020).

The lens L4 1022 may collimate the light and/or focus on the light on the optional deformable mirror 1024. In some embodiments, the lens L4 1022 may focus the light on the deformable mirror 1024 (e.g., to a desired diameter).

The deformable mirror 1024 may, in some embodiment, may control the wave front of the light based on information received from the wave front sensor 1030. In this example, the light may magnify and/or enhance the light of the optical path. Control of the deformable mirror 1024 may allow for control of the wave front of the light to direct a flat wave front to the detector 1032. It will be appreciated that, in some examples, the optical path 1000 may not have a deformable mirror 1024. In that case, the optical path 1000 may not have a beam splitter or a wave front sensor0 (WFS) 1030.

The detector 1032 detects spectral components (e.g., intensities of received wavelengths). In various embodiments, the detector 1032 is part of a spectrometer, a photodiode, or an LCD camera. The detector may generate measurements indicating intensities of wavelengths from the incoherent light of the optical path. The detector may provide absorption r transmittance measurements related to the particles and components of the breath sample.

In one example, the detector 1032 is in communication with a processor to assess and generate the measurement results. The measurement results may then be used to identify if the patron that produced the breath sample is infected.

The measurement results may be received by a discriminator. A discriminator may categorize or determine if the patron is infected by assessing and/or analyzing the measurement results. The discriminator may assess the measurement results using a logistic regression technique, an AI approach (e.g., convolutional neural network), and/or other statistical methods. In some embodiments, the measurement results may be used to create and/or train the discriminator.

In various embodiments, there is a beam splitter in the optical path before the detector thereby enabling the beam to be split between the detector 1032 and the wavefront sensor (WFS) 1030. A wavefront sensor 1030 is a device for measuring aberrations in an optical wavefront (e.g., points where the wave has the same phase as the sinusoid) and controlling the deformable mirror 1024 to correct and flatten the optical wavefront.

Lens l5 1026 and lens l6 1028 may also focus and collimate the light to project to the wave front sensor 1030 and/or detector 1032.

Figure 10B:
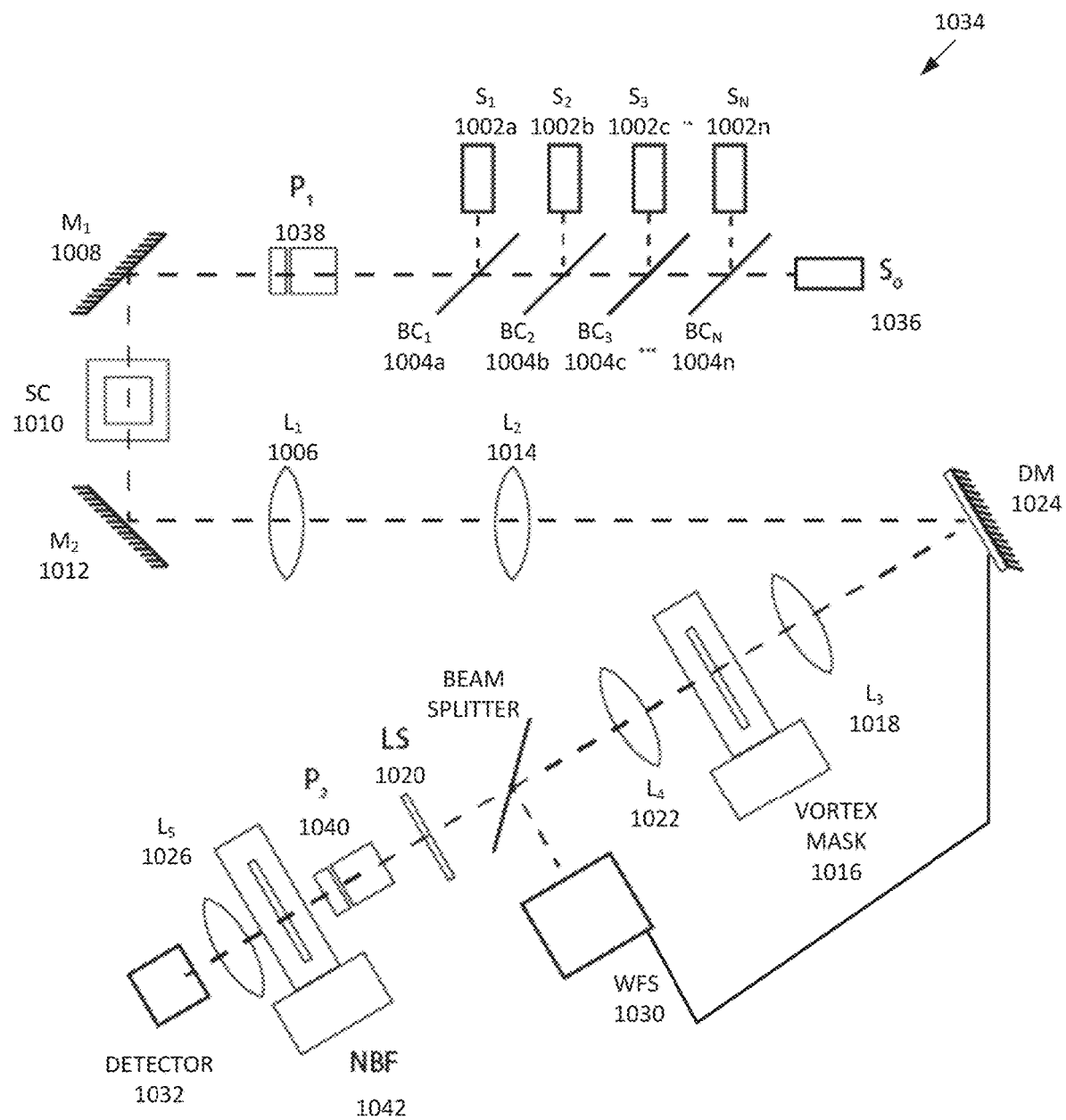
FIG. 10B depicts another example simplified spectrometer optical path in some embodiments.

FIG. 10B depicts another example simplified spectrometer optical path 1034 in some embodiments. Similar to FIG. 10A, the light sources 1036 and 1002a-n project desired wavelengths along the optical path 1034 through the sample 1010 and then through a vortex mask 1016 to a detector 1032. The vortex mask 1016 may assist with improved signal measurement and signal boosting. As such, measurements of the resulting signal enable a discriminator to detect viruses and/or substances related to viruses (e.g., proteins) to detect infections that were previously too faint to detect. In this example, different from FIG. 10A, the vortex mask 1016 and the optional lyot stop 1020 has been moved to after the deformable mirror 1024.

Figure 11B:
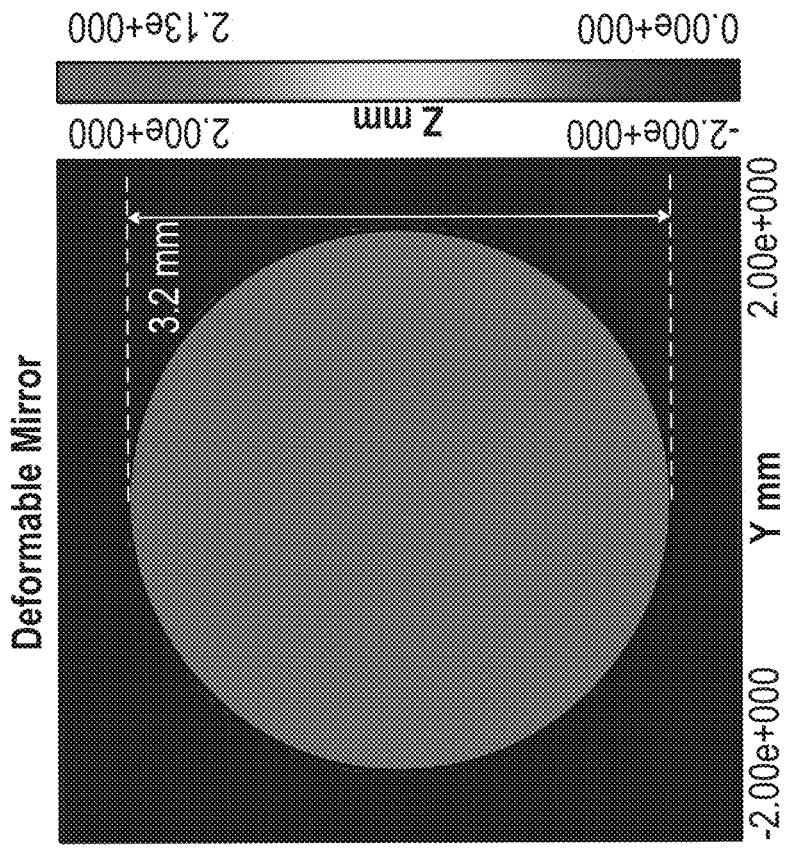
FIG. 11B depicts a measurement of an optical beam received and reflected by a deformable mirror in some embodiments.
Figure 11A:
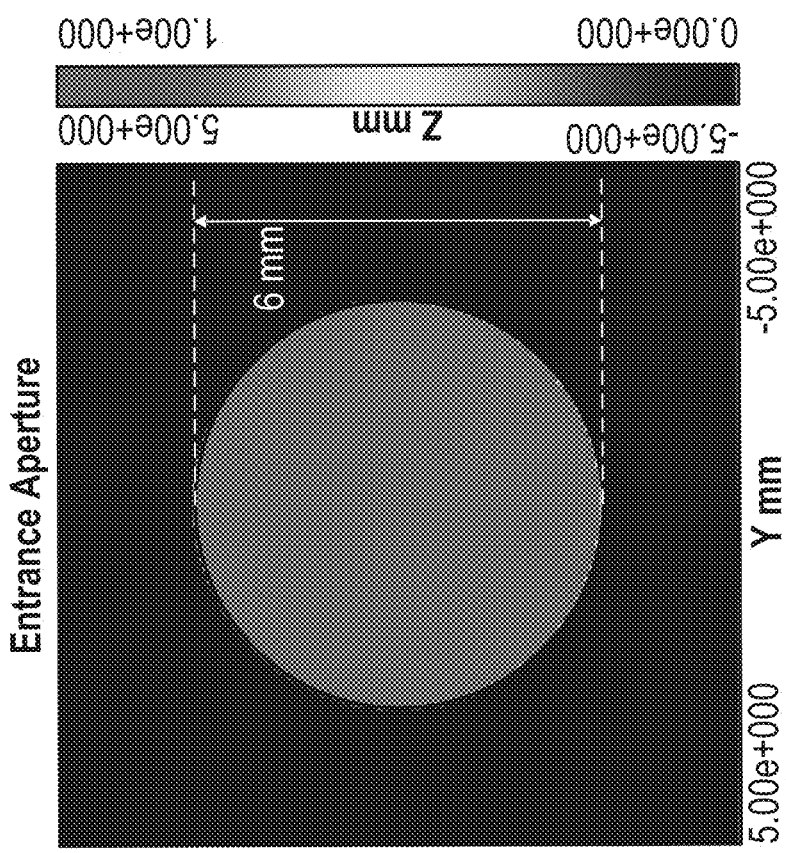
FIG. 11A depicts a measurement of the aperture of an entrance aperture as being 6 mm in one example.

In various embodiments (e.g., in any spectrometer discussed herein), the beam size may be narrowed to ensure that the beam passes through the cuvette and not clip a corner or edge of the cuvette. The beam sized may be 4 mm from the light source (e.g., at the entrance aperture) for example. Other examples of the beam size may be 4 mm to 8 mm. The lens from M2 1012 may be reduced to 3.2 mm on the deformable mirror 1024. Other examples of the beam size may be 3 mm to 4 mm. In some embodiments, lens 1006 and 1014 reduce the beam to the deformable mirror 1024. FIG. 11A depicts a measurement of the aperture of an entrance aperture as being 6 mm in one example. In this example, the aperture accommodates an optical beam with a 6 mm diameter. FIG. 11B depicts a measurement of an optical beam received and reflected by a deformable mirror in some embodiments. In this example, the deformable mirror accommodates an optical beam of a 3.2 mm diameter received from one or more lenses along the optical path 1034.

In various embodiments, the optical path 1034 includes a vortex mask 1016 but not a lyot mask 1020. In other embodiments, the optical path 1034 includes a vortex mask 1016 and a lyot mask 1020.

Light sources 1036 and 1002a-n each project light at a different wavelength. In some embodiments, a laser projects coherent light through a differential grating to separate the wavelengths. In other embodiments, different light sources may project different wavelengths (1002a may be a different wavelength from 1004b and the like). Each Sn may be a different and distinct wavelength as compared to all other sources.

Example wavelengths include, for example, 860 nm, 810 nm, 780 nm, and 735 nm. These wavelengths may, for example, be useful in detecting evidence of COVID-19 infection in a breath sample collected from patron.

The light sources 1036 and 1002a-n may be or include five co-bore-sighted laser sources that create a light source with an 8 mm collimated beam. The light source S0 1036 may be a control wavelength. In some embodiments, the light source S0 1036 is 635 nm.

The light sources 1002a-n and/or the light source 1036 may be or include five co-bore-sighted laser sources that create a light source with an 8 mm collimated beam. Each light source 1036 and 1002a-n may be or include an FC fiber connected to an achromatic collimator that sets the output beam width to 8 mm. In one example, light sources 1036 and 1002a-n are diode laser sources of various wavelengths. Collimated light from each light source 1036 and 1002a-n is reflected from the surface of a 55/45 beam splitter or beam comber (BC1-BC4).

In some embodiments, the spectrometer may include a white light source. In this configuration, the FC connected fiber from a laser diode source S1 is replaced with a fiber fed light source from a tungsten halogen bulb projecting white light.

Beam combiners 1004a-1004n each may allow some wavelengths to pass while reflecting at least one wavelength (e.g., combining optical wavelengths). In one example, beam combiner 1004a may reflect light at a first wavelength from source 1002a and the beam combiner 1004a may allow other wavelengths to pass through (e.g., light from sources 1002b-1002n). The light from each source may be projected through lens 1006. Lens 1006 may be a collimator to collimate the light received from the light sources.

Reflective surfaces 1008 and 1012 may reflect all light from the sources. In one example, light from sources 1002a-1002n is reflected by reflective surface 1008 through sample chamber 1010. The sample chamber 1010 may contain the breath sample, saliva, or other sample from a patron. In various embodiments, the sample chamber 1010 is or contains the cuvette 416. In another example, the sample chamber 1010 is or contains transparent substrates 500. The light from the sources pass through the sample chamber 1010 and then is reflective by reflective surfaces 1012.

The second section of the optical path 1034 propagates the collimated beam through a scattering sample of the sample chamber 1010. In one example, an 8 mm collimated beam from the light source is reflected perpendicularly from reflective surface M1 1008 through a sample cuvette holder (i.e., the sample chamber 1010). In this example, the entrance aperture of the sample chamber 1010 has a 9 mm diameter. The sample chamber 1010 may contain a sample in a liquid medium and may have a width of 10 mm perpendicular to the beam and a length parallel to the beam of 2 mm.

In one example, the sample chamber 1010 may be filled with approximately 1 ml of liquid so the full 8 mm beam passes through the sample. The residual collimated beam and the light scattered off the sample may then reflected perpendicularly off of reflective surface M2 1012 and exits to the next section of the optical path.

Lens 1006 may collimate the light and L2 1014 may focus the light on the deformable mirror 1024. Collimated light from the sample chamber 1010 may be incident on lens L1 1006. Lenses L1 (e.g., f1=75 mm) and L2 (e.g., f2=30 mm) may be separated by a distance D12=f1+f2=105 mm. In this example, the light leaving lens L2 1014 is collimated with a beam size of 3.2 mm. The collimated beam is incident on a BMC MEMS deformable mirror 1024 composed of, in this example, an equal spaced, 12×12 actuator grid array, where each actuator is separated by 400 microns.

The deformable mirror 1024 may, in some embodiment, may control the wave front of the light based on information received from the wave front sensor 1030. In this example, the light may magnify and/or enhance the light of the optical path. Control of the deformable mirror 1024 may allow for control of the wave front of the light to direct a flat wave front to the detector 1032. It will be appreciated that, in some examples, the optical path 1000 may not have a deformable mirror 1024. In that case, the optical path 1000 may not have a beam splitter or a wave front sensor WFS 1030.

Light then is further focused by lens 1018 on the vortex mask 1016. The vortex coronagraph 1016 may be created by first constructing a 4f beam relay using 2 matching 75 mm lenses, L3 (f3=75 mm) and L4 (f4=75 mm). Lens L3 1018 may be placed a distance equal to the focal length of lens L3 away from the DM (D3=75 mm). Lens L3 1018 and L4 1022 may be separated by a distance D34=f3+f4=150 mm.

In some embodiments, a collection of monochromatic vortex masks (VM) matched to the input laser diodes are loaded into a filter wheel and placed in the focal plane between L3 1018 and L4 1022. The filter wheel may be mounted to a 3-axis translation stage to provide fine position control for vortex mask alignment. In various embodiments (e.g., any of examples depicted in FIGS. 10A-C), the irradiance at the entrance of the vortex mask may be 34 micrometers.

Lens L4 1022 may be a collimator lens and/or may focus the light on the Lyot stop 1020. In this example, a Lyot stop (LS) 1020 is place after lens L4 1022 at a distance of D4=75 mm. Different Lyot stop 1020 sizes may be used. In one example, a lyot stop 1020 uses a 0.8×Dpupil~=2.56 mm aperture.

The Lyot stop 1020 may be a lyot-mask (e.g., lyot stop) such as a Lyot-plane phase mask, which enables improved contrast performance. The Lyot-plane phase mask may relocate residual light away from a region of the image plane, thereby reducing light noise from the sources of the spectrometer and improves sensitivity to off-axis scattered light.

In between lens L4 1022 and the Lyot Stop (LS) 1020 a 92/8 beam splitter (BS) is placed in the beam, the 8% reflection is passed into a Shack-Hartmann wavefront sensor (WFS) 1030 which is also a distance D4=75 mm after lens L4 1022.

The WFS 1030 may measure the wave front of the light and control the deformable mirror to flatten the wavefront on the vortex mask 1016 (otherwise signature artifacts may be created).

It may be appreciated that the system may be configured for broadband use by replacing the monochromatic vortex masks with broadband masks that are matched to the new set of narrowband filters in the detector optics.

The residual light that exits the Lyot stop 1020 is passed through a circular polarization analyzer (P2) 1040 that is matched to the circular polarizer 1038 in the light source system. The light may then passed through a Filter wheel with 10 nm narrowband pass filters (NBF) 1042 which may have central wavelengths that are matched to the laser diode sources. The residual light may then be focused onto a detector by lens L5 1026 (e.g., f5=7.5 mm). it may be appreciated that the high contrast (>10-4) performance of the light suppression will be limited by the polarization purity of the beam, so care may be taken to maximize polarization purity.

In some embodiments, a linear array may be used if white light is instead used. In this case the detector is replaced with a fiber mounted multi-mode fiber with a fiber core size greater than 10 microns (Typical use is 400 microns). When setup in the white light configuration, the narrowband filters may be setup to have the same bandpass as the broadband The detector 1032 detects spectral components (e.g., intensities of received wavelengths). In various embodiments, the detector 1032 is part of a spectrometer, a photodiode, or an LCD camera. The detector may generate measurements indicating intensities of wavelengths from the incoherent light of the optical path. The detector may provide absorption r transmittance measurements related to the particles and components of the breath sample.

In one example, the detector 1032 is in communication with a processor to assess and generate the measurement results. The measurement results may then be used to identify if the patron that produced the breath sample is infected.

The measurement results may be received by a discriminator. A discriminator may categorize or determine if the patron is infected by assessing and/or analyzing the measurement results. The discriminator may assess the measurement results using a logistic regression technique, an AI approach (e.g., convolutional neural network), and/or other statistical methods. In some embodiments, the measurement results may be used to create and/or train the discriminator.

FIG. 10C is another example of an optical path of a spectrometer in some embodiments. In the example described with regarding to FIG. 10C, each component will include a location measured directly to the previous component along the optical path (in the direction against incoming light) and another location measured directly along the optical path to the entrance aperture (e.g., the detector may be 1239.257 mm along the optical path from the entrance aperture 1050). These locations are by way of example. It will be appreciated that the components may be located in many different positions relative to each other, the entrance aperture, and/or the light source.

The path may include an entrance aperture 1050. The entrance aperture 1050 may have a beam aperture. For example, the entrance aperture 1050 may accommodate a beam diameter of 6 mm for a beam of wavelength 635 nm. It may be appreciated that the entrance aperture 1050 may accommodate a beam diameter of any size (e.g., between 4-8 mm) and at any wavelength (e.g., 592 nm-700 nm). The entrance aperture 1050 may be any distance from the light source (e.g., 30 mm).

The polarizer 1052 may be made of any material, such as calcite. The polarizer 1052 may be 63.9463 mm from the light source and 30 mm along the light path to the entrance aperture 1050. The polarizer 1052 may polarize light from the light source received via the entrance aperture 1050.

The quarter wave plate (QWP) 1054 may reflect light received from the polarizer 1052 to the cuvette 1056. The quarter wave plate 1054 may be 99.978 mm from the polarizer 1052 and 93.9463 from the entrance aperture 1050.

The cuvette 1056 may contain a sample from a patient or user that is to be measured. The cuvette may be located 124.1297 mm from the quarter wave plate 1054 and 193.9243 mm from the entrance aperture 1050.

The quarter wave plate 1058 may receive light received from through the cuvette 1056 and may reflect all or part of the light to lens 1060.

Lens 1060 may receive light from the quarter wave plate 1058 and allow the light to pass to the lens 1062. The lens 1060 may include, for example, a first side surface radius of curvature 108.07 mm and the other surface (the second side) may be plano. In this example, the lens 1060 may have a thickness of 10 mm and be made of a material such as N-Bk7. It will be appreciated that the surface radius of curvature may be many different sizes (e.g., 90 to 120 mm), the other surface may be plano or curved, the lens 1060 may have any different thickness (e.g., 8-12 mm), and be made of any material or combination of materials. The lens 1060 may be 318.28 mm from the cuvette 1056 or the quarter wave plate 1058. The lens 1060 may be 318.054 from the entrance aperture 1050.

Lens 1062 may receive light from the lens 1060 and allow the light to pass to the deformable mirror 1064. The lens 1062 may include, for example, a first side being plano and a second side having a surface radius of curvature −57.64 mm. In this example, the lens 1062 may have a thickness of 10 mm and be made of a material such as N-Bk7. It will be appreciated that the surface radius of curvature may be many different sizes (e.g., −45 to −75 mm), the other surface may be plano or curved, the lens 1062 may have any different thickness (e.g., 8-12 mm), and be made of any material or combination of materials. The lens 1062 may be 93.9994 mm from the lens 1060. The lens 1062 may be 636.582 mm from the entrance aperture 1050.

Deformable mirror 1064 may receive light from the lens 1062 and project the light to the lens 1066. The deformable mirror 1064 may be 78.834 mm from the lens 1062 and may be 760.5814 mm from the entrance aperture 1050.

Lens 1066 may receive light from the deformable mirror 1064 and allow the light to pass to the vortex mask 1068. The lens 1066 may include, for example, a first side having a surface radius of curvature 38.6 mm and a second side being plano. In this example, the lens 1066 may have a thickness of 10 mm and be made of a material such as N-Bk7. It will be appreciated that the surface radius of curvature may be many different sizes (e.g., 25 to 55 mm), the other surface may be plano or curved, the lens 1066 may have any different thickness (e.g., 8-12 mm), and be made of any material or combination of materials. The lens 1066 may be 76.3095 mm from deformable mirror 1064. The lens 1066 may be 805.4154 mm from the entrance aperture 1050.

Figure 12:
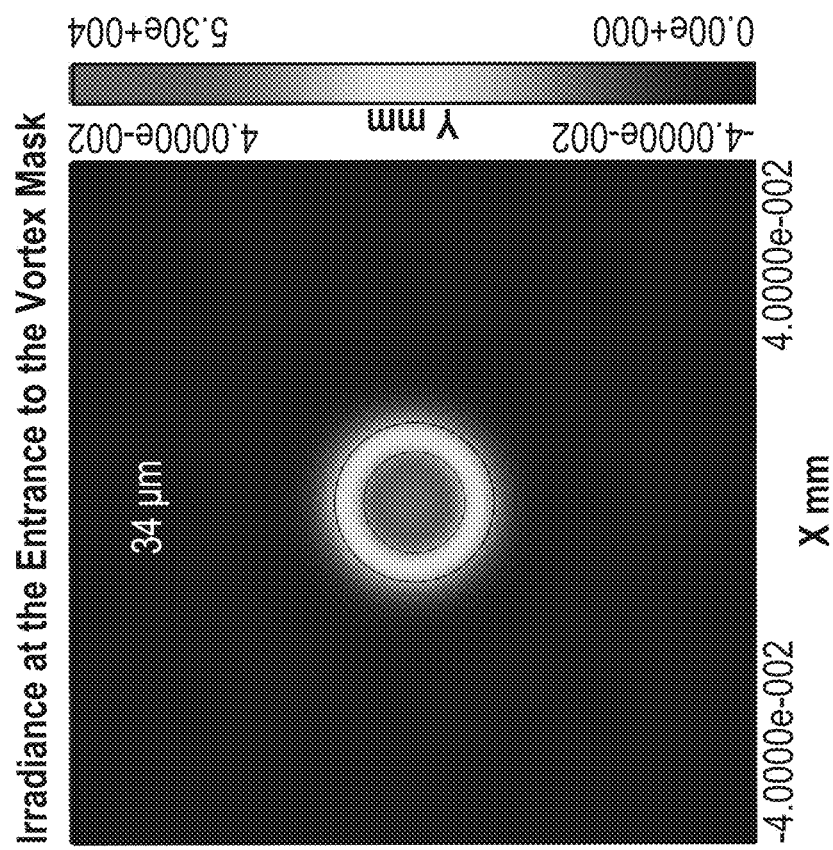
FIG. 12 depicts the irradiance at the entrance to the vortex mask is 34 micrometers in one example.

The vortex mask 1068 may receive light from the lens 1066 and allow (at least some) of the light to pass to lens 1070. The vortex mask 1068 may be 72.0435 mm from the lens 1066 and may be 881.7249 mm from the entrance aperture 1050. FIG. 12 depicts the irradiance at the entrance to the vortex mask 1068 is 34 micrometers in one example.

Figure 13B:
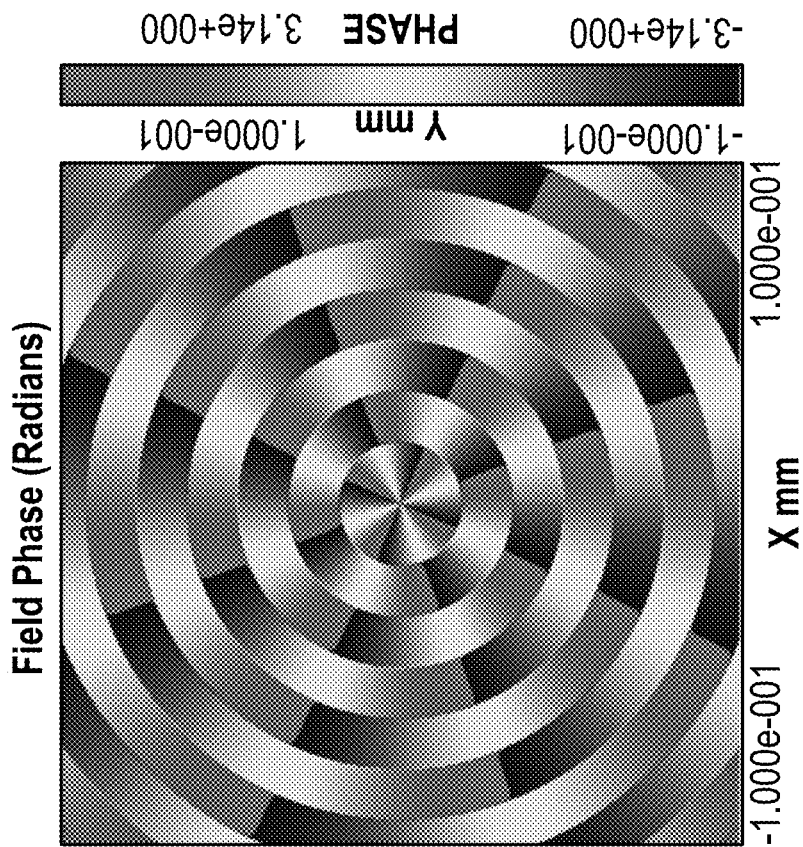
FIG. 13B depicts a field phase (radians) after the vortex mask in some embodiments.
Figure 13A:
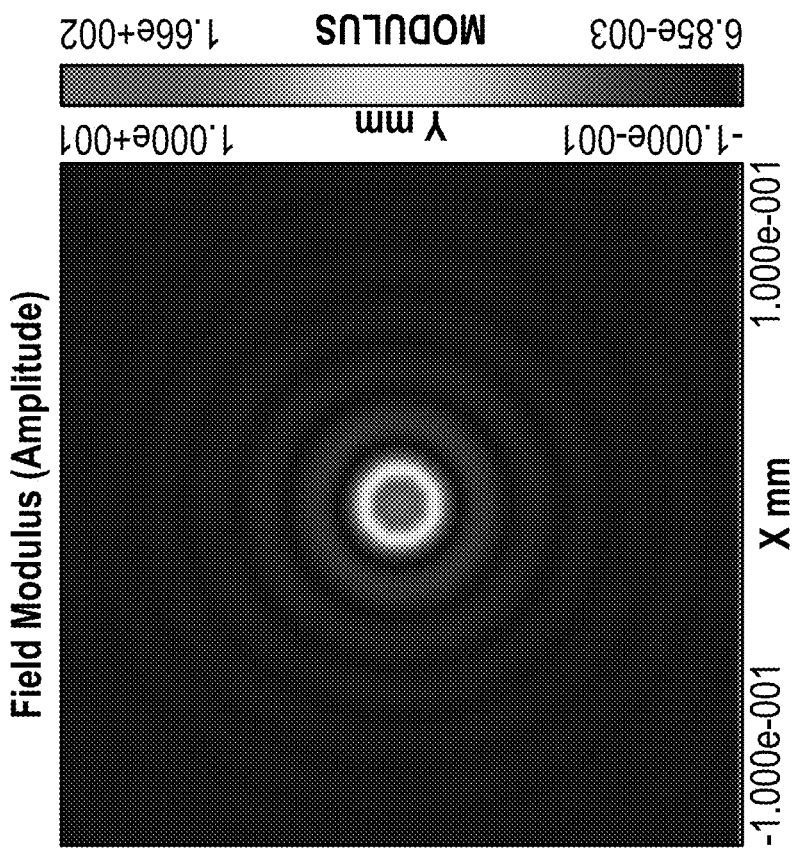
FIG. 13A depicts a field modulus (amplitude) after the vortex mask in some embodiments.

FIGS. 13A and 13B depicts modulus and phase of the field after the vortex mask 1068 in some embodiments. FIG. 13A depicts a field modulus (amplitude) after the vortex mask 1068 in some embodiments. FIG. 13B depicts a field phase (radians) after the vortex mask 1068 in some embodiments.

Lens 1070 may receive light from the vortex mask 1068 and allow the light to pass to the lyot stop 1072. The lens 1070 may include, for example, a first side being plano and a second side having a surface radius of curvature −38.6 mm. In this example, the lens 1070 may have a thickness of 10 mm and be made of a material such as N-Bk7. It will be appreciated that the surface radius of curvature may be many different sizes (e.g., −30 to −45 mm), the other surface may be plano or curved, the lens 1070 may have any different thickness (e.g., 8-12 mm), and be made of any material or combination of materials. The lens 1070 may be 78.934 mm from the vortex mask 1068. The lens 1070 may be 953.7684 mm from the entrance aperture 1050.

The lyot stop 1072 may receive light from the lens 1070 and allow (at least some) of the light to pass to beam splitter 1074. The lyot stop 1072 may be 57.1156 mm from the lens 1070 and may be 1,032.702 mm from the entrance aperture 1050.

Figure 14A:
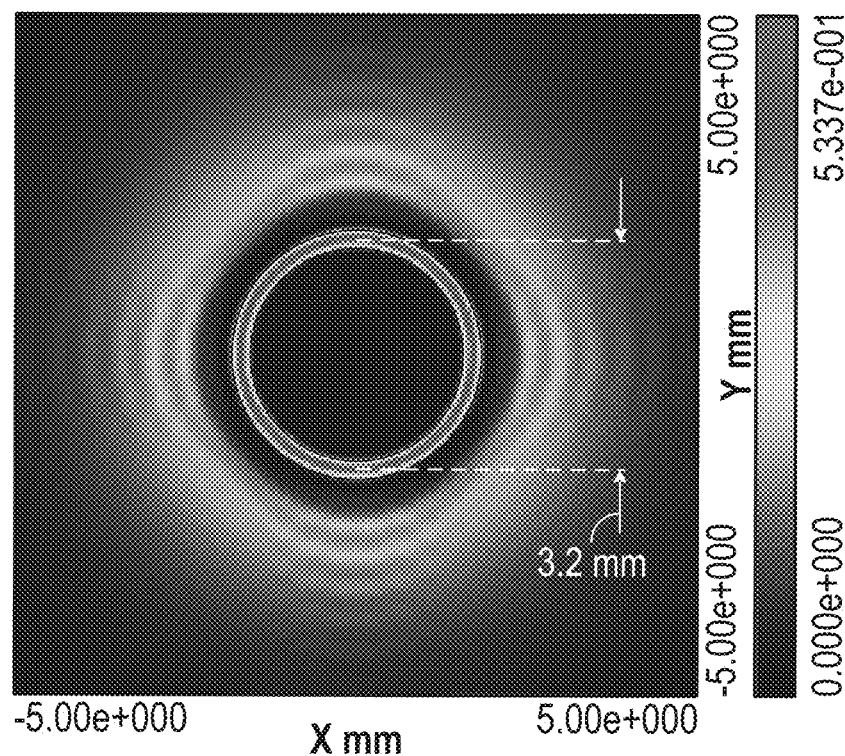
FIG. 14A depicts an example interior irradiance of the lyot stop in one example.
Figure 14B:
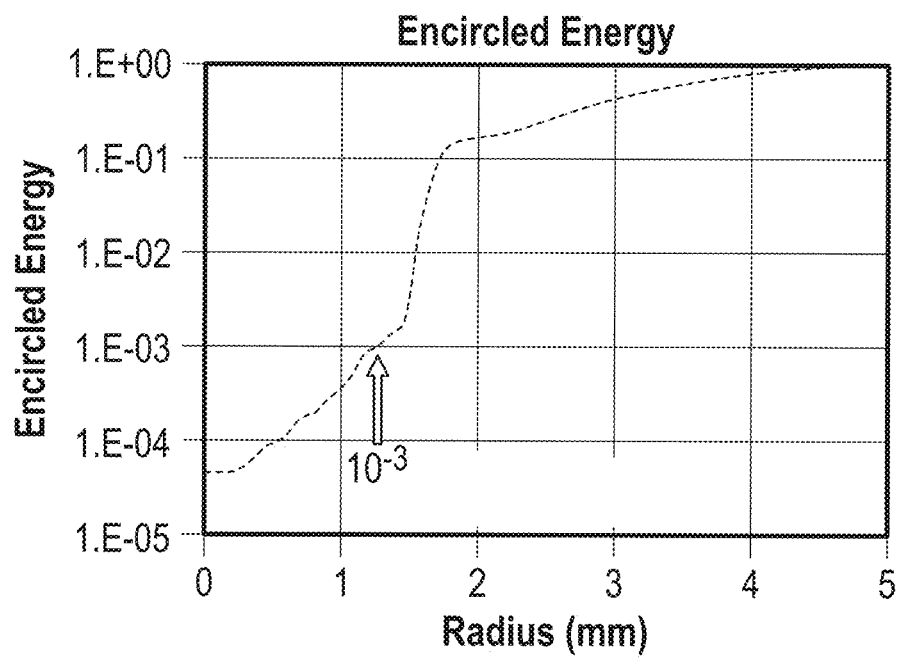
FIG. 14B is a graph indicating a 10-3 contrast for a lyot stop radius of 1.25 mm in one example.

FIGS. 14A and 14B depicts interior irradiance at the lyot stop 1072 in some embodiments. The vortex mask 1068 may produce a "ring of fire" at the lyot stop plane. The interior irradiance may be approximately 10-4 of the ring irradiance and the total power may be, for example, 9.33. FIG. 14A depicts an example interior irradiance of the lyot stop 1072 in one example. FIG. 14B is a graph indicating a 10-3 contrast for a lyot stop radius of 1.25 mm in one example.

The beam splitter 1074 may receive light from lyot stop 1072 and allow (at least some) of the light to pass to polarizer 1076. The beam splitter 1074 may be 68.7634 mm from the lyot stop 1072 and may be 1,089.818 mm from the entrance aperture 1050. The beam splitter 1074 may be configured to measure all or some of the received light, compare the characteristics to criteria or a reference, and control the deformable mirror 1064 to control the light beam.

The polarizer 1076 may receive light from beam splitter 1074 and allow the light to pass to lens 1078. The polarizer 1076 may be 50 mm from the beam splitter 1074 and may be 1,180.581 mm from the entrance aperture 1050.

Lens 1078 may receive light from the polarizer 1076 and allow the light to pass to the detector 1080. The lens 1078 may include, for example, a first side having a surface radius of curvature 8.89 mm and a conic constant of −0.717. The second side may be plano. In this example, the lens 1078 may have a thickness of 2.5 mm and be made of a material such as N-SF11. It will be appreciated that the surface radius of curvature may be many different sizes (e.g., 2-15 mm), the other surface may be plano or curved, the lens 1078 may have any different thickness (e.g., 1-5 mm), and be made of any material or combination of materials. The lens 1078 may be 8.676 mm from the polarizer 1076. The lens 1078 may be 1,230.581 mm from the entrance aperture 1050.

The detector 1080 may receive light from the lens 1078. The detector may be or include a camera such as a CCD. In this example, the detector 1080 may be 1,239.257 mm from the entrance aperture 1050.

In various embodiments, the vortex spectrometer or digital device may perform dark noise correction to reduce noise. Dark noise arises from changes in thermal energy of the spectrometer and/or camera (e.g., detector). The increase of signal also carries a statistical fluctuation known as dark current noise.

As discussed herein, dark noise arises from variation a cross an imaging sensor with no external illumination. Dark noise may be corrected by taking a reference with no illumination, calculating the mean of the dark noise signal, and then subtracting the dark noise off of the sample signal.

Figure 15:
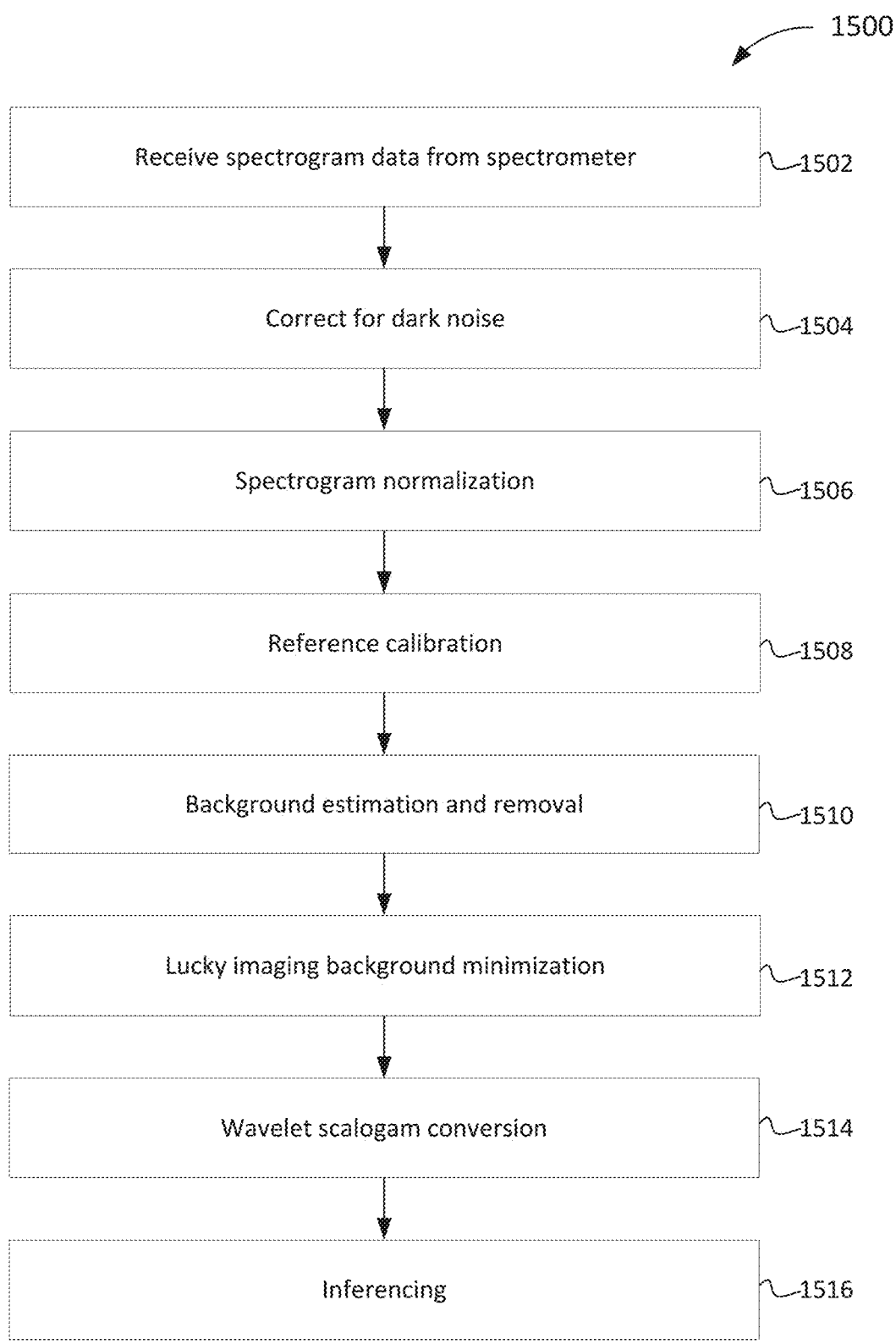
FIG. 15 is a flowchart for identifying infection from spectrometer data in some embodiments.

FIG. 15 is a flowchart 1500 for identifying infection from spectrometer data in some embodiments. In some embodiments, a spectrometer as discussed herein may take measurements of a patient's sample (e.g., saliva, breath, or the like). The measurements may then be analyzed to detect infection. Different viruses may produce different wavelength intensities. As a result, a virus may be associated with a "signature" or "thumbprint" of spectral intensities that may be detected.

In step 1502, a digital device may receive spectrogram data from a spectrometer as discussed herein (e.g., with or without a vortex spectrometer and lyot stop, including, for example, the spectrometer depicted in FIG. 10A, 10B, or 10C). The digital device may be local or remote to the spectrometer that produced the spectrometer results. In one example, the spectrometer may be a health screening system as discussed herein. The digital device may receive raw spectrogram data or spectrogram data after transmission and reconstruction.

In step 1504, the digital device may perform dark noise correction. Optical experiments are made variable by imperfections in the light source, transmission of the optical path, and possibly wavelength-specific non-idealities in the detector. For each sample measured, a spectrometer may be configured to collect multiple references (e.g., two) references which control for variance in the environment in which the spectrometer is placed, and in the measurement hardware. Data collected in a reference frame, TR, together with the dark frame TD and the collected sample TS, allows the formation of the attenuance:

$$\mu = (T_S - T_D)/(T_R - T_D)$$

In one example, raw transmission spectra may be collected during a single 100 μs acquisition for the purpose of calibrating measurement response. In this example, two references are collected: 1) a dark frame which is acquired with the light-source for the detector turned off and 2) a reference collected with a cuvette for the sample in place and filled with DI water, the diluent used in the assay. The dark frame allows for the subtraction of environment noise due to imperfect isolation of the interaction medium and sample during measurement. The reference utilized in order to measure the attenuation due to the presence of the cuvette and diluent medium, and to form the absorbance according to −TS/TR.

The attenuance is a physical property of the analyte which does not depend on the variable aspects of the measurement. To ensure good correspondence between the measured sample attenuation and the physical value, the assay may specify a collection of the reference frame immediately before collection of the data from the clinical sample or analyte.

Measurements of dark noise may be made using digital numbers. Digital numbers are assigned to a pixel in the form of a binary integer, often in the range of 0-255 (a byte). A single pixel may have several digital number variables corresponding to different bands recorded.

Figure 16A:
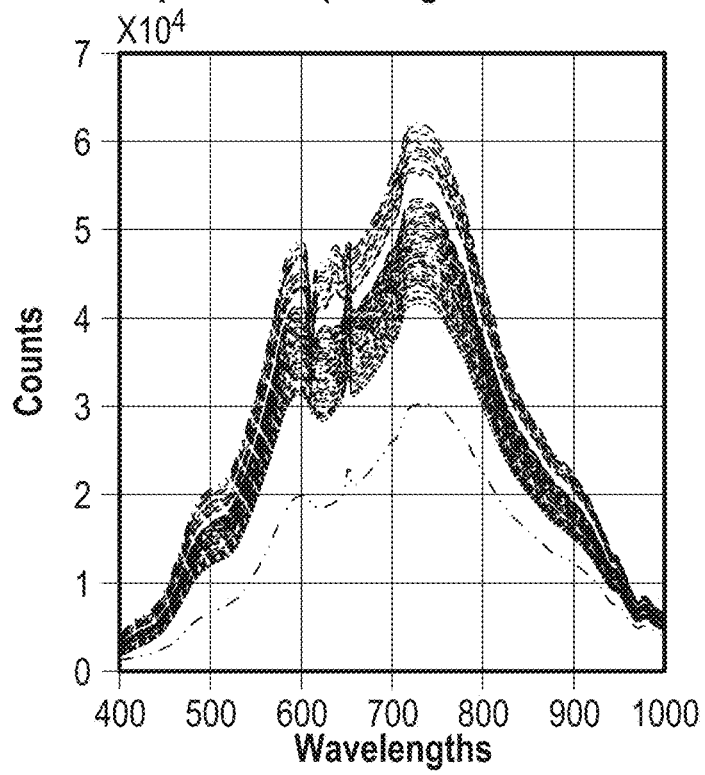
FIG. 16A depicts a test spectra in one example.
Figure 16B:
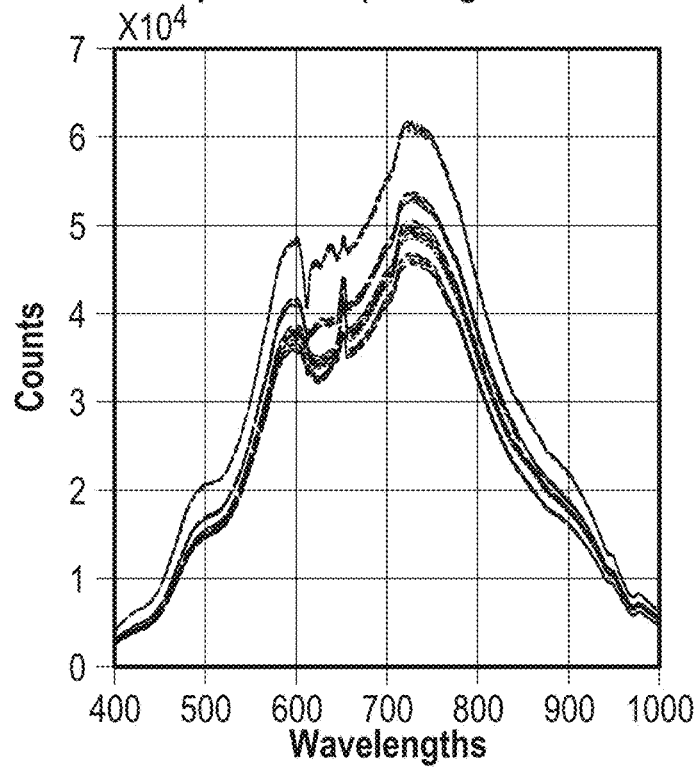
FIG. 16B depicts a reference spectra in one example.
Figure 16C:
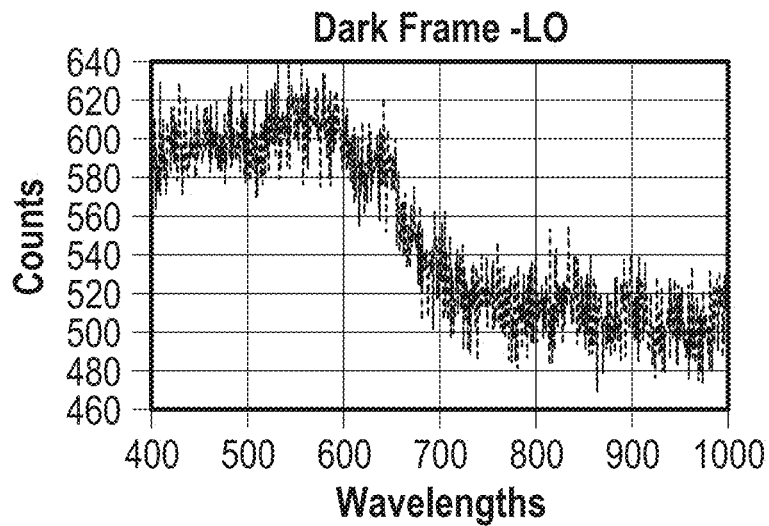
FIG. 16C depicts the mean value of the dark noise in one example.

FIG. 16A depicts a test spectra and FIG. 16B depicts a reference spectra in two examples. Here, the shape of the spectra is observed, and the signal may be, in this example, about 60,000 digital numbers. The resulting dark noise in comparing the reference to the test has a mean value of about 600 digital numbers. FIG. 16C depicts the mean value of the dark noise in one example.

It will be appreciated that the dark noise for a particular spectrometer may not change. As a result, the spectrometer may be tested in a factory to identify dark noise and then a dark noise correction may be applied to spectrogram data throughout the day or going forward. In some embodiments, the spectrometer may be tested daily or at some other periods of time, and then the dark noise detected during testing may be used to correct spectrogram data.

In various embodiments, the dark noise caused by the spectrometer may be filtered from the data. By identifying dark noise and filtering the dark noise from the spectrometer data, the signal (e.g., meaningful spectral intensities) may be boosted.

In various embodiments, the dark noise of a particular spectrometer may be measured. This may be done by letting the spectrometer warm up and measuring water and/or a common transport medium. Noise caused by thermal changes may be detected by the detector (e.g., by a CCD camera). Multiple measurements may be taken (e.g., at the same time or over time) and the dark noise may be averaged, aggregated, and/or otherwise collected.

Figure 16D:
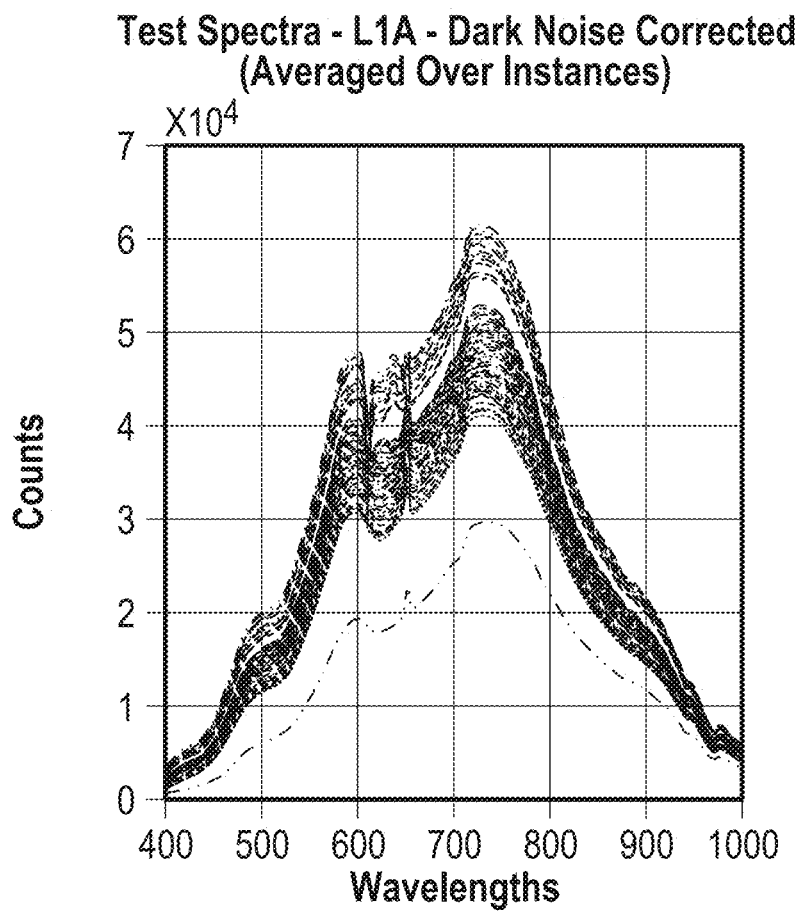
FIG. 16D depicts a test spectra of dark noise corrected in one example.
Figure 16E:
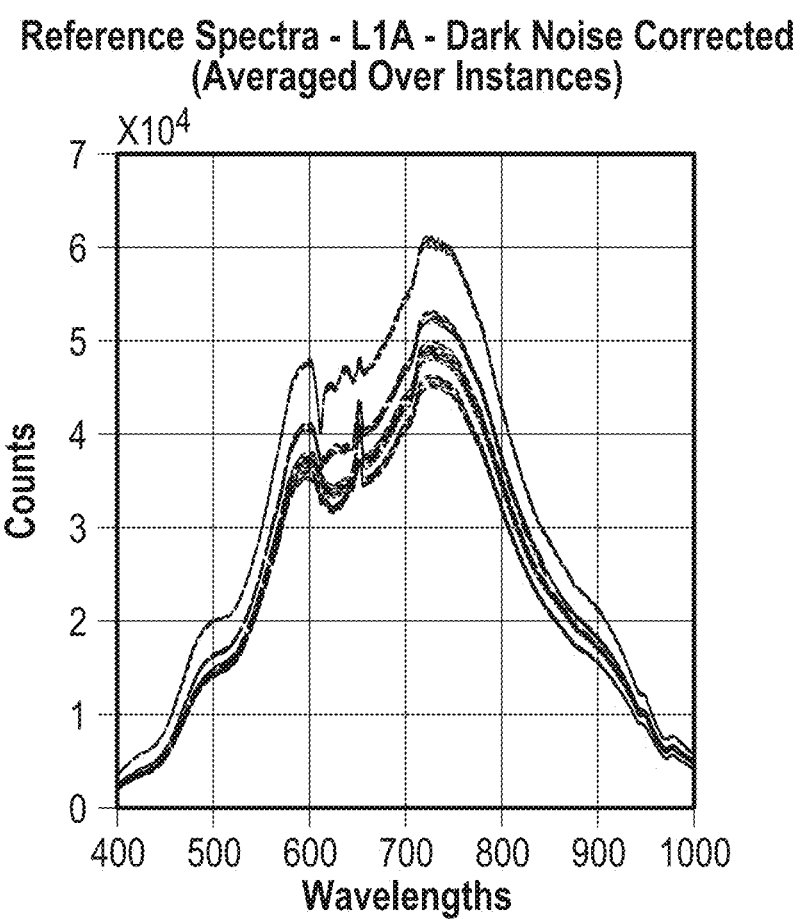
FIG. 16E depicts a reference spectra of dark noise corrected in one example.

FIG. 16D depicts a test spectra of dark noise corrected in one example. FIG. 16E depicts a reference spectra of dark noise corrected in one example.

In step 1506, the digital device performs spectrogram normalization. Variations from sample to sample may create issues. In some embodiments, an autoexposure is used. For example, the digital device and/or the spectrometer may take an image of the spectral intensities and determine location in a fixed integration of time and determine the integration time to get to a desired measurement (e.g., 60,000 digital numbers).

In some embodiments, reference data may be taken (e.g., by using the spectrometer on water or VTM) and a location of a peak intensity identified. The digital device may scale the spectral intensities from that wavelength. The reference information may be taken using water or a VTM to determine peak intensity. The reference may be taken at the factory, once a day, or at any time.

This correction may assist flat fielding of the CCD camera where some pixels are not as sensitive as other pixels in the CCD camera (which as a result, may detect information that is not caused by differences in intensity but rather differences in chip sensitivities).

For example, a determination of where a peak occurs in the reference may be performed. Then all references may be scaled to that peak intensity.

Figure 17B:
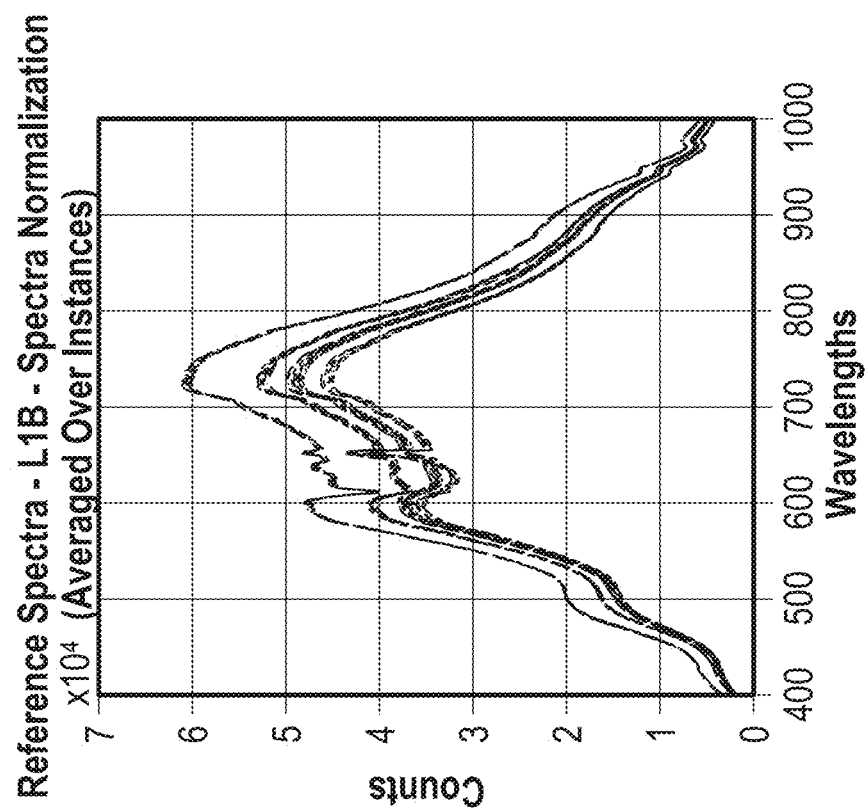
FIG. 17B depicts an example reference spectra including spectra normalization averaged over instances.
Figure 17A:
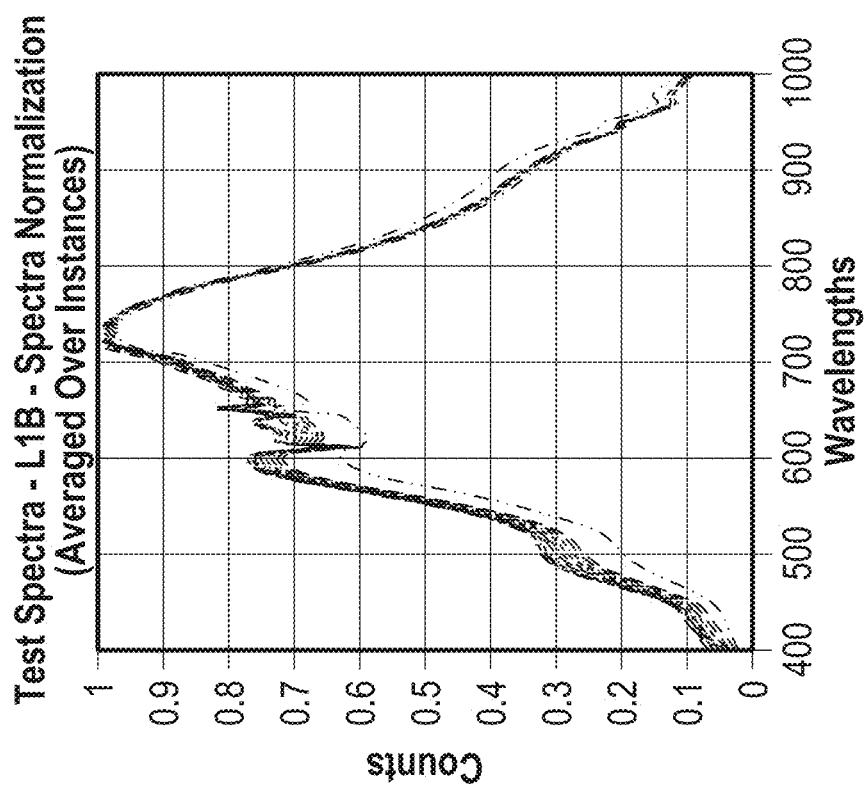
FIG. 17A depicts an example test spectra including spectra normalization averaged over instances.

FIG. 17A depicts an example test spectra including spectra normalization averaged over instances. FIG. 17B depicts an example reference spectra including spectra normalization averaged over instances.

Figure 17D:
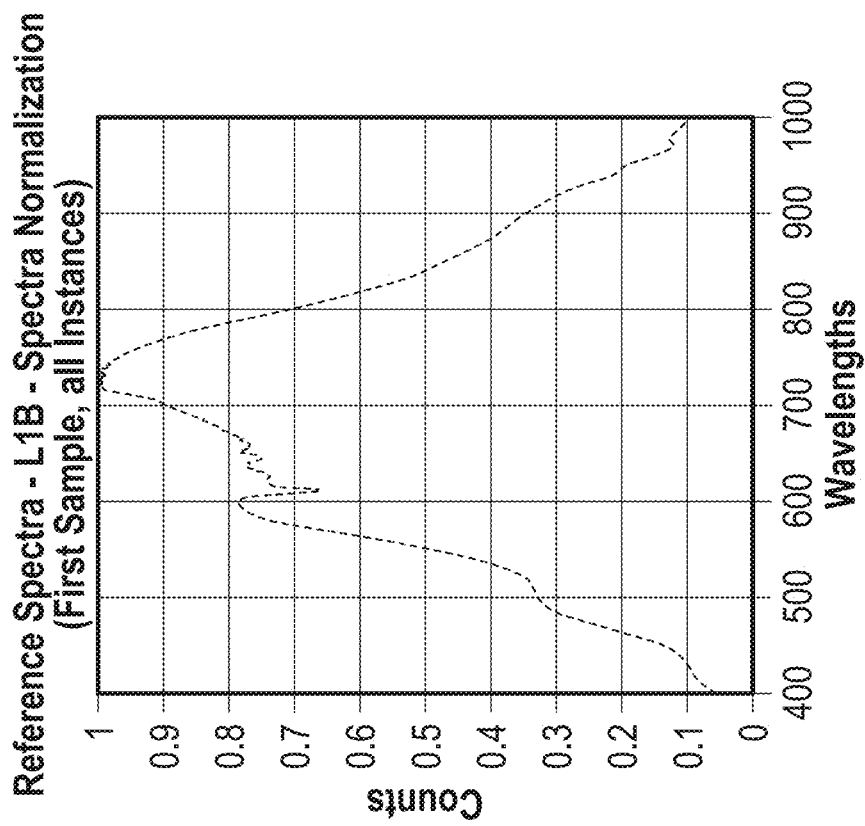
FIG. 17D depicts an example reference spectra including spectra normalization for the first sample, all instances.
Figure 17C:
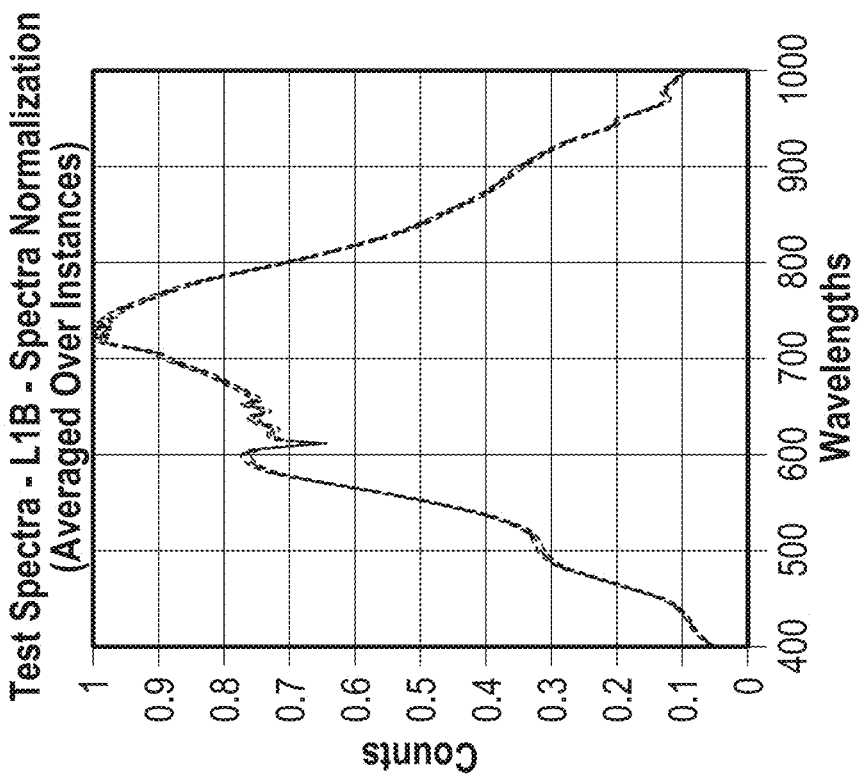
FIG. 17C depicts a test spectra with spectra normalization for the first sample, all instances.

FIG. 17C depicts a test spectra with spectra normalization for the first sample, all instances. FIG. 17D depicts an example reference spectra including spectra normalization for the first sample, all instances.

In step 1508, the digital device performs reference calibration. In one example, the digital device takes the ratio of the reference to the signal and then subtracts the reference. The curve may be characteristic of the substance. A flat line would indicate no information.

Figure 18A:
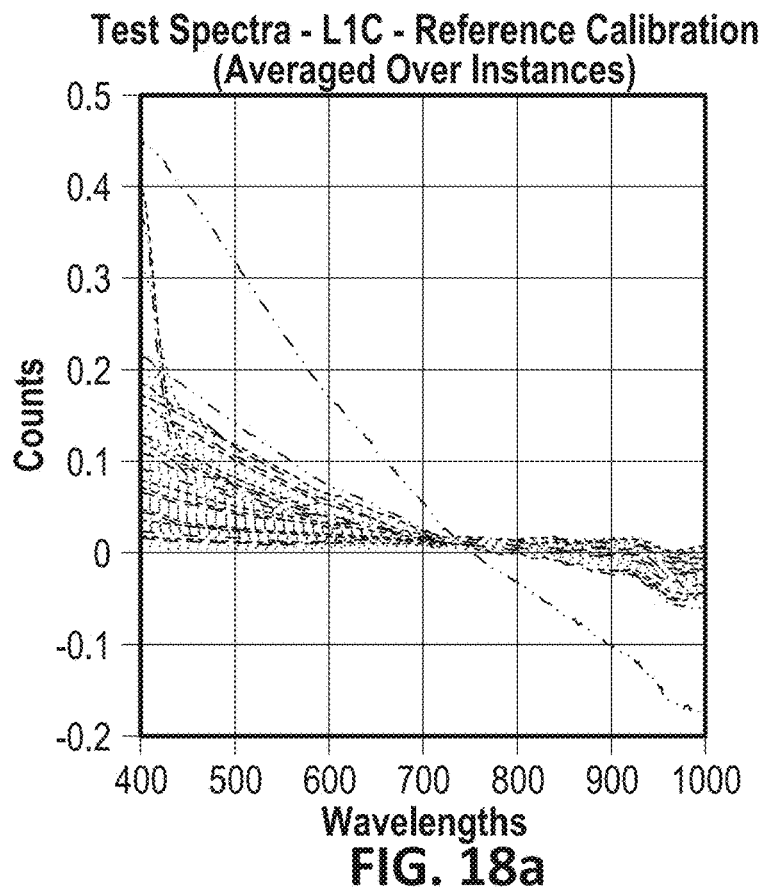
FIG. 18A depicts an example test spectra including spectra normalization averaged over instances.
Figure 18B:
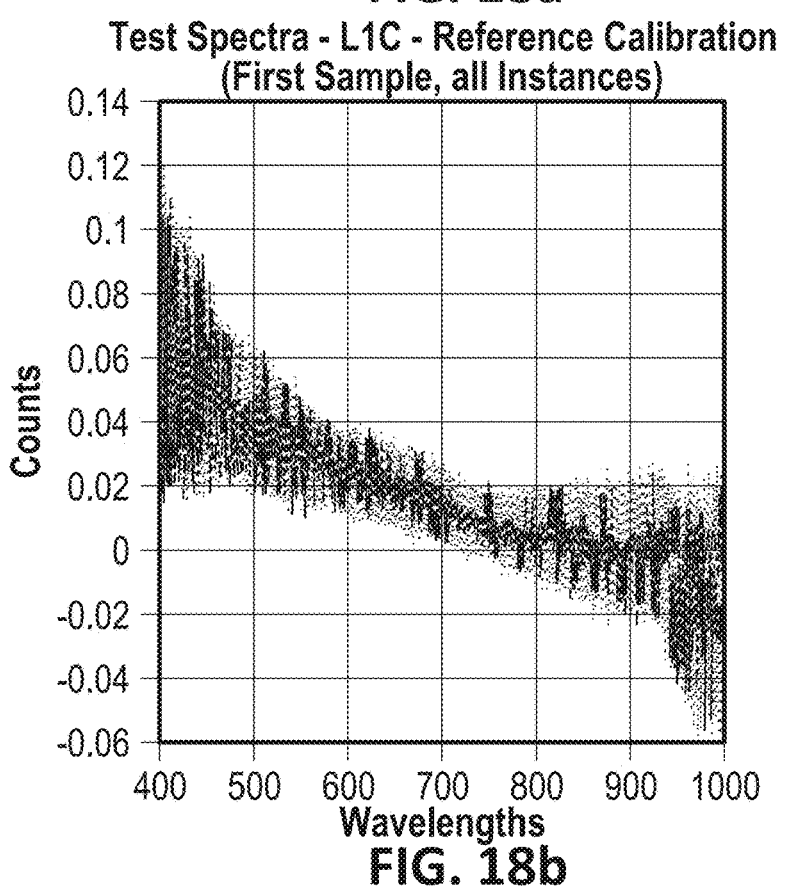
FIG. 18B depicts an example reference spectra including spectra normalization averaged over instances.

FIG. 18A depicts an example test spectra including spectra normalization averaged over instances. FIG. 18B depicts an example reference spectra including spectra normalization averaged over instances.

In step 1510, the digital device performs background removal and estimation. In one example, the digital device takes the ratio of the reference to the signal and then subtracts the reference.

It will be appreciated that samples are often more negative (uninfected) then positive. For example, the positive rate may be only 5% or less of all samples (e.g., 20 times more negatives than positives). In various embodiments, a background pool is created. Negative results may be clustered into families.

In various embodiments, the digital device groups results according to similarities. For example, the digital device may select two negative results and subtract them to get a minimum energy which may be used for a characteristic curve. In some embodiments, measurements of any number of samples may be divided into levels (e.g., based on similarities and/or measurements). There may be any number of levels. For example, similarities or measurements may be ordered or ranked based on intensity, energy, and/or wavelength. The ordered or ranked information may be divided into sets based on equal or unequal thresholds.

Each of the measurements or sets may be compared to each other and a minimum may be taken to get characteristics for each level. A pool of negatives (compare positive to negative) may be obtained. A pool of negatives refers to a collection of negative results (e.g., no infection indicated) as opposed to positive results (e.g., infection indicated).

The result may be assessed to determine the curve. A flat line, for example, may contain no information while a curve may indicate information related to virus infection. The digital device may remove the background from future signals/measurements to remove the background signature of saliva and VTM itself. The background pool of information may also be determined and minimized to find the minimum energy.

Figure 19A:
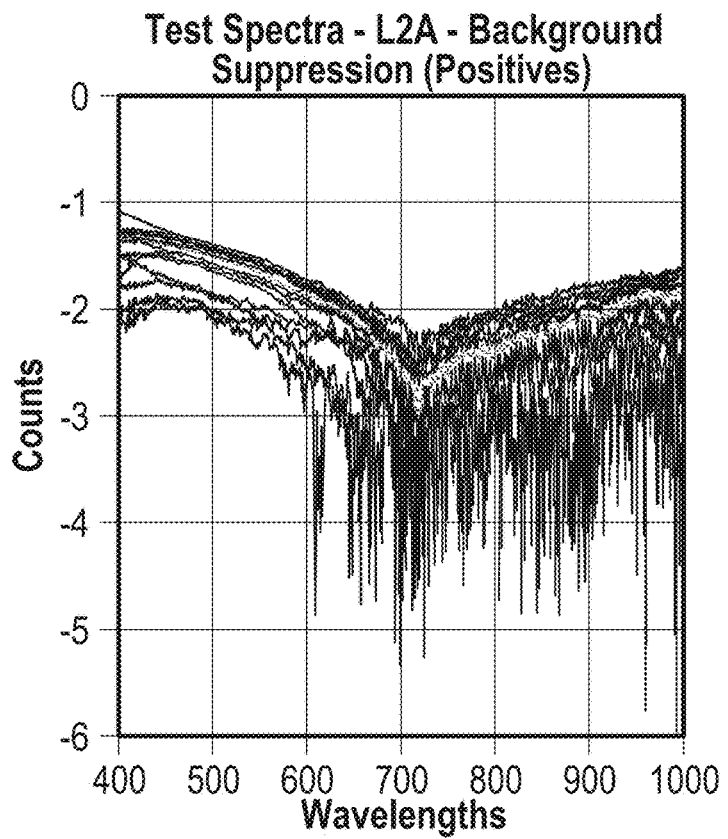
FIG. 19A depicts an example test spectra of positive (infection) results with background suppression.
Figure 19B:
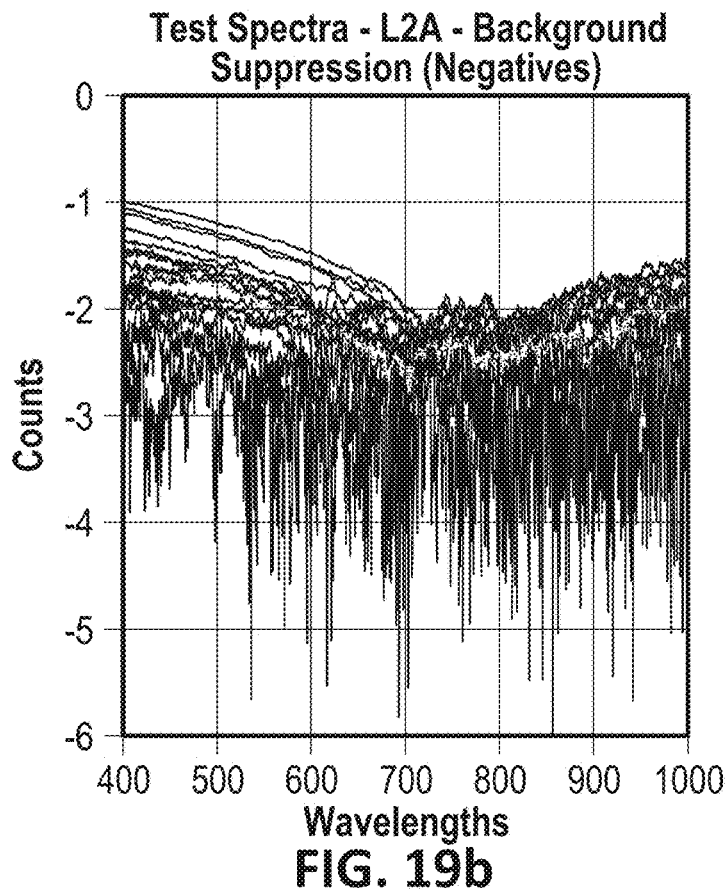
FIG. 19B depicts an example test spectra of negative (infection) results with background suppression.

FIG. 19A depicts an example test spectra of positive (infection) results with background suppression. FIG. 19B depicts an example test spectra of negative (infection) results with background suppression.

Figure 19C:
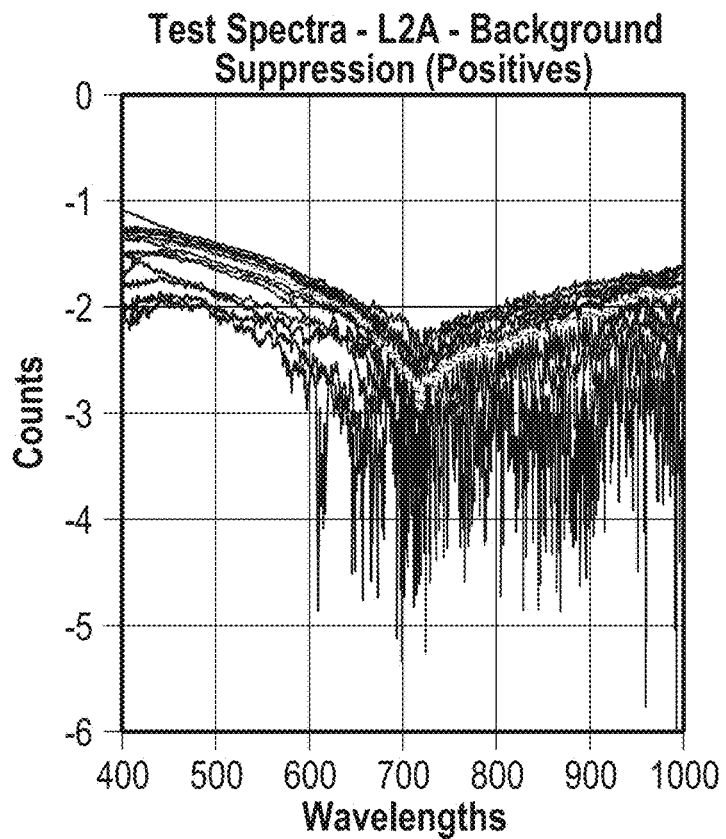
FIG. 19C depicts an example test spectra of positive (infection) results with background suppression.
Figure 19D:
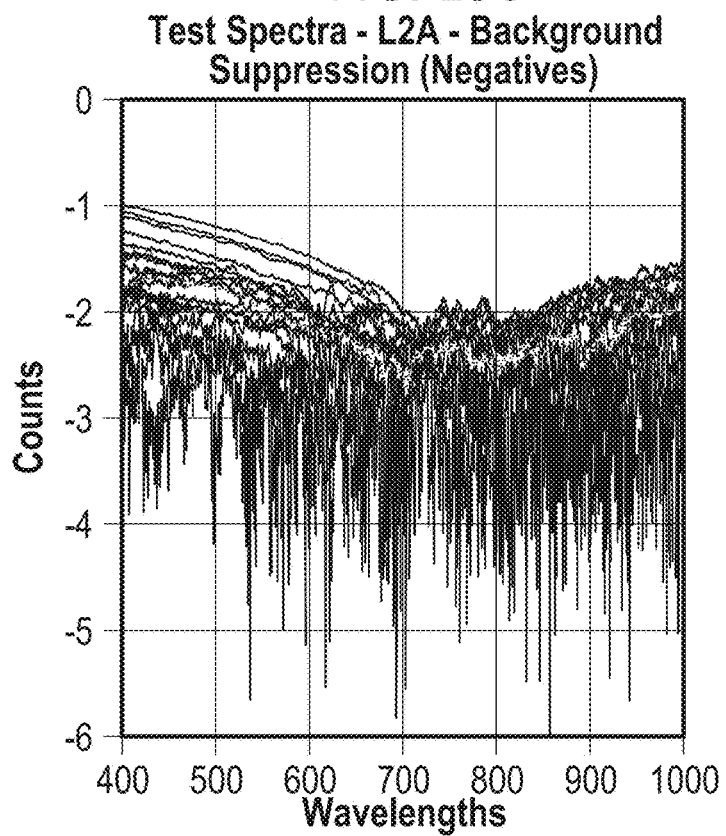
FIG. 19D depicts an example test spectra of negative (infection) results with background suppression.

FIG. 19C depicts an example test spectra of positive (infection) results with background suppression. FIG. 19D depicts an example test spectra of negative (infection) results with background suppression.

In step 1512, the digital device may perform lucky imaging background minimization. In various embodiments, the digital device and/or spectrometer may make many measurements of a sample. The digital device may assess the different samples to identify the sample that provides the most energy. For example, the digital device may perform background estimation and removal from any number of images (e.g., all or a subset) to identify the results that express the most information or an indication of a positive or negative result.

In step 1514, the digital device may perform wavelet scalogram conversion. In various embodiments, the digital device performs a wavelet decomposition. A wavelet may be selected and a cross correlation performed along the signal to measure intensities (e.g., weight on left of graph and wavelength along the X axis).

With background estimation, the difference between negatives and positives can be depicted. Intensity variations appear in high frequency wavelets which may indicate a spectral signature for infection (e.g., coronavirus) in step 1516.

Figure 20A:
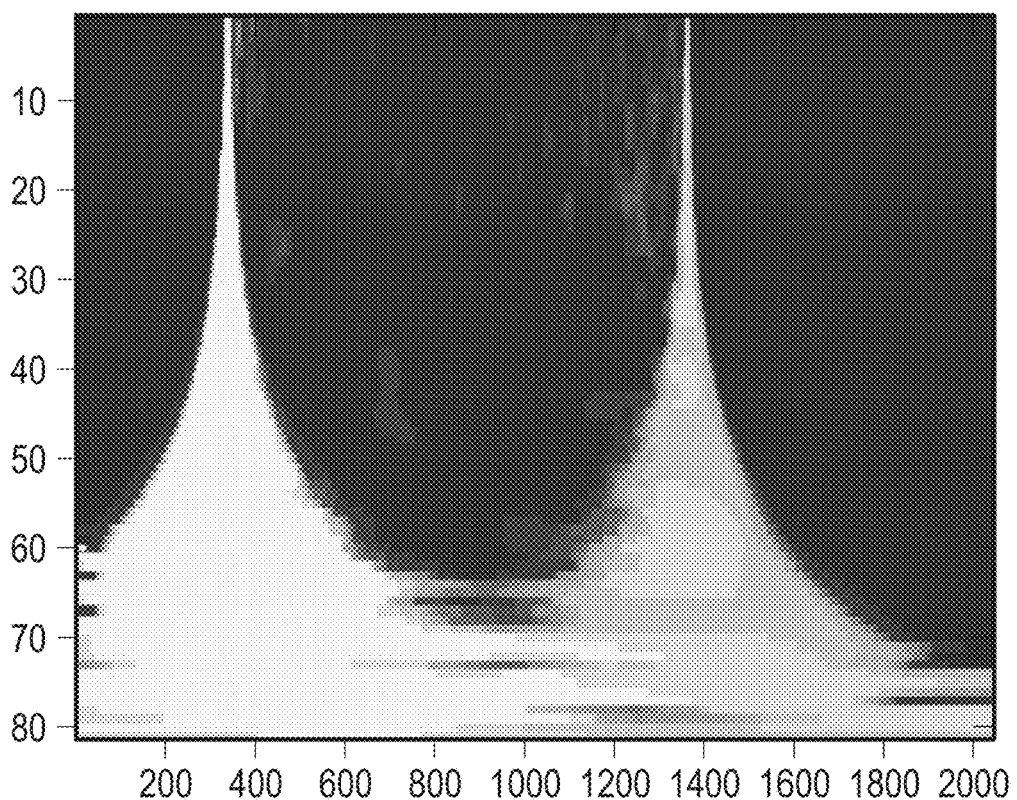
FIG. 20A depicts a negative result scalogram conversion after wavelet correlation.
Figure 20B:
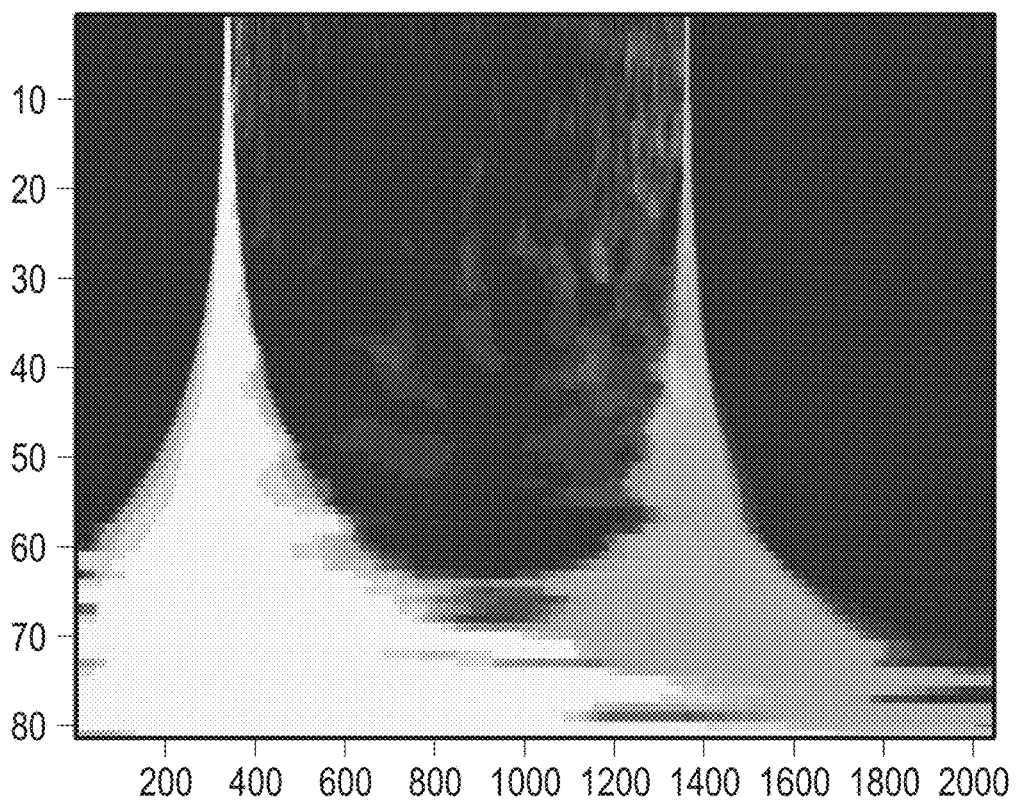
FIG. 20B depicts a positive result scalogram conversion after wavelet correlation.
Figure 20C:
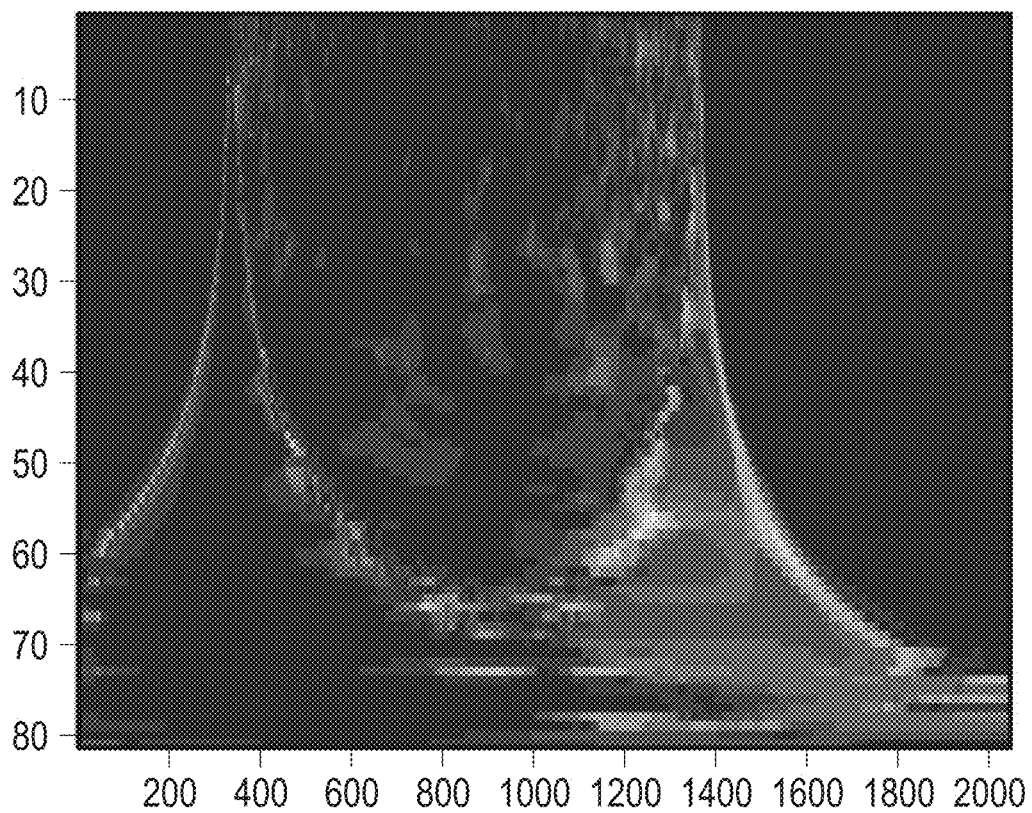
FIG. 20C depicts a difference between the positive and negative result scalogram conversion depicting the difference and indicating the signature of infection.

FIG. 20A depicts a negative result scalogram conversion after wavelet correlation. FIG. 20B depicts a positive result scalogram conversion after wavelet correlation. FIG. 20C depicts a difference between the positive and negative result scalogram conversion depicting the difference and indicating the signature of infection.

In various embodiments, the digital device may perform scalogram conversion after background removal to identify if the signature (e.g., intensities of absorption lines associated with a particular infection, virus-related protein, or virus) or pattern is present. In various embodiments, the digital device may perform the inverse wavelength transform.

Variations from sample to sample may create issues. In some embodiments, an autoexposure is used. For example, the digital device and/or the spectrometer may take an image of the spectral intensities and determine location in a fixed integration of time and determine the integration time to get to a desired measurement (e.g., 60,000 digital numbers).

Figure 21:
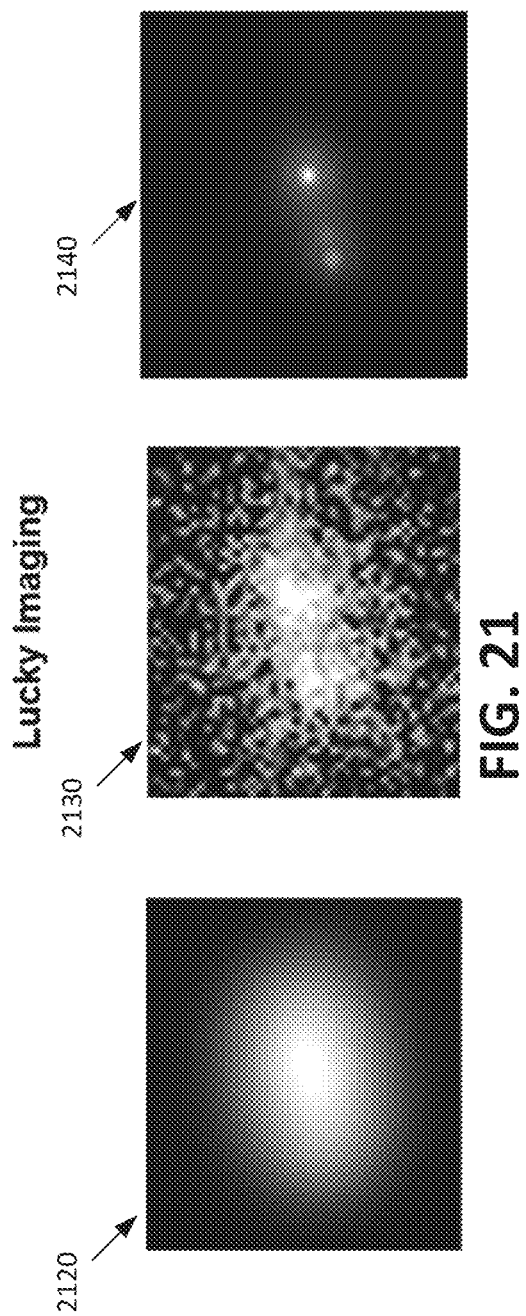
FIG. 21 depicts examples of lucky imaging in some embodiments

FIG. 21 depicts examples of lucky imaging in some embodiments. In various embodiments, the spectrometer with a vortex mask and/or a lyot stop may take multiple measurements of the same sample. The spectrometer or processor may select one or more images contain information most indicative of the presence of the virus (e.g., the spectral signature of the virus) or lack of presence of the virus. For example, luck imaging may utilize multiple measurements to select the image with the best relative clarity and accuracy (e.g., images that depict the energy for the wavelengths of interest associated with a virus). FIG. 21 depicts spectrometer output image 2120 which is improved using lucky imaging to rendered image 2130 which is further improved through lucky imaging to image 2140. There may be any number of measurements used for lucky imaging.

Combined with lucky imaging, a signal may be strengthened by processing many spectrogram snapshots together. In one example, multiple snapshots may be taken of the breath sample using a spectrometer with a vortex mask 840 as discussed herein. Lucky imaging enables using multiple measurements to improve clarity, reduce noise, and detect previously faded signals related to virus infection.

In various embodiments, the system described herein detects COVID-19 infections with a tested 87.5% accuracy. The detection and determination may take under 10 milliseconds.

A discriminator may also be used, in some embodiments. The discriminator may receive results from the spectrometer, assess the information, and provide an indication based on the results (e.g., classification of infection or not infected). In one example described herein, scalograms are collected and parts of the scalograms (e.g. the parts associated with the signature of the virus being tested for) may be compared against references or thresholds. Based on the comparison, the discriminator (e.g., classifier) may provide an indication of infection or not infected (or indeterminant).

In other embodiments, a convolutional neural network (CNN) may be used as a discriminator to identify measurements indicating infection and non-infection. In various embodiments, a neural network may be trained using measurements from the vortex spectrometer as discussed herein. The neural network may also be trained using laboratory test results to confirm those patrons that are infected and those that are not infected. The neural network may receive or generate a set of features base on the output (i.e., measurement results) of the vortex spectrometer. The neural network may then be tested to confirm predictions against known infection/noninfection results.

In one example, the neural network may identify wavelength intensities in the ranges of 735 nm 780 nm 810 nm, and 860 nm as being indicative of infection.

It will be appreciated that any discrimination may be utilized to identify infection and noninfected patrons and/or samples. For example, any statistical method, such as logistic regression analysis, may be utilized.

In various embodiments, an algorithm may be utilized to identify spectral wavelengths and/or scalograms associated with specific pathogens or chemicals to be identified. For example, specific approaches may be utilized in conjunction with many samples to create a "fingerprint" of a scalogram or set of spectral wavelengths associated with a specific pathogen. Scalograms and/or spectral wavelengths generated from a patient's sample may be compared to the fingerprint, reference scalogram, and/or reference set of spectral wavelengths to determine infection or likelihood of infection.

It will be appreciated that many different algorithms and/or approaches may be used. For example, a logistic regression may be used, a K-nearest neighbors approach, decision trees, or random forest. In some embodiments, each sample may be divided by the medium of all collection instances, the data is normalized (e.g., mean=0, std=1), and classification is performed using a logistic regression.

In some embodiments, different approaches may be used with different spectrometers and/or depending on what is being tested. For example, a different dataset from a different spectrometer may utilize an approach where each sample may be divided by the medium of all collection instances, the data is normalized (e.g., mean=0, std=1), and classification is performed using a random forest. Another example may utilize a different approach where, for each sample, an average over windows of a predetermined (e.g., 20) consecutive instances is taken, normalization is performed to sample absorption (e.g., (sample-reference)/reference), and classification is performed using a random forest.

Figure 22:
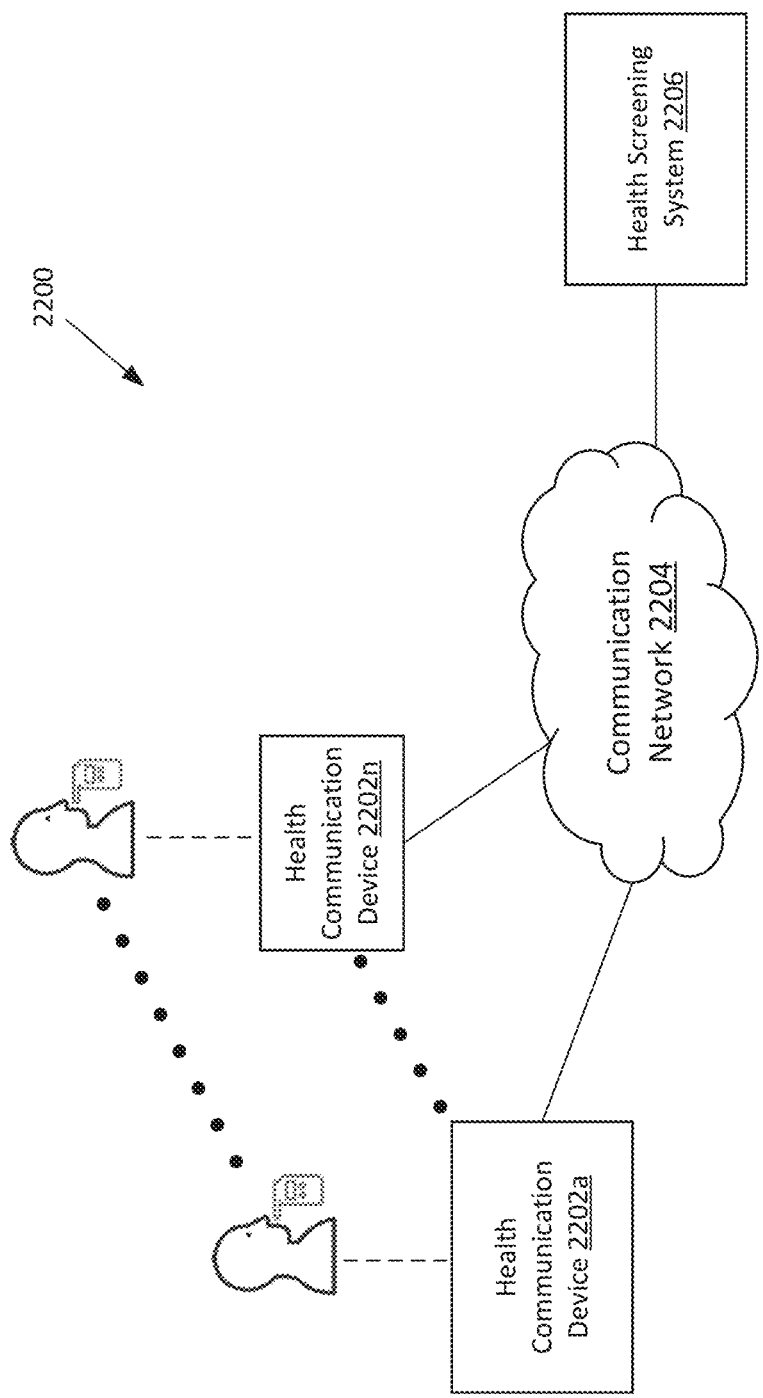
FIG. 22 depicts a health screening environment in some embodiments.

FIG. 22 depicts a health screening environment 2200 in some embodiments. In various embodiments, data and relevant metadata from samples may be sent in realtime after collection to the health screening system. The health screening system 2206 may be a cloud analysis platform. The health screening system 2206 may normalize the data to a common format and suppress noise as discussed herein. These steps may remove spurious features arising from variable aspects of the vortex spectrometer, including variability in total absorption by the sample cuvette.

As discussed herein, the health screening system 2206 may apply dark noise correction. Dark noise arises from variation a cross an imaging sensor with no external illumination. Dark noise may be corrected by taking a reference with no illumination, calculating the mean of the dark noise signal, and then subtracting the dark noise from the sample signal.

The health screening system 2206 may subsequently remove additional background noise. Prior to taking sample data, a reference image may be taken by the vortex spectrometer with a cuvette containing only DI water. The mean of the signal noise is taken and may be subtracted from the sample signal.

As discussed herein, the health screening system 2206 may apply lucky imaging to account for noise that can come from extraneous clutter and fluidic interference within a sample. In one example, the vortex spectrometer may be used to take a time series of readings (e.g., <100 ms) and then combine them to reduce extraneous noise.

The health screening system 2206 may apply matching filters to the de-noised spectral data to determine if a pathogen (e.g., COVID-19) is present.

in some embodiments, the health screening system 2206 may create wavelet difference and cross-spectrum scalograms to enrich a range of spectral feature set data.

The health screening system 2206 may apply discriminator algorithms to further confirm the presence or absence of a pathogen.

It may be appreciated that models may be developed and improved through the different samples from the different health communication devices 2202a-n. Further, models may be reviewed and/or authorized by the proper regulatory authorities.

In various embodiments, the health screening system 2206 may only receive and retain anonymized data. For example, each health screening device 2202a-n (or digital device that is in communication with a health screen device) may anonymize spectral information provided to the health screening system 2206. For example, a digital device in communication with a health screening device 2202 may replace any personally identifiable information of a patient with a unique identifier and/or other anonymous metadata. The spectral information of a patient's sample and the anonymized data may be sent to the health screening system 2206 for analysis. Results (e.g., positive, negative, likely positive, or likely negative) may be provided back to the digital device that provided the spectral information to the health screening system 2206. The digital device may then provide the results back to the patient using the unique identifier and/or metadata. As such, the health screening system 2206 may not receive or store any personally identifiable information but still receive spectral measurements of samples, reference information associated with the spectrometer that took the sample, improve models, and provide models to authorities for approval.

The health screening environment 2200 includes health communication devices 2202a-2202n in communication with a health screening system 2206 over communication network 2204. The health communication devices 2202a-n are any type of digital device that may provide vortex spectrometer measurement results. A vortex spectrometer is any spectrometer with a vortex mask within the optical path.

The health communication devices 2202a-2202n may be, for example, any digital device. A digital device is any device with a processor and memory. In one example, health communication devices 2202a-2202n may include computers in communication with one or more vortex spectrometers. In another example, the health communication devices 2202a-2202n may each be a different vortex spectrometer capable of network communication.

In one example, patrons may each provide a sample. Samples may include exhalation into a breathalyzer, exhalation onto a fogging window, swabs, saliva swabs, or the like. Each of the samples may be placed within one or more vortex spectrometers for testing. The measurements results may be provided over the communication network 2204 to the health screening system 2206. Although the health screening system 2206 may be on a network (e.g., cloud-based), the health screening system 2206 may be on-premises (e.g., local to where the samples were taken or where the vortex spectrometer performed the test).

The health screening system 2206 may receive the measurement results and analyze the results. In various embodiments, the health screening system 2206 may receive many different measurement results from many different vortex spectrometers. The patrons and/or the vortex spectrometers may be geographically remote from each other. The health screening system 2206 may provide centralized testing and return health screening indications (e.g., categories) back to the health communication device that provided the measurement results.

By centralizing the health screening system 2206 on a network, the health screening system 2206 may take advantage of greater processing and memory resources, thereby enabling greater computational efficiency, speed, and scalability. Further, the health screening system 2206 may utilize the measurement results received from many different people and geographically diverse sources to assist with training statistical and/or AI models and curation.

The health screening environment 2200 may assist to perform analysis of epidemics, pandemics, and specific localities of infection. In various embodiments, the digital device in communication with a spectrometer may provide geographic information (e.g., specific location) of the spectrometer and/or areas where the patients work or live (e.g., within zip codes, general locations, or specific locations). The health screening environment 2200 may trace outbreaks and assist in determining seriousness of infection rates and the like. in various embodiments, the digital device in communication with the spectrometer may receive results of the analysis and assist in contact tracing.

As discussed herein, the vortex spectrometer may be utilized to detect pathogens and/or spectral signatures of interest (e.g., to detect substances in food, chemicals, or the like). As discussed herein, when light is passed through a liquid, photons at specific wavelengths may be absorbed by particles in the liquid. The exact wavelengths where absorption occurs depend on the exact chemical composition of the absorbing particles. In this way, a spectrometer can measure the presence of a specific particle if its spectral absorption characteristics are known. The amount of absorption that occurs depends on the number of absorbers that are within the path of the light passing through the test chamber. Therefore, the absorption may also be dynamic if the particles transit the light path due to their motion within the liquid. Particles may be in motion for a variety of reasons including diffusion, convection, settling, and/or the like.

Particles of a substance in motion change the absorption profile dynamically as particles move in and out of a beam path. Consider the case of a spectral characterization of a dynamic absorber in an inert liquid, where the liquid does not contribute to the spectral signature:

$$I_S(\lambda,t) = I_0(\lambda,t) - N_A(t) \cdot I_A(\lambda)$$

Where the light source is assumed to have a dynamic spectral response given by $I_0(\lambda,t)$, $N_A(t)$ is the number of dynamic absorbers of substance A, and substance A has an absorption spectrum given by $I_A(\lambda)$. The light source may vary dynamically for a variety of reasons including shot noise, dark noise, thermal drift, and the like. In many cases this variation may be greater than the absorption signature from substance A. However, these noise variations are derived from different physical processes and have different stochastic characteristics, which we may exploit to differentiate between light source variations and dynamic absorber concentration variations.

Light source variations are random and uncorrelated in time but variations in particle density are not. Particle variations are partially correlated in time and depend on several factors such as: particle size, liquid viscosity, temperature etc.

Consider the auto-correlation of a time series:

$$\text{autocorr}(X,\tau) = \frac{\sum_{i=1}^{n}[X_i - \bar{X}][X_{i-\tau} - \bar{X}]}{\sum_{i=1}^{n}[X_i - \bar{X}]^2}$$

Where the time series is correlated with itself delayed in time by a time lag, $\tau$, there are n discrete time steps and $\bar{X}$ is the mean of the time series. Applying equation 2 to equation 1 and using the fact that the autocorrelation of the sum of two uncorrelated functions is the sum of the autocorrelation of the functions separately yields:

$$\text{autocorr}(I_S(\lambda,t),\tau) = \text{autocorr}(I_0(\lambda,t),\tau) - \text{autocorr}(N_A(t),\tau) \cdot I_A(\lambda)$$

If the light source fluctuation is dominated by a Poisson process such as shot noise, then the autocorrelation may take the form:

$$\text{autocorr}(I_0(\lambda,t),\tau) = |I_0(\lambda)|_{\Delta t} \cdot \Delta t + |I_0(\lambda)|_{\Delta t}^2 \cdot \Delta t \cdot (\Delta t + \tau)$$

If we normalize the autocorrelation to the unshifted case, $\tau = 0$, the autocorrelation may no longer be wavelength dependent. In other words, the entire spectrum undergoing a poisson random process will have the same identical normalized autocorrelation function. Variability in the autocorrelation function with wavelength can only be due to dynamic absorbers. In addition, all dynamic absorbers composed of the same substance will produce the same autocorrelation function, which will differ from the autocorrelation function of a poisson process, unless the fluctuation in the number of absorbers is also a poisson process, which is not typically the case.

A dip in the intensity of a measured spectra indicates the presence of an absorber that is absorbing light at the wavelength centered on the location of the dip in the spectrum. The dip not only affects the amount of light delivered, the dip has structure itself. The spectral structure of an absorption line may be unique to the underlying absorption process that's creating the measured absorption. A continuous wavelet transform (CWT) is one way to represent spectral structure that naturally filters spectral slowly varying features from those with spectrally faster varying signals. Therefore, the spectral absorbance may be represented as a continuous wavelet transform. Performing a continuous wavelet transform on a dip location in a spectrum will provide spectral structure related to the spectral distribution of the light around a given dip location. Some dips may be described as sharp, others as shallow. These differences in dip shape may also provide a set of characteristic features that could uniquely identify a specific internal state that produces a given measured response.

By measuring the location and shape of absorption dips, a specific unique state may be specified. Using the wavelet decomposition as a measure of the shape of a spectral peak, a state may be quantified based on the spectral bins and their structural shape described by $N_v$ complex voices.

$$\vec{x}(\lambda, 2 \cdot N_v + 1)$$

First, the full state space may be divided into two states: a state $\vec{x}_A$, when substance A is present and state $\vec{x}_0$, when it is absent.

$$\vec{x}(\lambda, 2 \cdot N_v + 1) = \vec{x}_A(\lambda, 2 \cdot N_v + 1) + \vec{x}_0(\lambda, 2 \cdot N_v + 1)$$

In this example, there is an assumption that the spectral measurements are collected from a sample pool where the only difference between $\vec{x}_A$ and $\vec{x}_0$ is the presence of substance A. Given a set of known measurements, of states $\vec{x}_A$ and $\vec{x}_0$, a Kalman filter may be used to estimate the states $\hat{x}_A$ and $\hat{x}_0$, based on a series of measurements:

$$z_n(\lambda, \text{features}) = \sum_{i=1}^{i=\lambda_{band}/\Delta\lambda} z_n(\lambda_i; |I|, \text{Re}\{f_1\}, \text{Im}\{f_1\}, \ldots \text{Re}\{f_{N_V}\}, \text{Im}\{f_{N_V}\})$$

The Kalman filter algorithm may be split into two stages: Prediction and Update. During the prediction stage, a prediction of the state of the system is made based upon our current understanding of the state model.

Predicted state estimate:

$$\hat{x}_k^- = F\hat{x}_{k-1}^+ + Bu_{k-1}$$

Predicted error covariance:

$$P_k^- = FP_{k-1}^+ F^T + Q$$

During the update stage, a measurement may be made and the state estimate is updated. The update may have a measurement residual given by:

$$\tilde{y}_k = z_k - H\hat{x}_k^-$$

And a Kalman gain $$K_k = \frac{P_k^- H^T}{R + H P_k^- H^T}$$

After a measurement the state estimate may be updated:

$$x_k^+ = x_k^- + K_k y$$

And the state estimate's error covariance may also be updated:

$$P_k^+ = (I - K_k H) P_k^-$$

A Kalman filter estimates the state of a system given a set of known measurements. If a Kalman filter were applied to two different training sets, it would determine two different estimated states. Given the above equations, the goal is to minimize the estimated error covariance of updating each state with this new measurement. The distribution with the least negatively impacted covariance matrix is the best fit. This may also include cases where one selection improves the state estimate. Either way, with more measurements the Kalman filter may continue to improve discrimination.

Once a model is properly trained with positive and negative states, inferences may begin directly. The point of the inference measurement is to determine if a sample contains substance A. We can make those inferences (with large uncertainties) from the very first measurement. The error variance will improve if the system is properly specified initially. We can determine this based upon the expected update to each states covariance given the measurement as an update. As we better determine the state of the system through many measurements, we get a better understanding of substance A and how to find it in a large selection of data.

Figure 23:
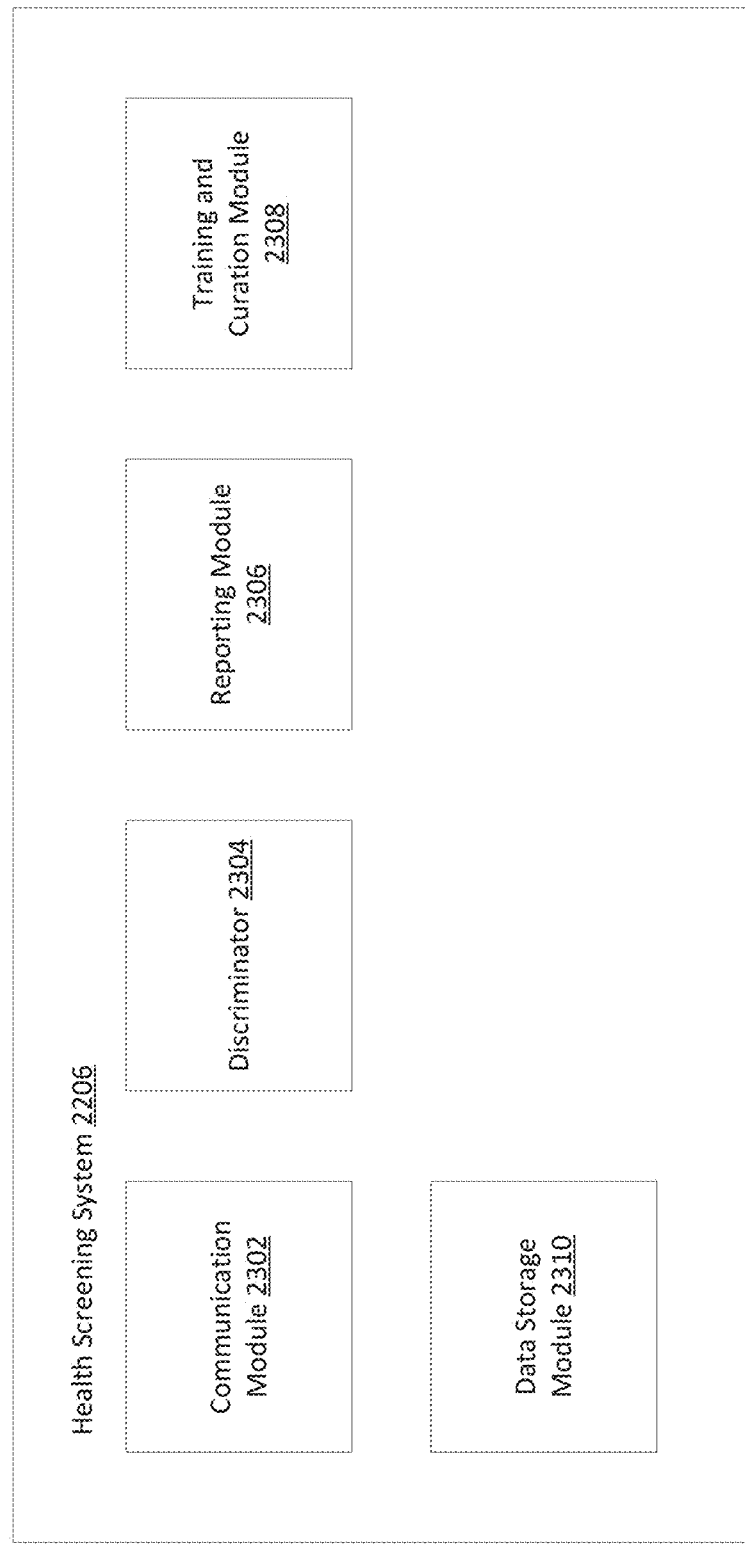
FIG. 23 depicts an example health screening system in some embodiments.

FIG. 23 depicts an example health screening system 2206 in some embodiments. The health screening system 2206 may include a communication module 2302, a discriminator 2304, a reporting module 2306, a training and curation module 2308, and a data storage module 2310

The health screening system 22306 may be configured to aggregate information from across patients and test results to provide reporting. The reporting may be in real-time. In various embodiments, the health screening system 2206 may, at the simplest level, receive test results and/or vortex spectrometer measurements from any number of patients in any number of locations. The health screening system 2206 may provide indications of infection (e.g., infected, not infected, likely infected, unlikely infected, or unknown) back to the device that provided the measurement results. In some embodiments, the health screening system 2206 may aggregate the information and provide reporting indicating that the number of virus infections detections and the number of test performed.

The communication module 2302 may receive spectrometer measurements of samples provided by patrons. In one example the communication module 2302 may receive a variety of different spectrometer measurements from any number of spectrometers regarding any number of patron samples. The patron sample may be sample of the patron's breath, saliva, or swab sample, or the like. The communication module 2302 may receive spectrometer measurements from any number of health communication devices 2202a-n.

The discriminator 2304 may receive and analyze the spectrometer measurements to categorize the results. Categories may include, for example, infected, not infected, likely infected, likely not infected, unknown, or any other labels. The discriminator 2304 may utilize statistical approaches, such as logistic regression, and/or AI modeling techniques such as convolutional neural networks.

In the example discussed herein, the discriminator 2304 may utilize scalograms of those known to be infected to identify areas of the graph associated with infection (e.g., by comparing scalograms of those known to not be infected). Infection or lack of infection, for example, may be confirmed by reagent test or other testing. The indication of infection based on a part of the scalogram(s) may be used as a reference. New test results may be used to generate information associated with all or part of the reference to indicate infection.

It will be appreciated that scalograms may not need to be generated to indicate infection. Rather, the discriminator 2304 may identify wavelength intensities from results of a vortex spectrometer associated with infection (e.g., as learned from the previous testing with known infections) and categorize those who are infected and not infected.

The degree to which new test results from new patients match the reference information (e.g., degree of confidence or fit) may be compared to a threshold to determine infection (e.g., above a particular degree of confidence or fit) or lack of infection (e.g., below a particular degree of confidence or fit).

Once the discriminator 2304 analyzes and categorizes the spectrometer results, infection indications such as health screening indications (e.g., "infected" or 'not-infected") may be returned to the health communication device that provided the original spectrometer measurements.

The discriminator 2304 may also store these spectrometer measurements and or results of the categorization analysis in the data storage module 2310.

In various embodiments, the discriminator 2304 may apply a logistic fit (e.g., a probability curve). Alternately, the discriminator 2304 may perform as a match filter.

In one example, the discriminator 2304 assesses a negative case (e.g., non-infected case) using large ensemble sampling. Similarly, the discriminator 2304 may assess a positive case. The discriminator 2304 may create a spectral curve of a negative case (of non-infection) and spectral curve of a positive case (e.g., of infection). The discriminator 2304 may create a characteristic curve for negative using a mean estimation over a sample size (e.g., 75,000 instances) after normalization. The negative characteristic curve is then used as a reference. The discriminator 2304 may take the (reference sample—the positive sample) divided by the reference sample to create a characteristic curve for infection. The discriminator 2304 may compare new spectral measurements and curves to the characteristic curve to determine likelihood of infection or categories of infection (e.g., based on the degree of fit to the characteristic curve for infection). A threshold may be set based on how known data fits the curve (e.g., based on known infection information and known uninfected information).

In some embodiments, the discriminator 2304 may utilize a bandpass of wavelengths using the characteristic curve for infection to create a window (e.g., a bandpass of wavelengths), assess mean value and standard deviation of the value, roll the window through the spectrum and iterate. The discriminator 2304 may plot the standard deviation vs. the mean for positive and negatives to identify wavelength bands that separate. This may be used as a method for separating information—for certain wavelengths, there may be significant separation and thereby enabling easy identification of infection vs. noninfection.

The reporting module 2306 may assess and aggregate the information including spectrometer measurements from any location, any spectrometer, any patrons, or the like as well as the categorized labels. As a result, the reporting module 2306 may be able to provide reports regarding infection rates in geographic areas, types of patrons, success of vaccinations, and/or the like.

The training and curation module 2308 may training and/or curate the statistical approaches and/or AI modeling techniques based on the received spectrometer measurements and the results from the discriminator 2304. It will be appreciated that the training and curation module 2308 will enable improvements is statistical analysis and AI modeling because of the variety and amount of data received from numerous geographically remote and diverse sources. As a result, the training and curation module 2308 may improve accuracy, speed of analysis, and scalability of future testing.

The data storage module 2310 may store spectrometer measurements and/or output from the discriminator 2304. In some embodiments, data stored in the data storage module 2310 may be stripped of personally identifying information. Since the stored data may be used for aggregate reporting, training, and/or curation, personally identifying information may not be necessary to store.

The data storage module 2310 may be encrypted. Further, communication between the health communication devices 2202*a-n* and the communication module 2302 may be encrypted (e.g., via VPN) and/or authenticated (e.g., through the use of encryption keys and/or digital certificates).

A module may be hardware, software, or a combination of both hardware and software. A hardware module may be a chip (e.g., ASIC) or the like. Software may be executed by a processor. Although a limited number of modules are depicted in the figure, there may be any number of modules. Further, individual modules may perform any number of functions, including functions of multiple modules as shown herein.

Figure 24:
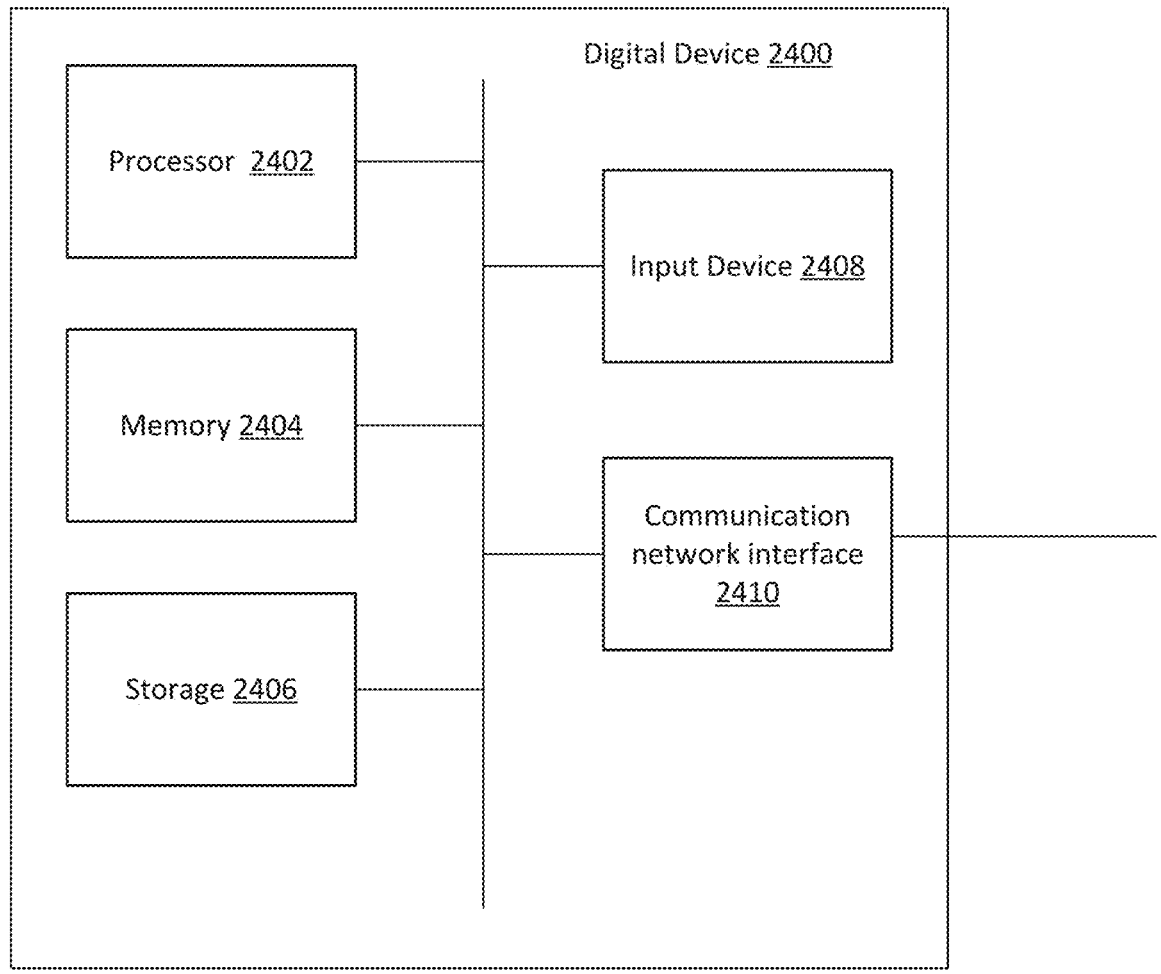
FIG. 24 depicts a block diagram of an example digital device according to some embodiments

FIG. 24 depicts a block diagram of an example digital device 2400 according to some embodiments. Digital device 2400 is shown in the form of a general-purpose computing device. Digital device 2400 includes processor 2402, RAM 2404, communication interface 2406, input/output device 2408, storage 2410, and a system bus 2412 that couples various system components including storage 2410 to processor 2402.

System bus 2412 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Digital device 2400 typically includes a variety of computer system readable media. Such media may be any available media that is accessible by the digital device 2400 and it includes both volatile and nonvolatile media, removable and non-removable media.

In some embodiments, processor 2402 is configured to execute executable instructions (e.g., programs). In some embodiments, the processor 2402 comprises circuitry or any processor capable of processing the executable instructions.

In some embodiments, RAM 2404 stores data. In various embodiments, working data is stored within RAM 2404. The data within RAM 2404 may be cleared or ultimately transferred to storage 2410.

In some embodiments, communication interface 2406 is coupled to a network via communication interface 2406. Such communication can occur via Input/Output (I/O) device 2408. Still yet, the digital device 2400 may communicate with one or more networks such as a local area network (LAN), a general wide area network (WAN), and/or a public network (e.g., the Internet).

In some embodiments, input/output device 2408 is any device that inputs data (e.g., mouse, keyboard, stylus) or outputs data (e.g., speaker, display, virtual reality headset).

In some embodiments, storage 2410 can include computer system readable media in the form of volatile memory, such as read-only memory (ROM) and/or cache memory. Storage 2410 may further include other removable/non-removable, volatile/non-volatile computer system storage media. By way of example only, storage 2410 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CDROM, DVD-ROM or other optical media can be provided. In such instances, each can be connected to system bus 2412 by one or more data media interfaces. As will be further depicted and described below, storage 2410 may include at least one program product having a set (e.g., at least one) of program modules that are configured to carry out the functions of embodiments. In some embodiments, RAM 2404 is found within storage 2410.

Program/utility, having a set (at least one) of program modules may be stored in storage 2410 by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of embodiments as described herein. A module may be hardware (e.g., ASIC, circuitry, and/or the like), software, or a combination of both.

It should be understood that although not shown, other hardware and/or software components could be used in conjunction with the digital device 2400. Examples include, but are not limited to: microcode, device drivers, redundant processing units, and external disk drive arrays, RAID systems, tape drives, and data archival storage systems, etc.

Exemplary embodiments are described herein in detail with reference to the accompanying drawings. However, the present disclosure can be implemented in various manners, and thus should not be construed to be limited to the embodiments disclosed herein. On the contrary, those embodiments are provided for the thorough and complete understanding of the present disclosure, and completely conveying the scope of the present disclosure to those skilled in the art.

As will be appreciated that aspects of one or more embodiments may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband/or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects discussed herein may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of some of the embodiments are described herein with reference to flowchart illustrations and/or block diagrams of methods, apparatus (systems) and computer program products according to embodiments. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a nontransitory computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Projecting light at one or more different wavelengths through a disordered medium may provide accuracy improvements in measurements of the wavelength(s). For example, light projected through a diversifier (e.g., speckle pattern or diffuser) causes the light to scatter as light impacts occlusions or marks in the diversifier (e.g., in the speckle or diffuser). The scattering is dependent (at least in part) on the wavelength of the light. The scattering caused by the speckle/diffuser is linear and reproducible. As such, the scattered light caused by the diversifier may be measured and patterns of spectral intensities may be associated with one or more different wavelengths projected by a light source. Based on these associations, spectral intensities may be reconstructed.

By reconstructing the spectral intensities, noise present during a pattern recognition phase may be omitted from the reconstruction. It will be appreciated that noise may be caused by temperature, defects in the light path, the light source, and/or other sources between the light source and detector. Unlike wavelengths from the light source that, when scattered by the diversifier, generate reliable, repeating patterns, noise is inconsistent and may be omitted during spectral reconstruction.

Filtering information may be generated based on spectral reconstruction. The filtering information may be used to remove noise (e.g., noise that is inconsistent with the expected patterns caused by the diversifier).

The system may subsequently be used to test for pathogens in samples from patients. Light at known wavelengths may be projected through a cuvette containing a biological sample. The system may include all or some of the same light source, light path, diversifier, detector, and the like used for spectral reconstruction. By using the filtering information and/or spectral reconstruction to reduce or ignore noise, signals caused by scattering of pathogens in the signal may be detectable. It will be appreciated that the size of certain pathogens (e.g., Covid 19) may create spectral signals that would otherwise be subsumed by noise and/or other spectral intensities if not for spectral reconstruction.

In various embodiments, using the filtering information and systems described regarding spectral reconstruction, numerous samples containing known pathogens (e.g., all containing Covid 19) may be tested to identify spectral signatures associated with the specific pathogen. Various embodiments may use artificial intelligence as described herein to identify the spectral signature of the pathogen in view of known wavelengths of the light source applied during testing.

The spectral signature, as discussed herein may become a fingerprint for one or more pathogens. After a pathogen spectral signature is obtained, samples may be tested to determine whether the pathogen is present (e.g., the user that provided the sample is infected with the pathogen). In various embodiments, once filtering information is generated for a system, the system may then be used to test one or more samples from the user. It may be unknown if the one or more samples contain any of the pathogen being tested. Using the filtering information, the spectral intensities of the result (after passing through the sample) may be determined and then compared to the pathogen spectral signature (e.g., filtering out noise and/or the spectral intensities of the light source). If the pathogen spectral signature is detected, the system may indicate a positive finding of the pathogen and/or information regarding the spectral intensities detected.

Many of the examples discussed herein contemplate one pathogen being detected. It will be appreciated that any number of pathogens may be detected (e.g., by comparing results from a sample against any number of different pathogen spectral signatures).

It will also be appreciated that detection may occur using a cloud-based system. In various embodiments, a spectrometer with a diversifier may be tested to determine the impact of the diversifier on a light path with a controlled light source. Filtering information may be obtained based on the testing (as discussed herein) and applied using the spectrometer, a digital device local to the spectrometer, or in the cloud. Subsequently, future testing of different patient samples using the same spectrometer may be assessed using the filtering information and pathogen spectral signature(s) using a processor associated with the spectrometer, a digital device local to the spectrometer, or in the cloud.

By using a cloud system to compare results from any number of spectrometers, pathogen spectral signature(s) may be updated, corrected, improved, and/or modified in a central system (as opposed to attempting to provide pathogen spectral signatures to thousands or hundreds of thousands of devices proximate to spectrometers around the world). Further, the system may continue to learn from measurements and samples to improve detection, signature generation, and the like. Further, new variations may be more quickly assessed.

Light may be transmitted through the diffuser or speckle pattern to a detector. Temperature of the spectrometer may be controlled during testing. Similarly, the current and wavelength of the light source may be controlled during detection of the scattering of light (e.g., caused by the diffuser or speckle). This may allow capturing of measurements of the diffusion or speckle as a function of wavelength and current. These measurements may be taken with or without the light passing through a cuvette containing a medium (e.g., water or VTM but not a biological sample).

Patterns may be recognized in many different ways. In various embodiments, artificial intelligence may be used, such as a convolutional neural network or a deep neural network, to identify patterns of scattering associated with different current and/or wavelengths.

Once measurements are taken, filtering information may be generated. The filtering information is information that allows for the spectrometer and/or digital device to remove noise in the system (e.g., within the spectrometer) to better detect signals (e.g., spectral intensities) caused by pathogens caught in the light path, thereby increasing the signal-to-noise ratio and/or improving the accuracy of the spectral measurements. In one example, light from a light source may pass through the sample before being projected through the diffuser or speckle pattern. The detector may then take spectral data measurements of the light and utilize weighting, filtering, or the like (e.g., using the filtering or measurements determined without the sample) per wavelength to reduce noise in the measurements.

In one example, a deep neural network may assist in spectral reconstruction. In some embodiments, a deep neural network (DNN) may be trained to identify impact of the speckle or diffuser on light from a controlled light source by simultaneously measuring a variable control input and a signal output. In one example, this may be accomplished by simultaneously measuring a speckle field with a 2D pixel array and measuring a spectrum while modulating the spectrum of the light source. The DNN may be trained to identify wavelengths of the light source by simultaneously (or near simultaneously) measuring the current applied to a light source (e.g., a 635 nm red LED light source) and the output of a spectrometer (e.g., a VIS-NIR spectrometer).

DNN-assisted spectral reconstruction may be performed with a wide variety of variable input controls.

Figure 25:
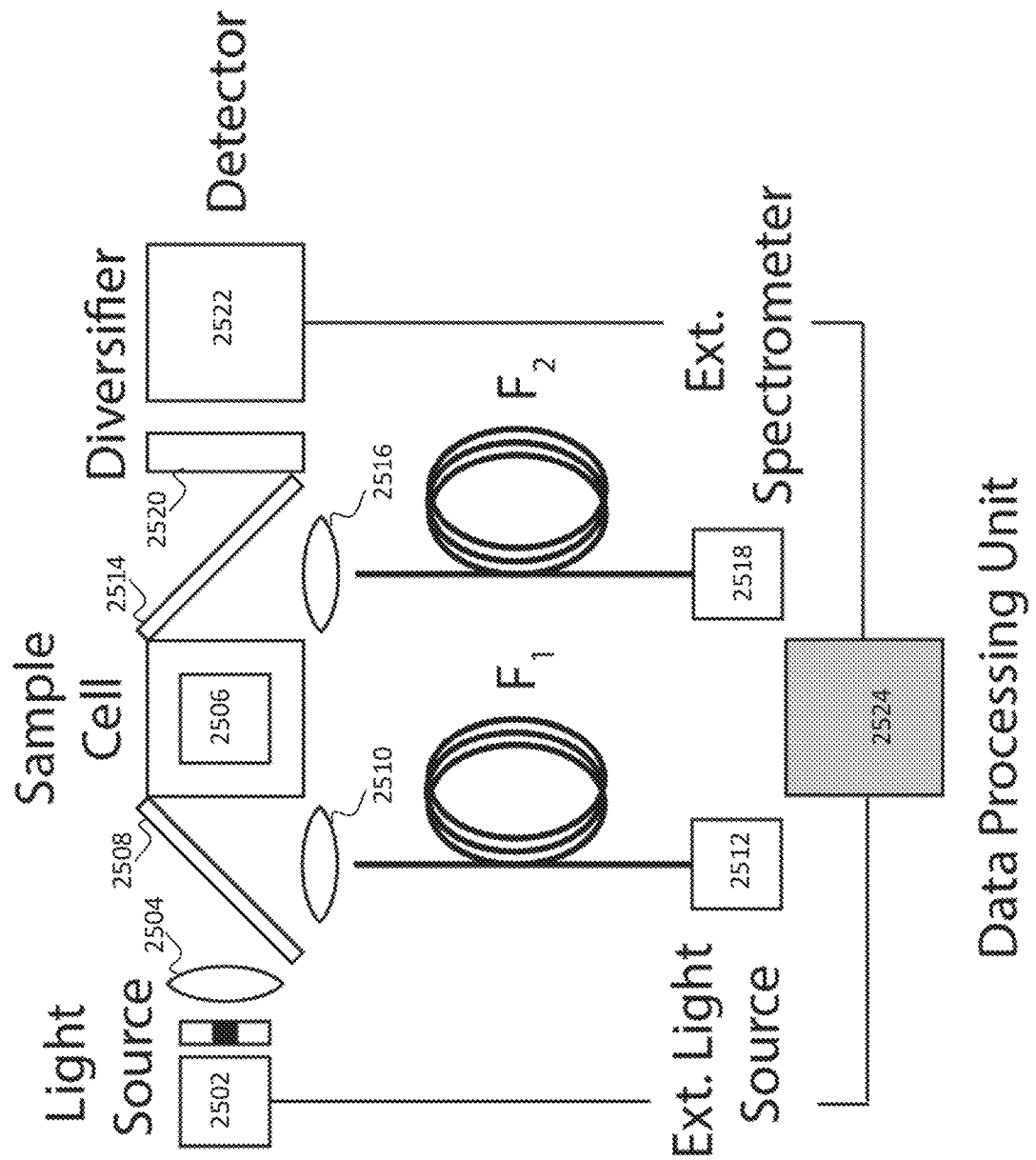
FIG. 25 depicts a system for spectral reconstruction based on scattered light caused by a diversifier in some embodiments.

FIG. 25 depicts a system for spectral reconstruction based on scattered light caused by a diversifier in some embodiments. The system depicted in FIG. 25 may be a spectrometer or any system for measuring spectral intensities. The system may include the light source 2502 that projects light through slit 2526, the collimator lens 2504, sample cell 2506, and diversifier 2520 to detector 2522. Optional light divider 2508 may allow for additional wavelengths and/or improved light source control based on external light source 2512. Light divider 2514 may redirect a portion of the light from the sample cell 2506 to the external spectrometer 2518 for measurement.

The light source 2502 may be any source of light including, but not limited to, a laser, LED, or the like. The light source 2502 may be controlled by the data processing unit 2524. In one example, the data processing unit 2524 may control the light source 2502 to project any number of wavelengths using selected currents. By controlling the light source 2502, the data processing unit 2524 may correlate wavelengths to scattered patterns detected by the detector 2522.

The slit 2526 may comprise any material and may include one or more holes or slits to assist in collimation of the light source 2502. The slit 2526 may be optional.

The lens 2504 may be any lens capable of collimating and/or focusing light from the light source 2502 to the sample cell 2506. The system may include a light source 2502 that projects light through a lens 2504 (e.g., a collimator) and then through sample cell 2506. The sample cell 2506 may be a cuvette or any object for retaining a sample. When measuring the impact of the diversifier 2520, the sample cell 2506 may not contain a biological sample. In some embodiments, the sample cell 2506 contains water, VTM, or the like. In some embodiments, the sample cell 2506 may not contain any material (e.g., fluid or otherwise) when measuring the speckle. In various embodiments, there is no sample cell 2506 but rather there is no object in that part of the light path (e.g., the cuvette is removed or not inserted in the light path).

The light along the light path may pass through the sample cell 2506 (or the space for sample cell 2506) and may be divided by a light divider 2514. Light from light divider 2514 may divert a portion of the light received from the sample cell 2506 to lens 2516 to the external spectrometer 2518 (via fiber or secondary light path F2). The external spectrometer 2518 may be, in some embodiments, only a second detector. Lens 2516 may focus or otherwise collimate the light. In various embodiments, the external spectrometer 2518 may measure spectral intensities right before light passes through the diversifier 2520. As such, the data processing unit 2524 may assess measurements from the detector 2522 (taken of the scattered light of the diversifier 2520) and the measurements from the external spectrometer 2518. The assessment may be further analyzed by taking into account the wavelengths and currents provided by the light source 2502 and/or the external light source 2512.

Data processing unit 2524 may take the measurements to assist in generating a filter based on the diversifier in order to reduce noise. In one example, this may be accomplished by simultaneously measuring the diversifier (e.g., a speckle field or diffuser) with a 2D pixel array and measuring a spectrum while modulating the spectrum of the light source.

The data processing unit 2524 may control the light source 2502 to select wavelengths for measurements by detector 2522. In some embodiments, the data processing unit 2524 does not control the light source 2502 but rather receives wavelength information of light generated by the light source 2502 (e.g., the light source 2502 provides wavelength and any other information to the data processing unit 2524). In some embodiments, the data processing unit 2524 may also control the external light source 2512 to select wavelengths for measurements by detector 2522. In some embodiments, the data processing unit 2524 does not control the light source 2512 but rather receives wavelength information of light generated by the light source 2512 (e.g., the light source 2512 provides wavelength and any other information to the data processing unit 2524).

The data processing unit 2524 may also receive spectral measurements from the detector 2522. For example, the detector 2522 may receive information or make measurements based on light received from the light source 2502 (e.g., after being projected through sample cell 2506 and the diversifier 2520). The data processing unit 2524 may also receive spectral measurements from the detector of the external spectrometer 2518. For example, the detector may receive information or make measurements based on light received from the light source 2502 (e.g., after being projected through sample cell 2506 and partially diverted by the divider 2514).

The data processing unit 2524 and/or other digital devices may utilize the information regarding wavelength transmitted over the light path, the spectral intensities detected by the external spectrometer detector (before the light passes through the diversifier 2520), and the spectral intensities detected by the detector 2522 (after the light passes through the diversifier 2520) to identify patterns of light scattering caused by the diversifier 2520.

The data processing unit 2524 may associate detected spectral patterns of scattering caused by the diversifier 2520 with current and wavelength. In various embodiments, the data processing unit 2524 and/or other digital devices may utilize a DNN or other pattern recognition approaches to detect patterns and associate the patterns with the wavelengths and current of the light source generated the light provided to the light path.

The data processing unit 2524 may generate filtering information (e.g., a function to characterize diffusion or speckle based on wavelength and current). Using this information, the data processing unit 2524, other processors (e.g., in the cloud), and/or AI systems may generate filters to remove noise and significantly improve the signal to noise ratio (SNR).

The diversifier 2520 may be a speckle pattern, diffuser, series of vortexes, and/or the like. In various embodiments, the diversifier 2520 is any material with occlusions or obstructions that cause scattering of the light provided by the light source. The scattered, incoherent light may be detected by the detector 2522 for pattern recognition and filter information generation for improvement of signal detection.

In some embodiments, a well-defined and controlled light source (e.g., capable of providing any number of wavelengths over different currents), such as external light source 2512 may be utilized to assist in measuring the scattered light caused by the diversifier. The external light source 2512 may provide light at known wavelengths via fiber (or light path) F1, through lens 2510 to divider 2508. The divider 2508 may project the light from the external light source 2512 through sample cell 2506 to the divider 2514 and diversifier 2520. The external light source 2512 may be used to assist in measuring any number of systems using different diversifiers which may allow for simplified association of patterns of scattered spectral intensities caused by interaction with the diversifier. It will be appreciated that the light divider 2508, lens 2510, and external light source 2512 may be optional.

Spectra may be recreated from speckle diffusers and/or vortex matrices in many different ways. In some embodiments, light from a light source (in a spectrometer) is measured (e.g., by a camera) after the light is transmitted through a medium with different absorption features and subsequently transmitted through a particular diffuser containing a speckle pattern. The diffuser creates a wavelength dependent speckle structure in the images captured by the CMOS camera. The captured images may be used to train a Deep Neural Network (DNN) to reconstruct the original spectra. The use of a CMOS camera and speckle diffuser allows for a much more compact and cheaper spectroscopy system. With comparable accuracy, this system may allow inexpensive spectrometers to be integrated into a wide variety of applications.

In another example, a light source 2502 (e.g., a Super-Continuum light source) of a spectrometer may transmit broadband light through a sample cell 2506, through a speckle diversifier 2520, and onto a detector 2522 (e.g., a CMOS camera). The light from the light source 2502 may impinge on a beam cube (e.g., light divider 2508) and splits the light in two different directions, to the right and downward. The light from the right path is passed through a cuvette (e.g., sample cell 2506) that can contain a sample before going through a polarizing filter and then impinging on another beam cube (light divider 2514). This splits the beam into two paths again, one path going straight through to the spectrometer 2518. The other path sends the light through the speckle diffuser filter (e.g., diversifier 2520). Before the CMOS camera (e.g., detector 2522), there may be a microscope filter (e.g., 60X Microscope Objective) between the divisifier 2520 and the detector 2522 (not depicted in FIG. 25) to zoom in on the speckle of the diversifier 2520.

The data from this example may be used to train a DNN to reconstruct spectra. For example, the data from this example may be split into input and output sections. The inputs may include speckle diffuser images captured by the CMOS camera (e.g., detector 2522). The output may include simultaneously captured spectra of the light transmitted through the sample (sample cell 2506). In one example, this may be done using an Avantes Spectrometer and saving the spectra as a Numpy array. This spectrum may be used as the true spectrum in the DNN regression analysis after the training.

A basis set may be created to span the possible output wavelengths of light from the Supercontinuum light source (e.g., light source 2502). This set may be generated by sweeping light (e.g., from 450 nm to 1000 nm with a step size of 5 nm). The use of a basis set allows for a much larger dataset to be generated from a small amount of data. Feature changes may be applied that affect the speckle diffuser image by applying the weight of each wavelength of the spectrum to the image.

Subsequently, the speckle diffuser images may be further processed to highlight the differences between feature changes in the spectra. To do this, an image and spectra may be generated without any absorption features. This is done to show only the feature changes in the final output image for the Neural Network training. Each image of the dataset may be loaded in one-by-one and first averaged to remove the mean of the image from itself. This is a standard statistics procedure to ensure that the dataset is zero mean with a standard deviation of one. The zero mean image may be then normalized by the absolute value of the total sum of intensity of the image. This helps to remove any bias in the dataset and ensures a fair comparison between the data points. Subsequently, the "no absorption" image is subtracted from the dataset image to leave only the feature changes that were applied to the spectra. Note that the spectrum is not changed in this step. After this processing, the dataset may be passed through another script that links the images and spectra for use in the Neural Network training.

Figure 37:
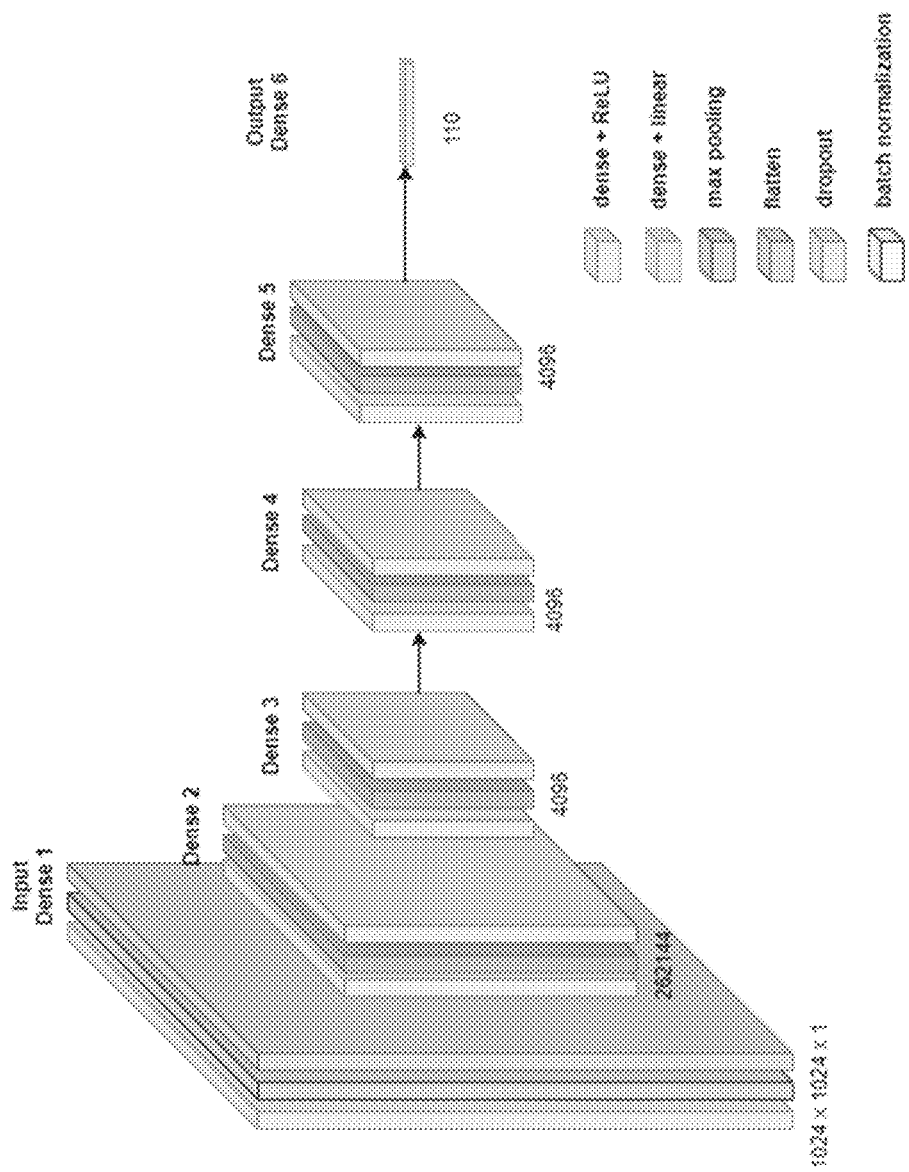
FIG. 37 depicts an example deep neural network and example configuration in some embodiments.

A Regression based Deep Neural Network may be used to achieve spectral reconstruction. Regression is used in this example to predict an array of floating point values that correspond to the original spectrum. The model may be composed of multiple Dense Layers used in the Input Layer, Hidden Layers, and Output Layer. FIG. 37 depicts an example deep neural network and example configuration in some embodiments. Between each Dense Layer are Batch Regularization and Dropout Layers to help the network generalize.

In previous testing, the configuration of the deep neural network depicted in FIG. 37 recreated the spectra with a mean error of 0.0322 and an error standard deviation of 0.0328. Error may be calculated by dividing the total sum of the absolute value of the difference between the predicted spectra and actual spectra by the absolute value of the sum of the actual spectrum.

Figure 38:
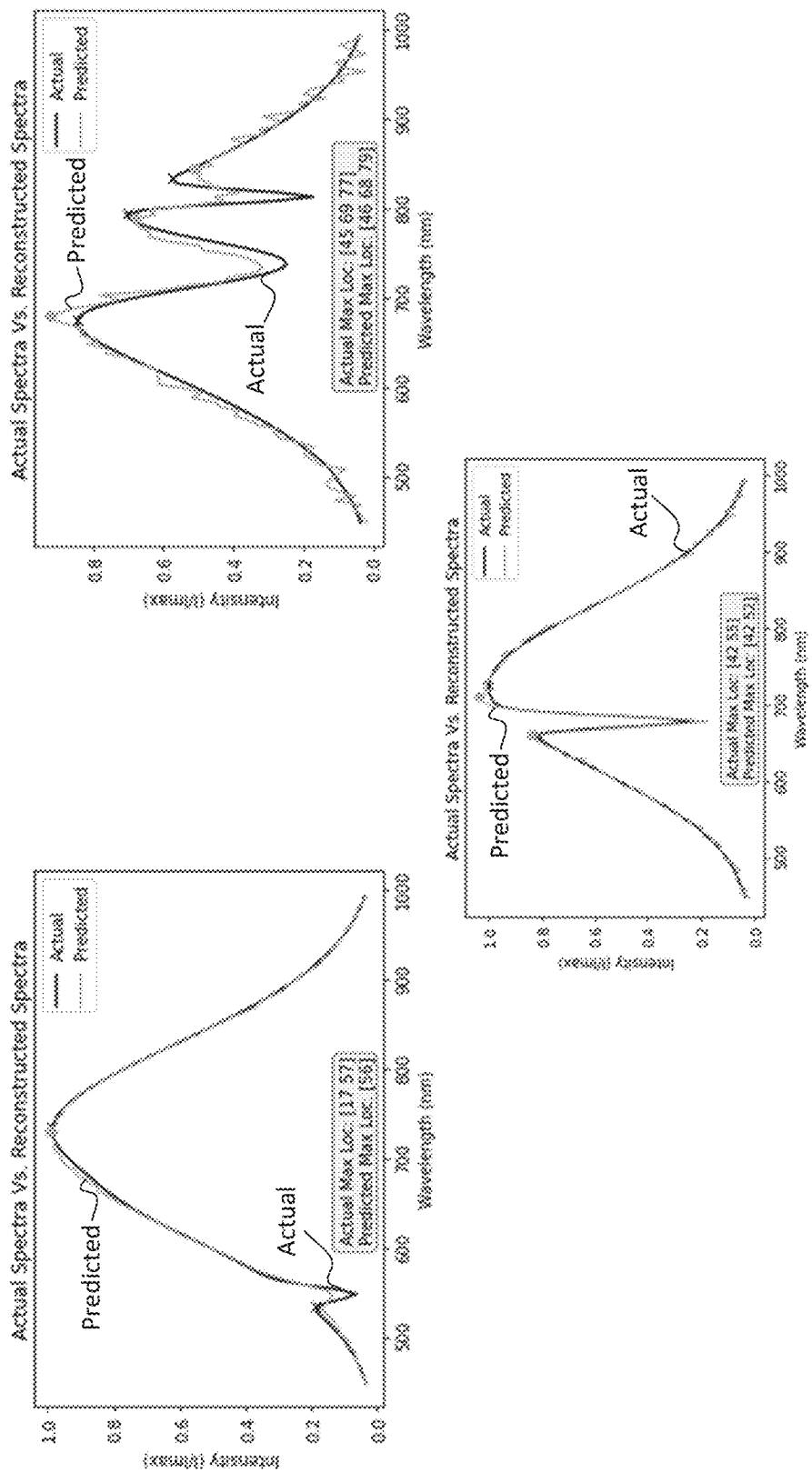
FIG. 38 includes comparisons of actual spectra plotted against reconstructed spectra in testing in some embodiments.

FIG. 38 includes comparisons of actual spectra plotted against reconstructed spectra in testing in some embodiments.

Figure 26:
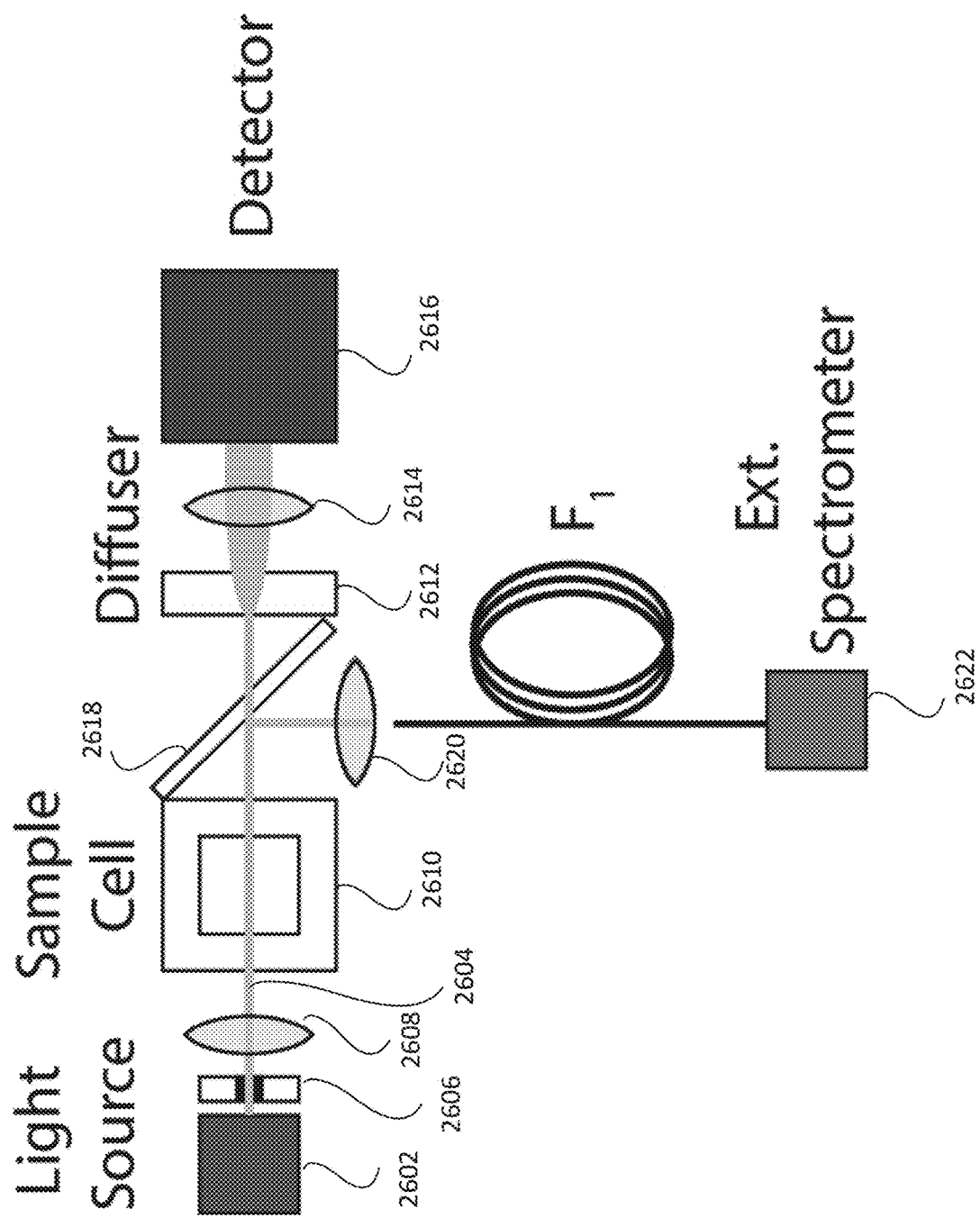
FIG. 26 depicts a system for spectral reconstruction based on scattered light caused by a diversifier but without an external light source in some embodiments.

FIG. 26 depicts a system for spectral reconstruction based on scattered light caused by a diversifier but without an external light source in some embodiments. The system depicted in FIG. 26 may be similar to that of FIG. 25 but without the external light source 2512, divider 2508, and lens 2510. Similar to FIG. 25, the system of FIG. 26 depicts a light source 2602, light path 2604, a slit 2606, lens 2608, sample cell 2610, diffuser 2612, lens 2614, detector 2616, divider 2618, lens 2620, and external spectrometer 2622.

The light source 2602 may be similar to the light source 2502 and may project light along light path 2604 to the detector 2616. Although not depicted, a processor (e.g., data processing unit) may control the light source to control current and wavelength for scatter pattern testing of the diffuser 2612. The slit 2606 may be similar to slit 2526.

Further, the lens 2608, sample cell 2610, divider 2618, detector 2616, lens 2620, and external spectrometer 2622 may be similar to lens 2504, sample cell 2506, divider 2514, detector 2522, lens 2516, and external spectrometer 2518, respectively.

In this example, the light source 2602 may provide light at specific frequencies when needed for testing.

The diffuser 2612 may be any diversifier. In one example, the diffuser 2612 may comprise crushed glass. It will be appreciated that the diffuser 2612 and/or diversifier 2520 may comprise any material(s) that allow for light to pass but also includes speckle, occlusions, or obstacles to scatter light. In some embodiments, the diffuser 2612 may be a speckle that is reproduceable (e.g., by tape, reproduced film, 3D hologram, or the like).

The lens 2614 may collimate or focus light received from the diffuser (which may spread as a result of the scattering) before the light is received by the detector 2616. In some embodiments, the lens 2614 may project a portion of the light that passes through the diffuser 2612. For example, one or more lenses may direct light that is scattered by one or more specific occlusions of the diffuser 2612 to the detector 2616. In some embodiments, one or more lenses may focus scattered light from a subset of occlusion and/or vortexes of the diffuser 2612 to the detector. In some embodiments, light from the areas of the diffuser 2612 that is not being projected through the subset of occlusions may be ignored, blocked, or otherwise disregarded for pattern recognition and/or signal detection improvement.

Figure 27:
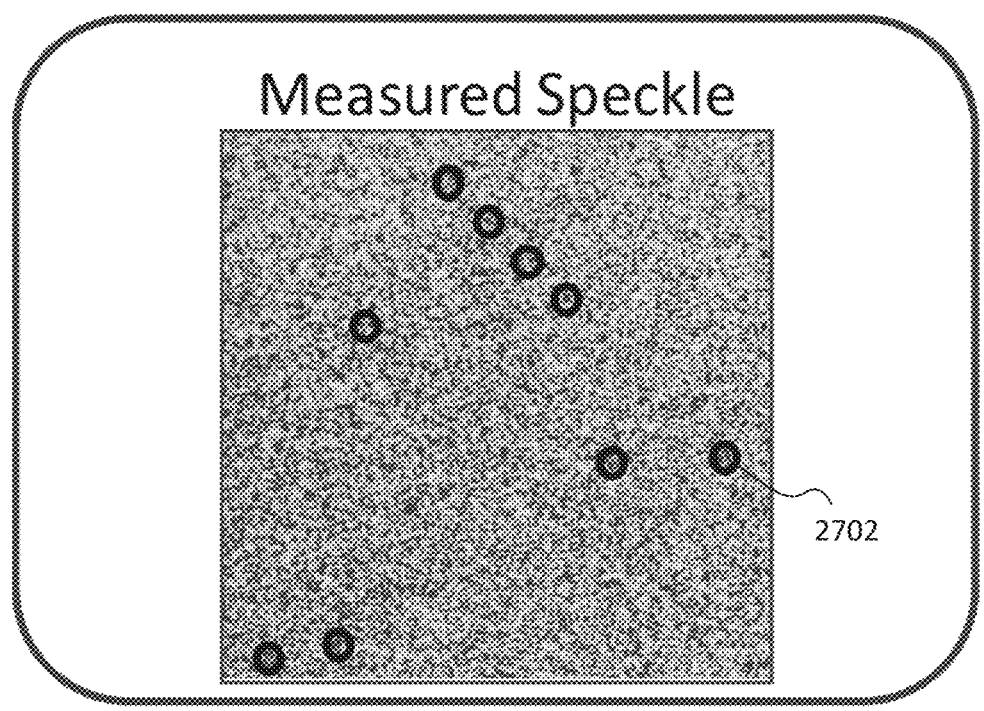
FIG. 27 is an example of a speckle pattern in some embodiments.
Figure 28:
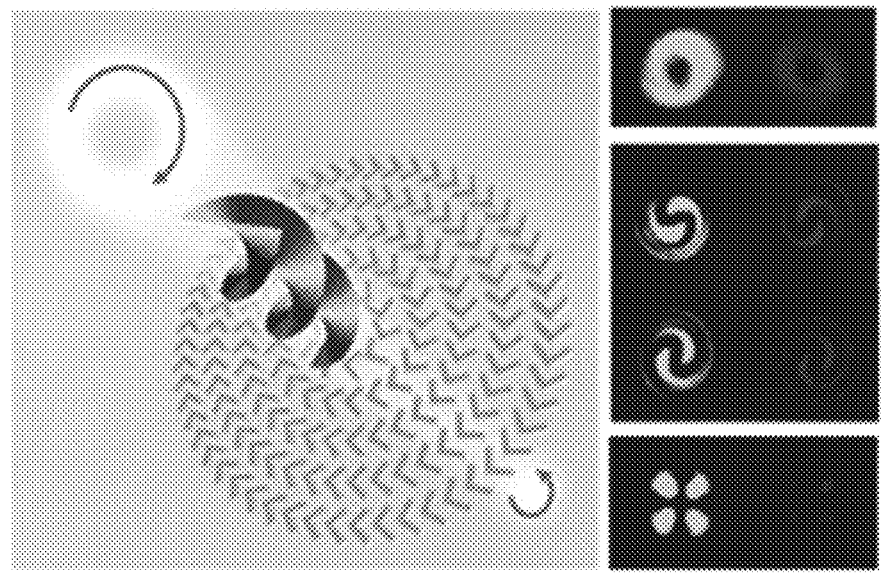
FIG. 28 depicts an example optical vortex meta-surface.
Figure 29:
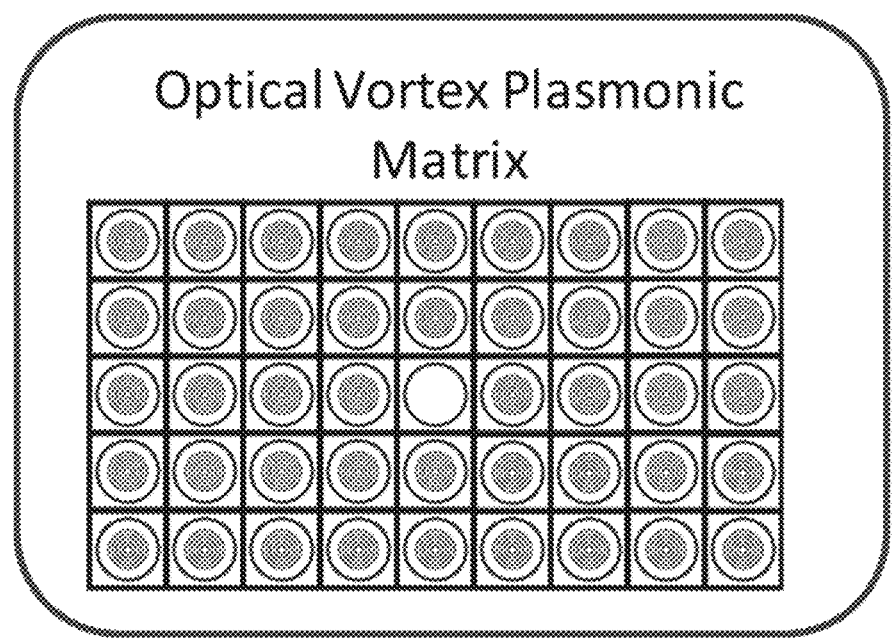
FIG. 29 depicts an optical vortex plasmonic matrix that may be utilized rather than the diffuser, speckle pattern, or optical vortex meta-surface.

FIGS. 27-29 depict different types of diversifiers. FIG. 27 is an example of a speckle pattern in some embodiments. In one example, the speckle pattern is composed of bright and dark speckle that create interference of spatially coherent light. A diversifier may be at least partially transparent and include speckle similar to the speckle pattern depicted. Light scattered by a sample in the sample cell is spatially incoherent and scatters light into the dark speckle cores. The spectral reconstruction signal contrast can be enhanced by limiting the reconstruction to pixels in the dark spectral cores (e.g., dark spectral core 2702 and those cores that are circled).

In various embodiments, the material with the speckle pattern is transparent to allow light to pass the material although with the scattering effect caused by the speckle. A detector (e.g., detector 2522 depicted in FIG. 25) may receive the light after being scattered by the speckle.

Some of the speckle may create greater scattering effects than other speckle. In some embodiments, after light is passed through the speckle pattern and the speckle is measured (e.g., as a function of current and wavelength), specific aspects or occlusions of the speckle (e.g., occlusion or dark spectral core 2702) may provide scattering that is associated with wavelength and current. Other aspects or occlusions of the speckle may not provide sufficient patterns or information to associate with the wavelength of the projected light and, as such, may be disregarded. As such, filter information may be generated that utilizes some but not all of the speckle for noise reduction.

The speckle pattern and/or material includes the speckle pattern may be created in any number of ways. In some embodiments, tape (e.g., scotch tape) may be used to collect debris to create the speckle effect. In another example, glass with an etched image or containing a hologram may further contain marks or material to create the speckle pattern.

In some embodiments, instead of speckle, an optical vortex meta-surface may be utilized. FIG. 28 depicts an example optical vortex meta-surface. In some embodiments, the diversifier (e.g., diversifier 2520) may be an optical vortex meta-surface.

Like dark speckle cores, optical vortices form from the destructive interference of coherent light. An optical vortex plasmonic matrix may be a two-dimensional array of sub-wavelength plasmonic metasurfaces and may be used to create a uniform vortex lattice. Similar to the speckle cores, the spectral reconstruction signal contrast can be enhanced by limiting the reconstruction to pixels in the dark vortex cores.

As discussed herein, when the light passes through a scattering medium containing particles larger than the wavelength, light is scattered. The most intense scattering usually occurs in the forward direction. Light scattered along the optical axis is often difficult to distinguish from the superimposed unscattered laser beam, especially when there is a dilute concentration of weak scatterers. This scattered light may interfere with the light of the principle beam and, as a result, speckle (i.e., noise) may be formed.

In some cases, particular wavelengths may be absorbed by the scattering media. This occurs because the light at those particular wavelengths excite the rotational or vibrational state of the molecules in the media. Therefore, the chemical makeup of an absorbing media may be based on the spectral absorption signature that is present. If the medium is weakly scattering (i.e., there are few scatterers), the absorption signature may be overwhelmed by the strong on-axis unscattered light source. Therefore, in order to optimize the characterization of the scattering molecules, a light suppression technique may be utilized to attenuate the strong on-axis source while leaving the weaker scattered signal intact.

An optical vortex is a dark null of destructive interference that occurs at a spiral phase dislocation in a beam of spatially coherent light. The phase of a transmitted light beam may be twisted and light from opposite sides of the mask may coherently destructively interfere to form a dark null in the transmitted intensity pattern, much like the eye of a hurricane.

The vortex may assist to create destructive interference of the light source, thereby enabling improved sensitivity of fainter signals.

FIG. 29 depicts an optical vortex plasmonic matrix that may be utilized rather than the diffuser, speckle pattern, or optical vortex meta-surface. The optical vortex plasmonic matrix may include any number of optical vortex meta-surfaces. Each of the optical vortex meta-surfaces may be different from each other. For example, each of the optical vortex meta-surface of the optical vortex plasmonic matrix may have different properties to allow for destructive interference of coherent wavelengths of light, thereby allowing for improved sensitivity of fainter signals of incoherent light.

It will be appreciated that different wavelengths projected by the light source may be effected differently by one or more vortexes of the optical vortex plasmonic matrix. One or more different vortexes of the optical vortex plasmonic matrix may produce patterns and signals. A detector may assess all or only specific optical vortexes of the optical vortex plasmonic matrix to identify patterns associated with different currents and/or wavelengths to enable boosting of signals of interest and spectral reconstruction to eliminate noise.

Each of the vortexes of the optical vortex plasmonic matrix may perform similarly to the function of the vortex of the vortex mask 840 discussed regarding FIG. 8. For example, the vortex may be an optical vortex coronagraph An example optical vortex coronagraph uses a helical phase of the form $ei\phi$, with $\phi=l\theta$, where l is the topological charge and $\theta$ is the focal plane azimuthal coordinate. In optical systems, vortices manifest themselves as dark donut of destructive interference that occur at phase singularities. For example, $E(\rho, \phi, z, t)=A(\rho, z) \exp(il\theta) \exp(i\omega t - ikz)$ where $(\rho, \phi, z)$ are cylindrical coordinates, $A(\rho, z)$ is a circularly symmetric amplitude function and $k=2\pi/\lambda$ is the wavenumber of a monochromatic field of wavelength $\lambda$.

In some embodiments, the optical vortex coronagraph may utilize a rotationally symmetric half wave plate which can generate an azimuthal phase spiral reaching an even multiple of 2pi radian.

Although the optical vortex plasmonic matrix of FIG. 29 depicts a 5×9 array of vortexes (with a missing vortex in the middle), it will be appreciated that there may be any number of vortexes in any orientation.

In some embodiments, the optical vortex plasmonic matrix of FIG. 29 includes a non-integer vortex array. A non-integer vortex array may have a random, non-integer topological charge, $l_{mn}$ for a given desired wavelength $\lambda_0$ given by:

$$l_{mn}=l_0+\Delta l_{mn}$$

Figure 34:
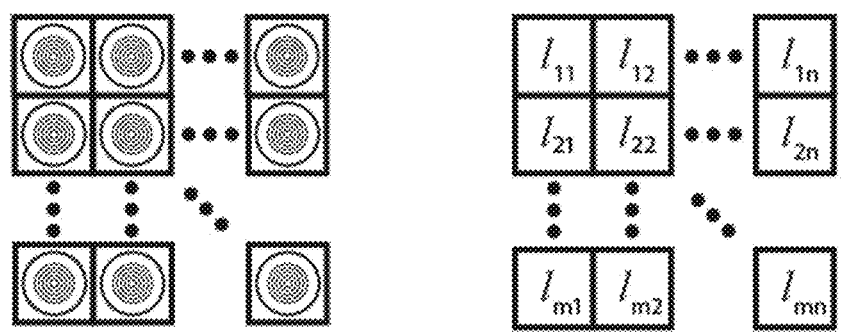
FIG. 34 depicts an example mapping of an optical vortex plasmonic array to a non-integer topological charge $l_{mn}$.

FIG. 34 depicts an example mapping of an optical vortex plasmonic array to a non-integer topological charge $l_{mn}$.

Figure 35:
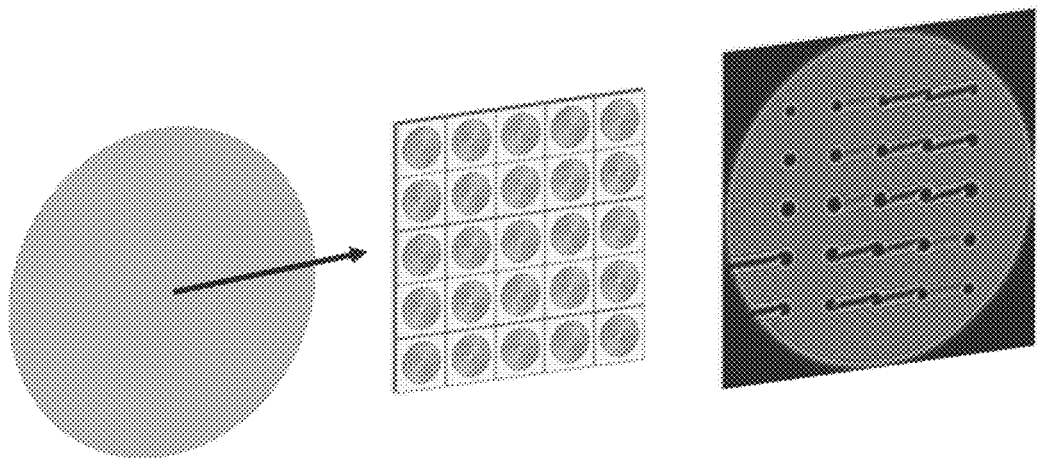
FIG. 35 is an example graphic of light shining on a non-integer vortex array waveplate and an example resulting image in some embodiments.

Light transmitted through the non-integer vortex array waveplate may gain spatially distributed chromatic dispersion, with wavelength dependent phase fronts for each vortex given by:

$$\Phi(x, y) = l_{mn} \cdot \left(\frac{\lambda}{\lambda_0}\right) \cdot \theta_{mn}(x, y)$$

where $\lambda_0$ is the design wavelength that corresponds to the topological charge $l_0$ and $\theta(x,y)$ is the azimuthal polar coordinate centered on each vortex in the array. FIG. 35 is an example graphic of light shining on a non-integer vortex array waveplate and an example resulting image in some embodiments.

Figure 30:
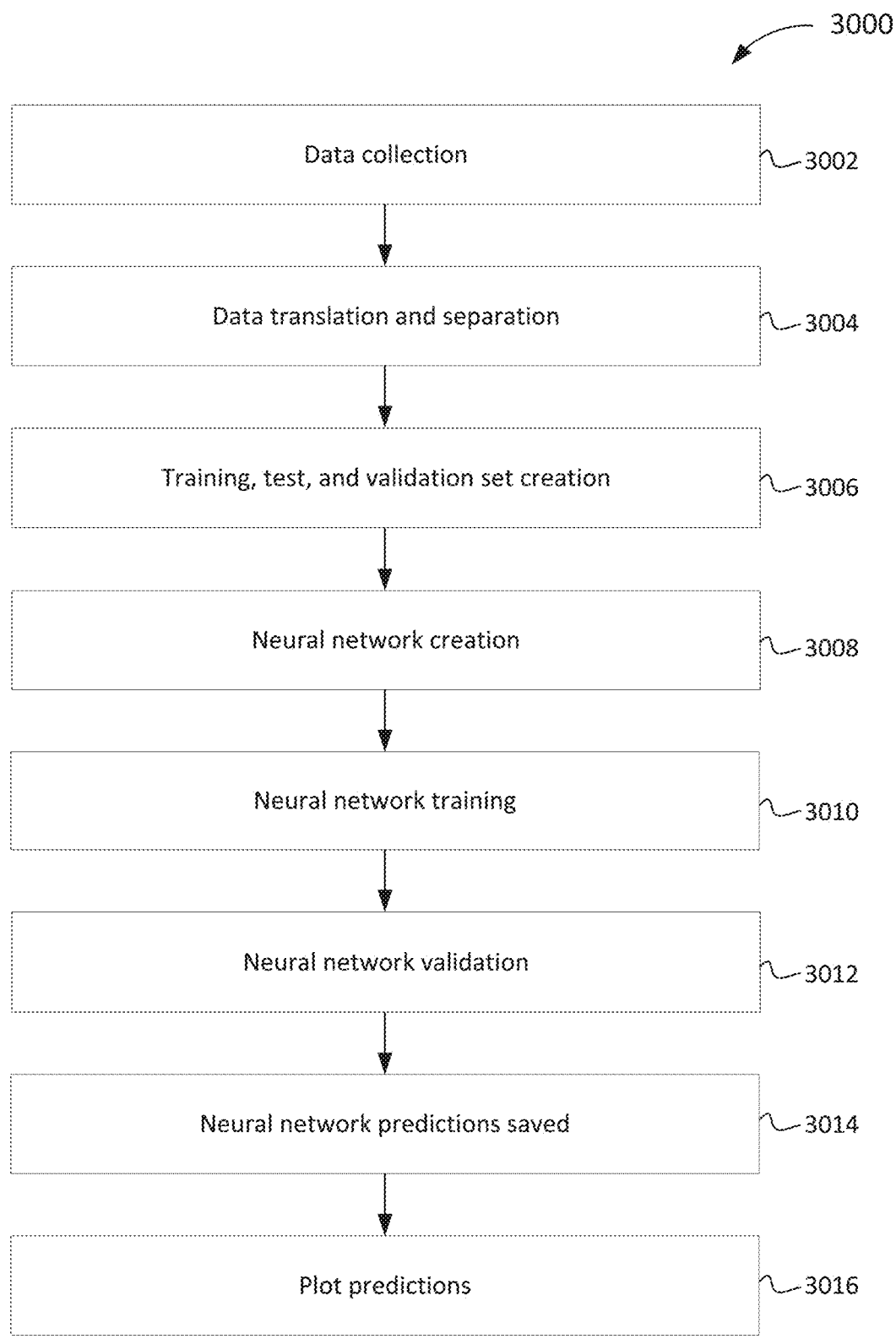
FIG. 30 is a flowchart for creating filtering for spectral reconstruction in some embodiments.

FIG. 30 is a flowchart for creating filtering for spectral reconstruction in some embodiments. As discussed herein, the speckle pattern may be measured as a function of spectrum and current. The measurement(s) may then be modeled to create a filter to improve accuracy of spectral measurements when passed through a sample (e.g., a biological sample) and the diffuser or speckle pattern. In various embodiments, a processor may receive simultaneous or near simultaneous measurements of current and wavelength as the light passes through the speckle pattern. The processor may then determine a variation of speckle pattern as a function of wavelength.

The speckle patterns generated after transmitting light through the diffuser or speckle pattern may be different for each wavelength, with the presence of inherent noise (e.g., caused by instruments and/or environmental factors). In various embodiments, neural networks, such as a deep neural network, may be used for classification. Through training, the DNN may learn to reject variations in the speckle patterns which do not correspond to wavelength.

In step 3002, a spectral reconstruction device performs data collection. A spectral reconstruction device may be any digital device. In one example, the spectral reconstruction device is a cloud-based system configured to collect information, translate/separate data, train/test/and validate set creation, utilize a neural network for predictions, and plot predictions. The spectral reconstruction device may provide plot predictions for any number of spectrometers. In some embodiments, the spectral reconstruction device is local. In various embodiments, different functions of the spectral reconstruction device may be performed locally while other functions may be performed in the cloud.

In various embodiments, the spectral reconstruction device communicates with a spectrometer (e.g., the spectrometer discussed in FIG. 25 and the data processing unit 2524 may be the spectral reconstruction device).

Data from a detector of the spectrometer may be stored in any number of ways. In one example, the spectral reconstruction device creates a Pandas DataFrame to store the data received from a laser diode controller (e.g., a controller that controls a light source of the spectrometer) and detector of the spectrometer. The spectral reconstruction device may include a resource manager to speak with the laser diode controller (e.g., Using PyVisa and SCPI commands from Thorlabs). Following this, the spectral reconstruction device may create variables to set parameters for the laser diode controller and detector of the spectrometer. This may include, for example, the IntegrationTime (e.g., 30 μs), NumberOfAverages (e.g., 9), Laser1 Temperature bounds and tolerance (e.g., 18° C.), and Laser1 Current bounds and tolerance (e.g., 28 mA-34.3 mA, 0.1 mA). From here, contact with the laser diode controller and detector of the spectrometer may be initiated, data may be gathered on the wavelengths of the detector, and the data passed through configuration parameters.

In some embodiments, the data collection is enclosed in a loop that starts at the lower bound of the current and iterates to the upper bounds. Temperature bounds may be provided to the controller and then read back to ensure correctness. The same may be done for the current. When both bounds are within their set tolerances, the spectrometer may capture spectral data. The array is then interpolated over the set wavelengths of the spectrometer. The current, temperature, spectral data, and wavelengths may be stored (e.g., saved to a new row of a Pandas DataFrame). Once the iterations are complete, the data is saved (e.g., DataFrame is then saved out to a CSV file) and the Laser Diode is turned off.

In step 3004, data is translated and separated. For example, the spectral data may be placed in its own DataFrame and split up into cells (e.g., into 2050 cells). The first and last cells may be deleted as they may contain no information. Individual cells may be processed to turn them from string objects into float objects for later use in arrays (e.g., NumPy arrays). The original DataFrame may be referenced again to extract the current data and stored in its own DataFrame. The current data and spectral data may be concatenated into one structure for use in the neural network. The combined DataFrame and spectral data DataFrame may be saved (e.g., into Pickle files) for later use.

In step 3006, the data set is created. For example, current data and spectral data may be loaded into a DataFrame. The first column that correlates to the current data may be translated to a Numpy Array. The same may be done for the spectral data to in its own Numpy Array. These arrays may be then passed into a function that splits the data into training and test sets. The test sets may then be split again into test sets and validation sets.

Figure 31:
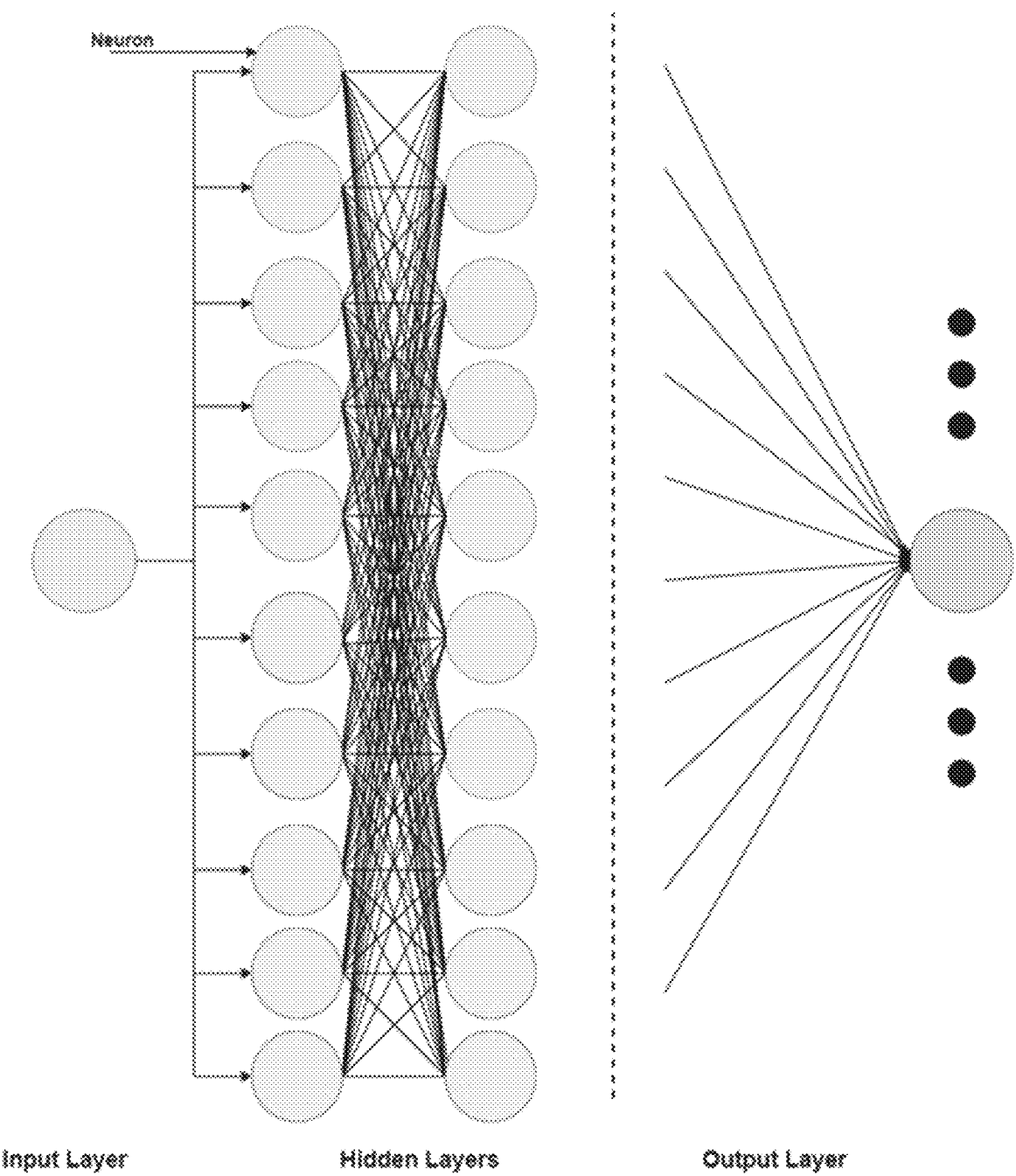
FIG. 31 depicts an example architecture of the neural network.

In step 3008, individual layers of the neural network are created. In some embodiments, the neural network consists of an input layer of one neuron that matches the dimension of the current data array. In some embodiments, there may be a number of fully connected dense layers (e.g., 9 fully connected dense layers) each with a number of neurons (e.g., 100 neurons) with the ReLu activation function. The output layer may be another dense layer but with a number of neurons (e.g., 2048 neurons) that correspond to the points (e.g., 2048 points) in the output spectral data. FIG. 31 depicts an example architecture of the neural network.

In some embodiments, to improve computation and structural efficiency, these layers may be added to a Tensorflow model. An Adam optimizer (e.g., with a learning rate of 0.01) may be created and added to a compilation of the model. The loss function used may be, for example, mean squared error with the accuracy model being tracked. The model may then fit on the training set (e.g., over 250 epochs with a batch size of 20).

In step 3010 many different wavelengths are repeated projected through the diversifier and scattering patterns detected to confirm and train the neural network. As discussed herein, spectral patterns of scattered light may be reproduceable for identifying wavelengths projected by the light source. Light at specific wavelengths may be projected for specific durations of time (e.g., some longer durations and other shorter durations), and the spectral information provided to the neural network for testing with known data and training.

In step 3012, the neural network results are validated against the validation set that was created earlier (e.g., against known wavelengths as well as the patterns that are expected based on the neural network).

In step 3014, predictions of the neural networks are saved and used to generate filtering information to allow for spectral reconstruction. Each different spectrometer may have different filtering information that has been tuned or configured based on noise inherent in that spectrometer's components, light sources, detectors, and/or light path. The filtering information may be stored in the cloud for each different spectrometer. In some embodiments, the filtering information associated with a particular spectrometer may be stored at a digital device proximate to the spectrometer or by the spectrometer (assuming the spectrometer has a processor and memory for utilizing the filtering information).

In step 3016, predictions are plotted and noise reduced or eliminated by using the filtering information during testing of user's samples. The predictions may then be saved as a NumPy array for further analysis and graphing.

Training may be validated against the validation set that was created earlier. Once scattering patterns are recognized and associated with current and wavelength (e.g., using the neural network discussed herein), the associations may be tested with known wavelengths and expected scattering patterns in step.

Once training is complete, the test set may be used to test the model's completed predictions.

Figure 32:
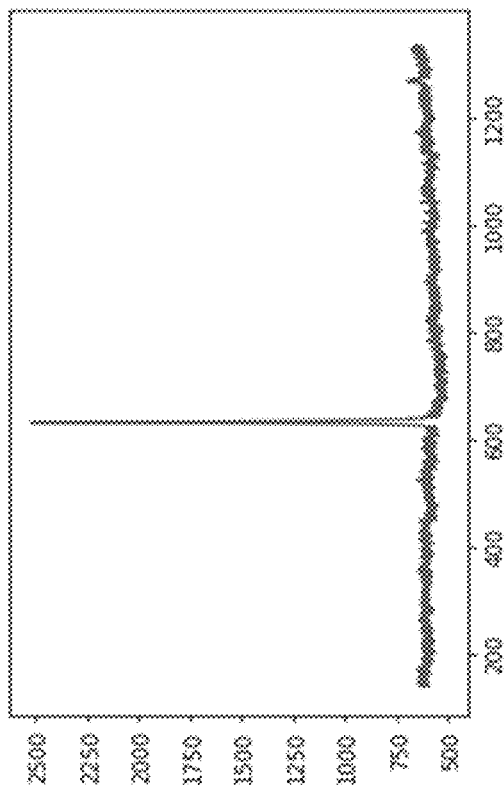
FIG. 32 is an example spectra taken from the data collected from the spectrometer.

FIG. 32 is an example spectra taken from the data collected from the spectrometer. In this example, there was a low current input which is why the 635 nm peak only reaches 2500 counts.

Figure 33:
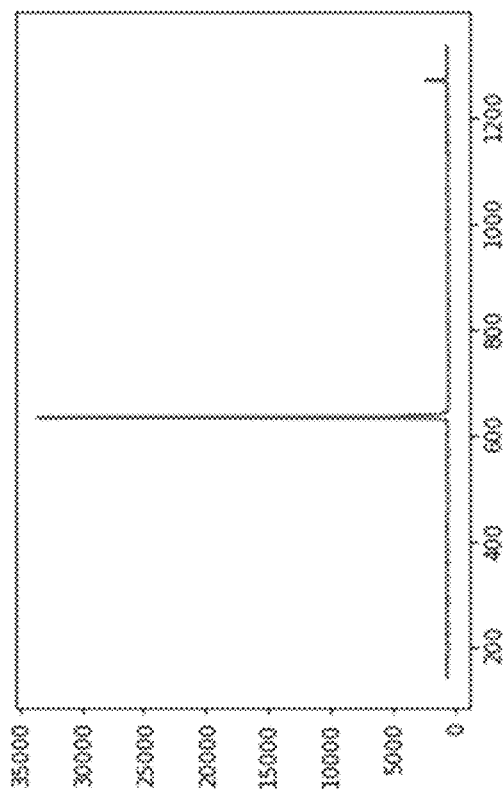
FIG. 33 is a spectra that was reconstructed by the neural network.

FIG. 33 is a spectra that was reconstructed by the neural network. While the spectra reaches a much higher peak power, the signal-to-noise ratio is about 10 times greater than the initial data that it was given. It will be appreciated that further refinements may further improve the signal-to-noise ratio.

Once filtering information is established for a spectrometer, the external spectrometer and/or external light sources may be removed.

Any number of spectrometers may be utilized to assess spectral patterns associated with a pathogen (e.g., COVID 19). In various embodiments, as discussed herein, the spectrometer(s) and related filtering information may be used to eliminate noise. Vortexes may further be used to identify signals (e.g., spectral scattering caused by the pathogen) that may be otherwise too faint to detect (e.g., because the pathogen being testing is very small). The signature of thumbprint of the spectral signature may be detected and trained such that the pathogen may be confidently and accurately detected in future samples.

Steps for generating a pathogen signature, may be similar to that discussed regarding FIG. 15. Using a spectrometer with a diversifier (e.g., speckle pattern, diffuser, vortex plasmonic array, and/or the like) as well as the filtering information to eliminate/reduce noise, samples containing the pathogen may be repeated tested and spectral intensities detected. Any number of spectrometers may be used (e.g., each with their own diversifier and filtering information). The filtering information may be used to reconstruct the spectral signal of the wavelengths of light provided by the light source so to isolate those signals caused by the presence of the pathogen in the sample. By using the system described with the diversifier and filtering information, signal qualities related to the pathogen may be more apparent and signature acquired may be more accurately defined and detected.

In various embodiments, a statistical process and/or machine learning process may be utilized to identify patterns of spectral scattering/absorption caused by the presence of a known pathogen in a sample. Concentration of pathogen and duration of testing may be controlled to assist in pattern recognition for pathogen signature identification. In various embodiments, a CNN (e.g., DNN) may be trained to identify and recognize patterns related to pathogen presence in the sample based on repeated testing of known concentrations of pathogens in a sample, known wavelengths, and the filtering information.

In various embodiments, a plurality of spectrometers (each with their own diversifiers) may test any number of samples with a known pathogen. Results of the tests may be provided to a central system on a network (e.g., in the cloud) which may then utilize results (and/or filtering information associated with each spectrogram) for pathogen signature detection. The centralized system may be utilize to leverage decentralized testing of any number of pathogens over any number of remote spectrometers. By centralizing the system on a network, the system may be able to detect patterns, define signatures, improve signatures, and provide consistent pathogen results to any number of remote operators and/or patients.

It will be appreciated that the centralized system may allow for results of tests of samples to be confidentially handled. For example, results and testing information may be securely (e.g., via encryption) stored and communication handled to ensure effective, confidential processes are conducted for information security and privacy in accordance with state, national, and international standards. This may also ensure processes are in place to communicate results to those who have a right to the information.

Once signatures are created, the centralized system may validate and test pathogen signatures against samples of known infection to confirm accuracy and robustness. It will be appreciated that the centralized system may test new samples with the signatures for presence of infection of the particular pathogen and then utilize information of the sample, results, and any other information to update signatures or create new signatures as pathogens evolve or separate into new strains.

Further, once signatures are created, the centralized system may provide pathogen signatures to other centralized systems on a network and/or spectrometers for use in pathogen detection in new samples. Alternately, the centralized system may maintain pathogen signatures and compare sample results from any number of spectrometers to the signatures for centralized pathogen detection. In various embodiments, the centralized system may utilize probabilistic methods to determine a likelihood of match between the results from the spectrometers (e.g., the spectrometers including diversifiers and the results being adjusted with the filtering information) and the pathogen signature. In some embodiments, the centralized system may utilize a CNN, DNN, boosted decision trees, or the like to determine a likelihood of match between the results from the spectrometers and the pathogen signature.

In some embodiments, the centralized system may test results from a spectrometer against any number of pathogen signatures. In one example, the centralized system may receive results from a spectrometer with a diversifier, and may compare or analyze the results against a set of two or more pathogen signatures to detect the presence of one or more pathogens in the sample.

In various embodiments, a pathogen signature may be created for a class or group of pathogens (e.g., five different variants of COVID 19). If a sample is determined to have pathogens based on a comparison or analysis using the pathogen signature (a "group pathogen signature"), then indications of infection may be provided to the user or operator. In some embodiments, after a sample is determined to have pathogens, further pathogen signatures may be used to identify which pathogen(s) of the class or group of pathogens is present in the sample.

As discussed herein, measurements conducted by a spectrometer with a diversifier may be performed over any duration of time (e.g., while the light source is projecting light over a period of time). In some embodiments, the light source may direct light to a portion of the cuvette containing the sample and/or to a particular portion of the diversifier. In some embodiments, the detector or lenses may be configured to analyze only a portion of the light being transmitted through the diversifier for scattering pattern detection, testing, validation, and/or biological sample spectral detection.

Figure 36:
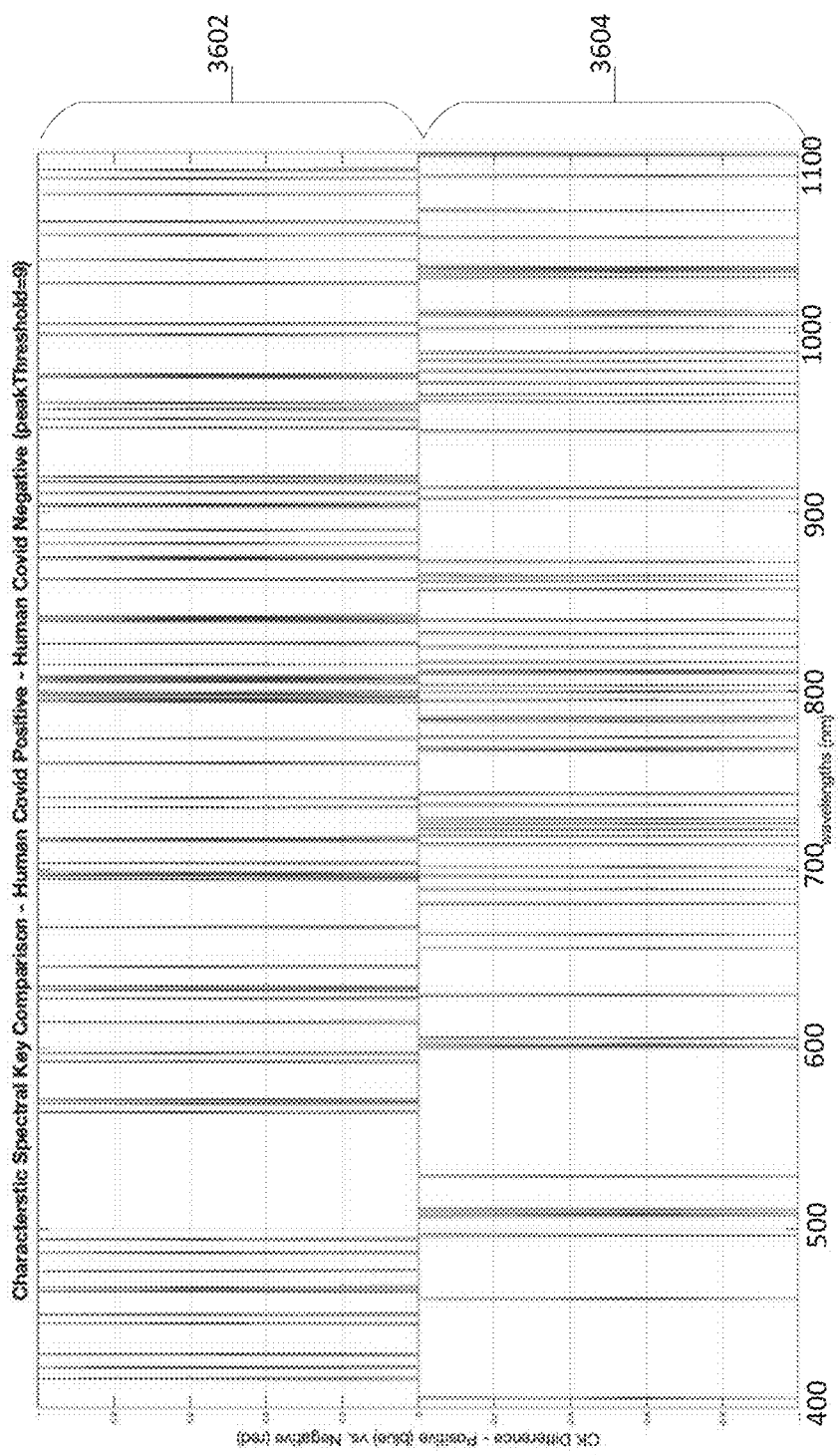
FIG. 36 depicts an example human positive spectral signature for COVID infection and an example human negative spectral signature for COVID infection.

FIG. 36 depicts an example human positive spectral signature 3602 for COVID infection and an example human negative spectral signature 3604 for COVID infection. In various embodiments, when measurements are made of a patient's sample, they may be compared to the human positive spectral signature 3602 and/or the human negative spectral signature 3604 to determine if the sample is positive for infection, negative for infection, and/or likely.

FIGS. 39-59 are comparisons of a positive COVID spectral signature and other pathogens. It will be appreciated that systems and methods described herein may detect many other pathogens as shown herein. The comparison of the COVID spectral signature to each different pathogen signature further shows that systems and methods described herein may be configured to detect many different pathogens simultaneously. For example, a user may provide a swab sample and the health screening system (e.g., a spectrometer as described herein and the health screening system in the cloud) may detect any number of different pathogens (e.g., without being reconfigured to changed for each pathogen).

Figure 39:
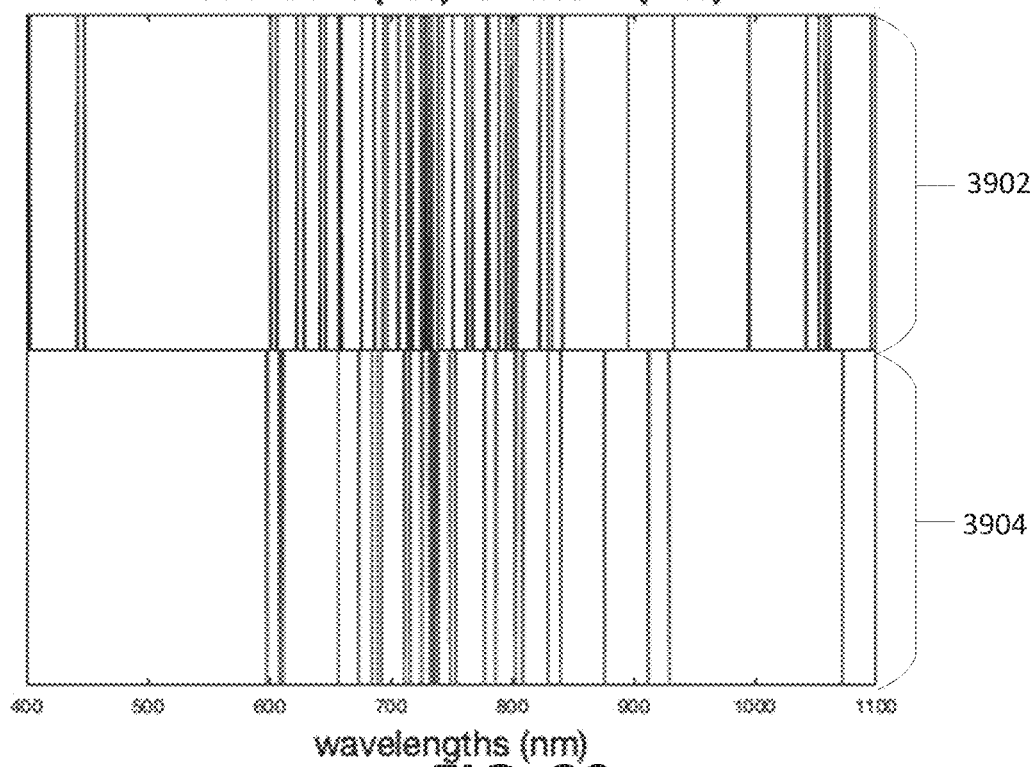
FIG. 39 is an example comparison of wavelength signature for natrol COVID and wavelength signature for human coronavirus 229E, strain 229E.
Figure 40:
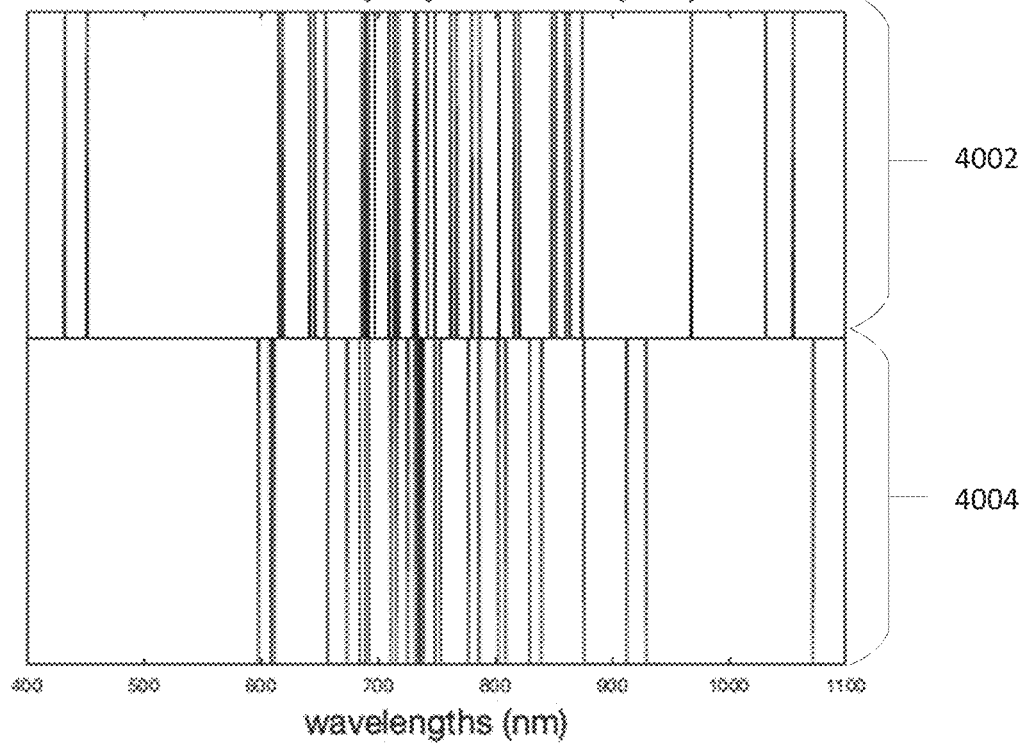
FIG. 40 is an example comparison of wavelength signature for natrol COVID and wavelength signature for beta-coronavirus 1, strain OC43.
Figure 41:
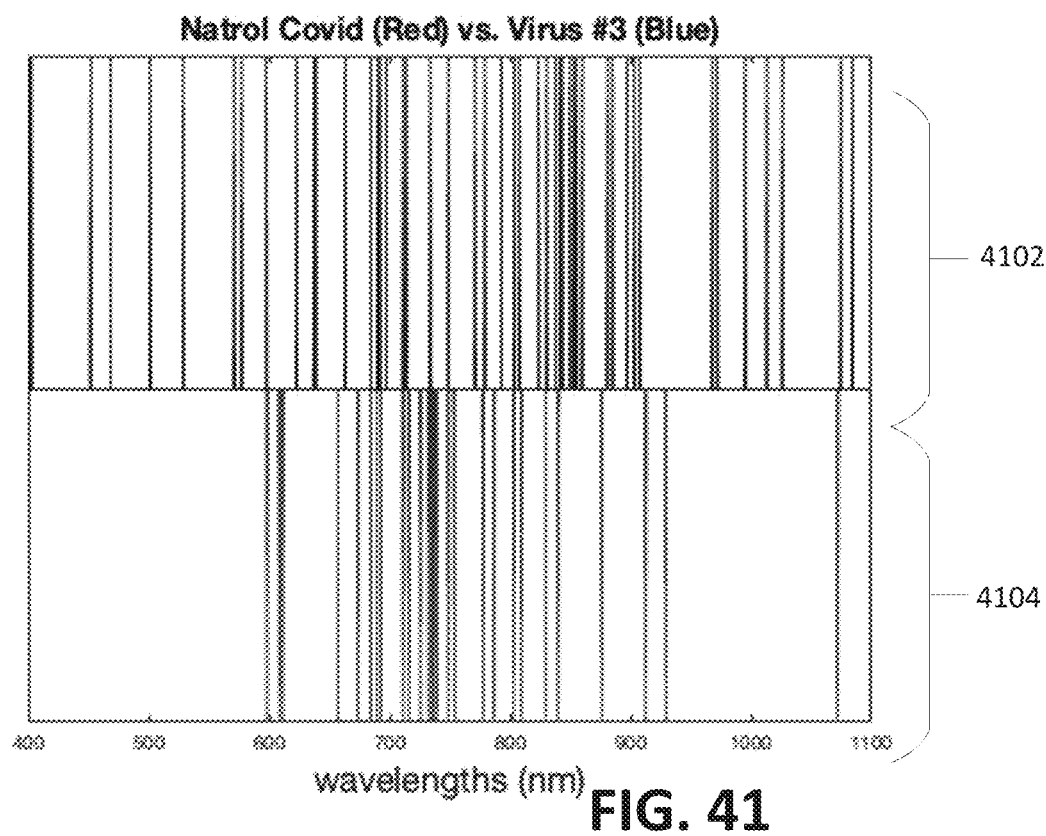
FIG. 41 is an example comparison of wavelength signature for natrol COVID and wavelength signature for Human adenovirus 5, Strain Adenoid 75.
Figure 42:
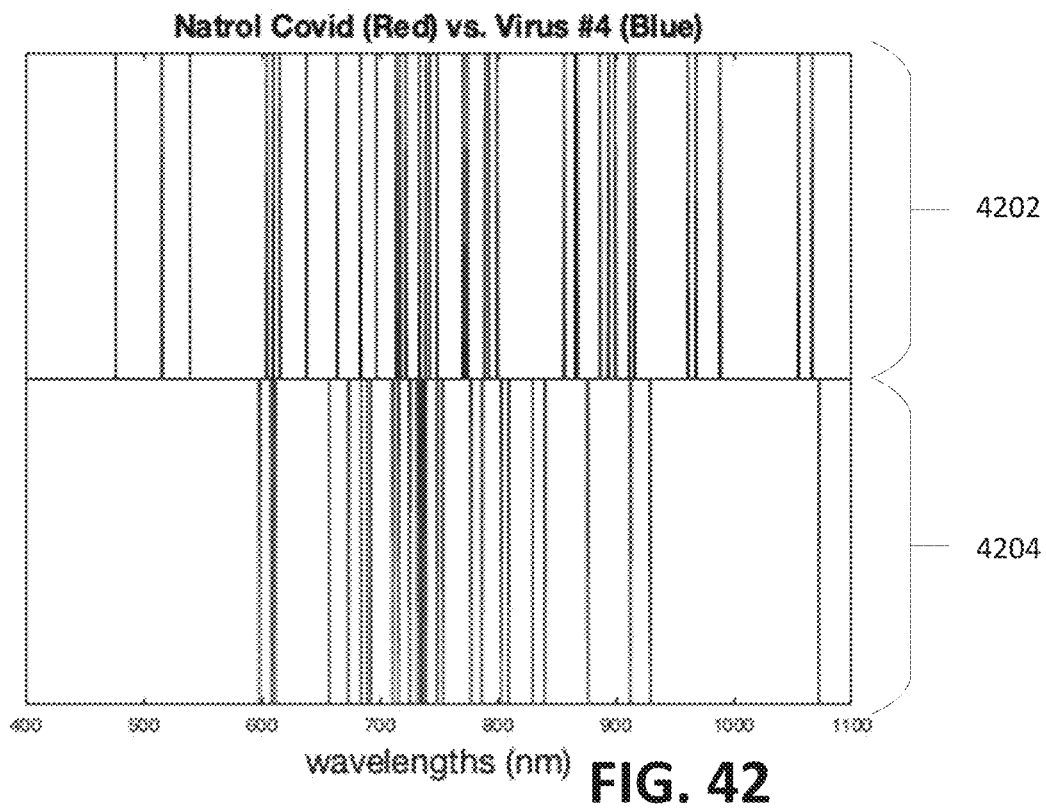
FIG. 42 is an example comparison of wavelength signature for natrol COVID and wavelength signature for Influenza A virus (H3N2), Strain A/Aichi/2/68.
Figure 43:
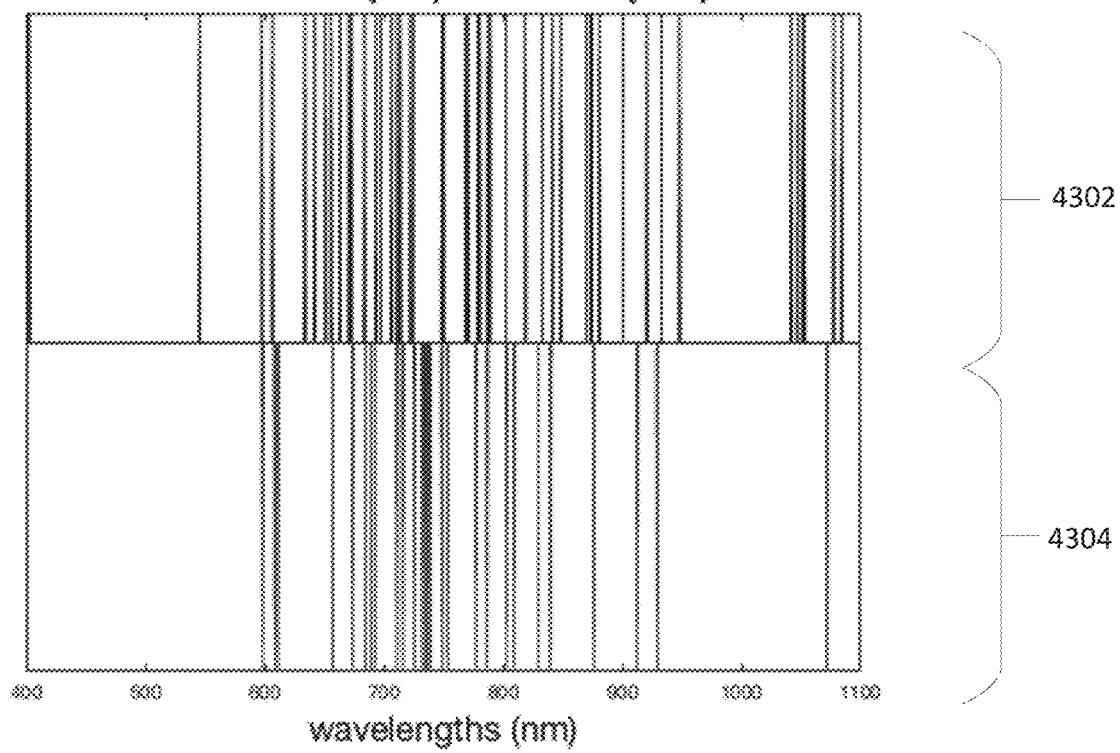
FIG. 43 is an example comparison of wavelength signature for natrol COVID and wavelength signature for Human parainfluenzavirus 3 (HPIV-3), Strain C and/or any number of patrons may be tested for infection. Each patron may be tested with a health screening device 104.
Figure 44:
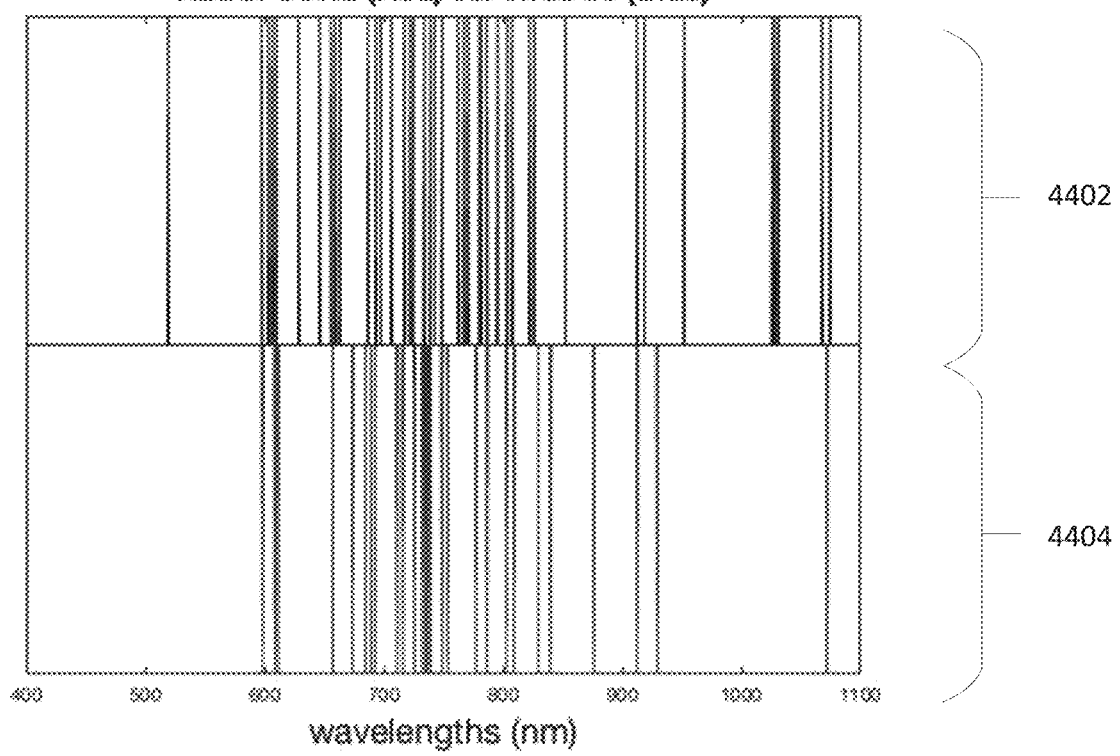
Figure 45:
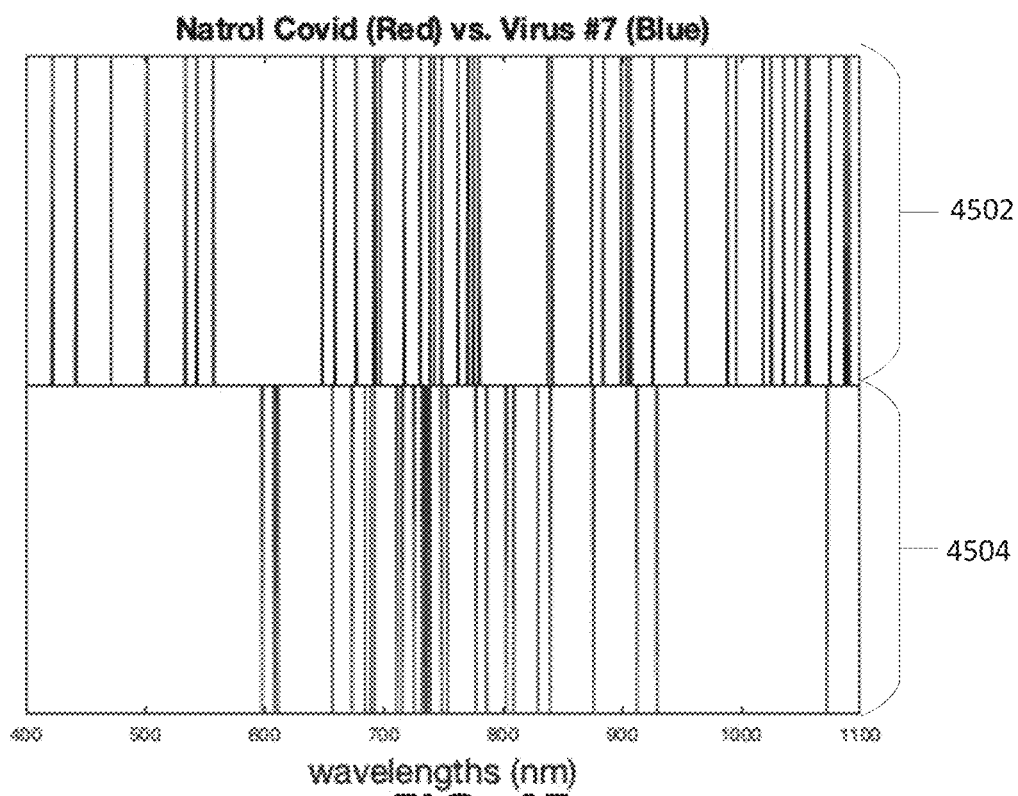
Figure 46:
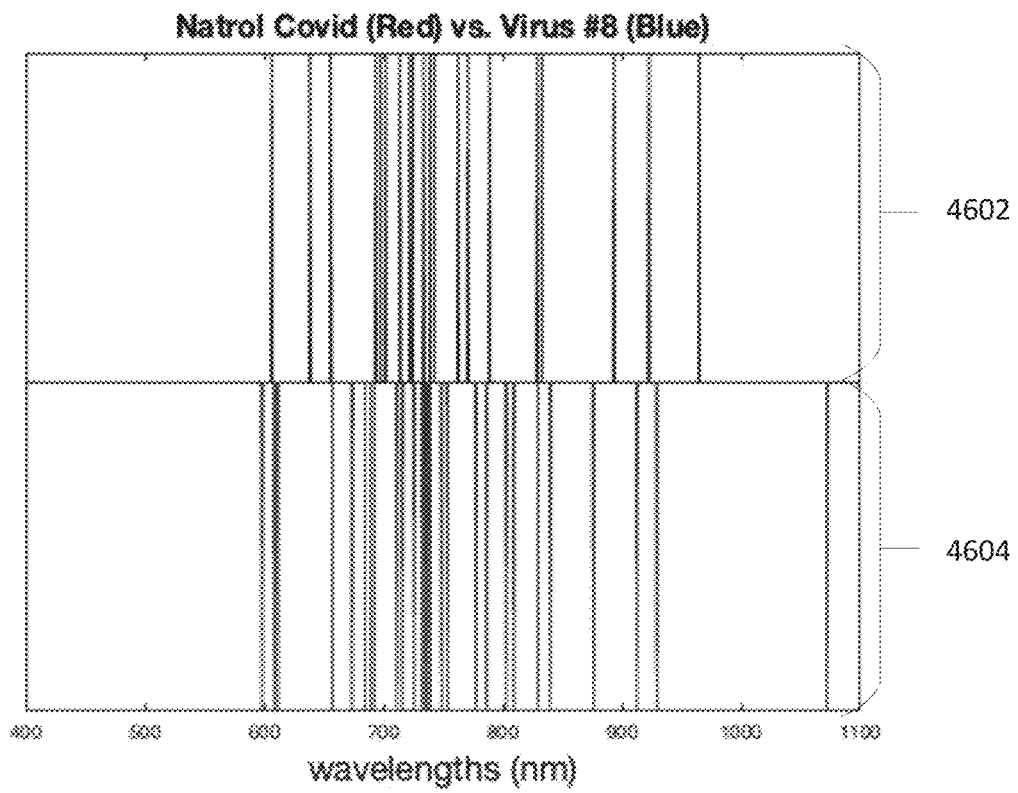
Figure 47:
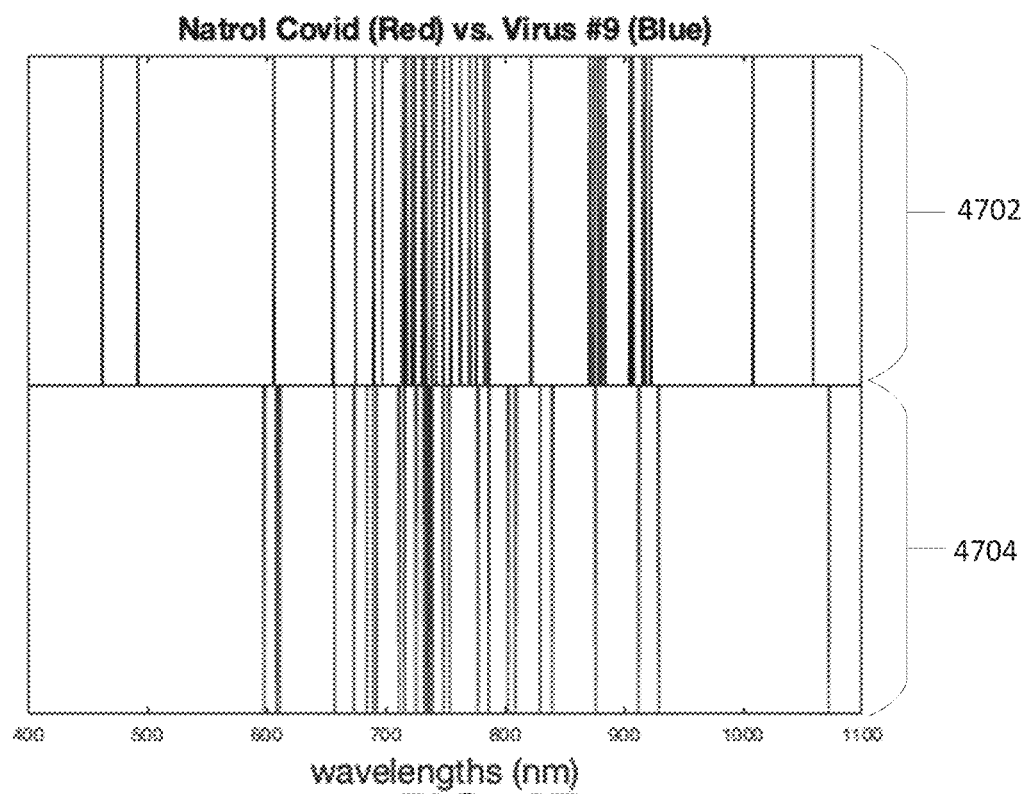
Figure 48:
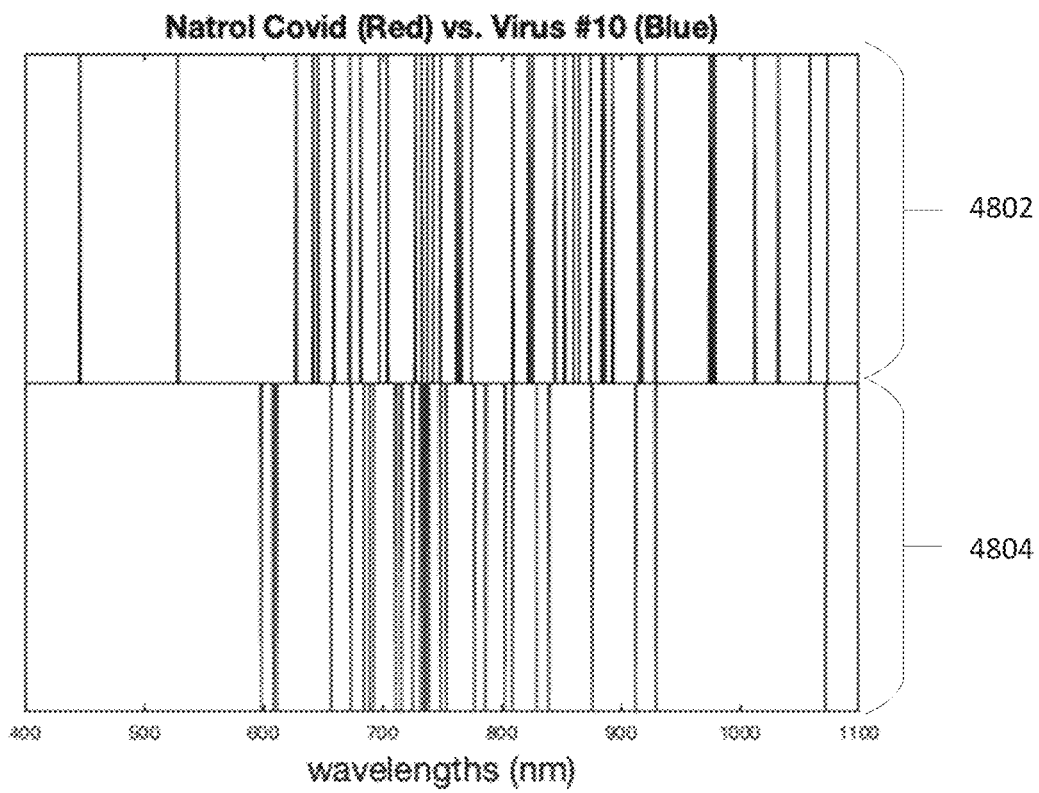
Figure 49:
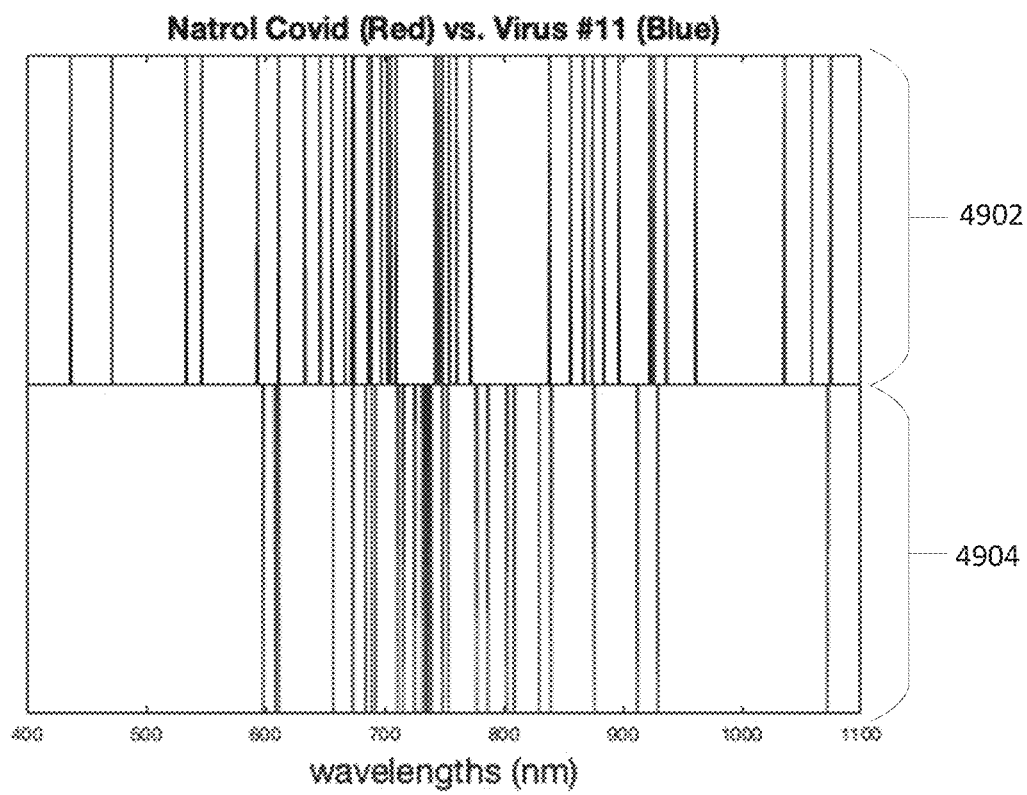
Figure 50:
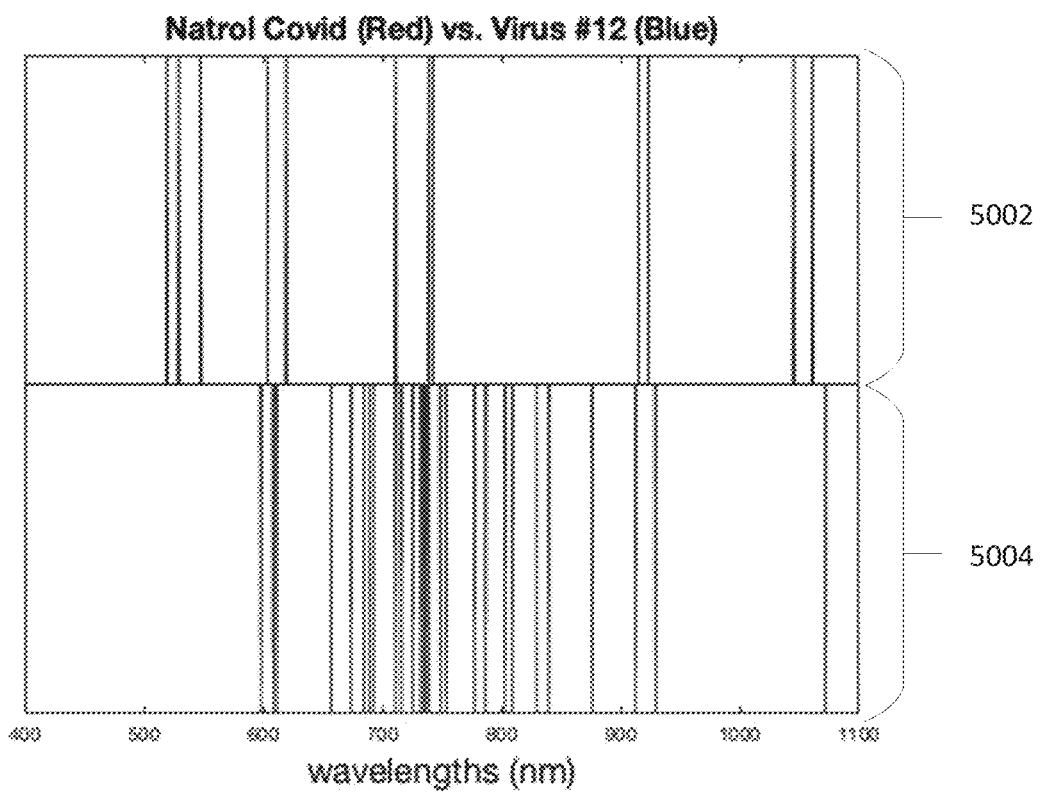
Figure 51:
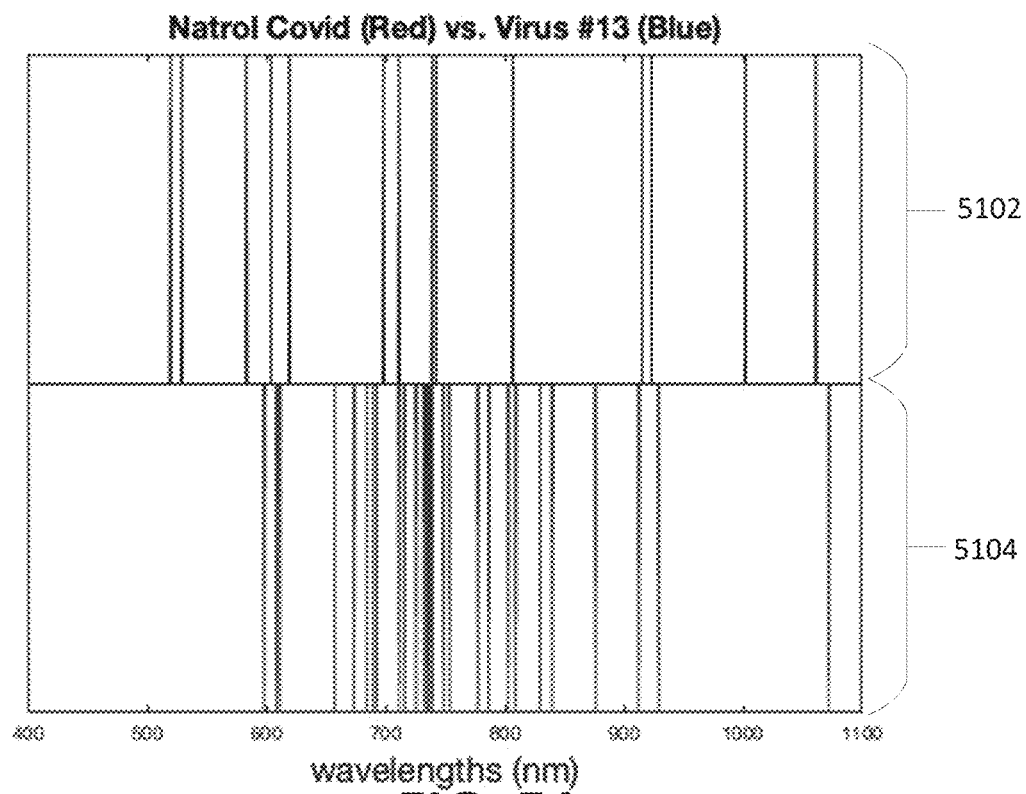
Figure 52:
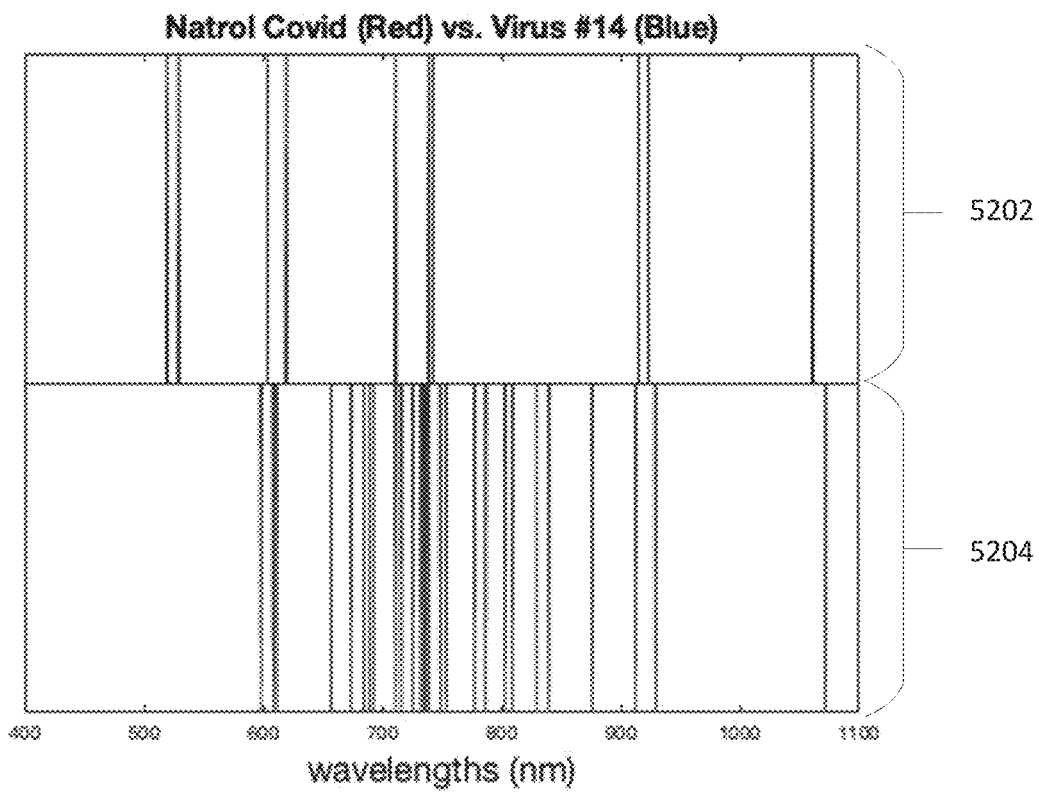
Figure 53:
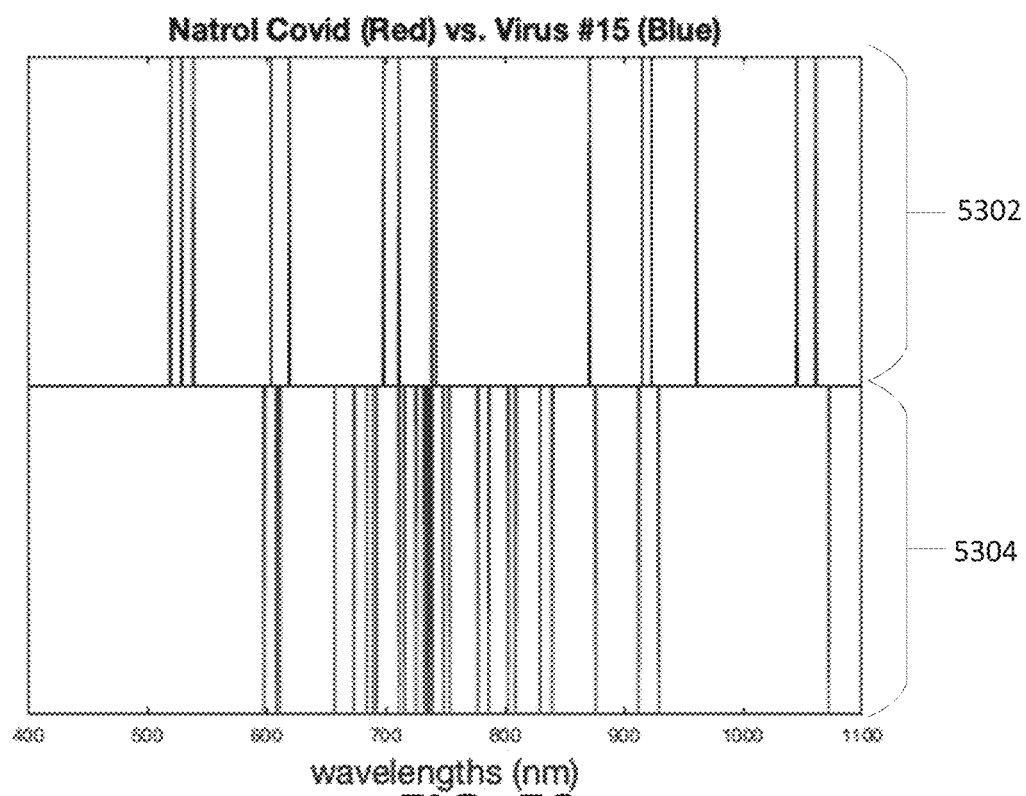
Figure 54:
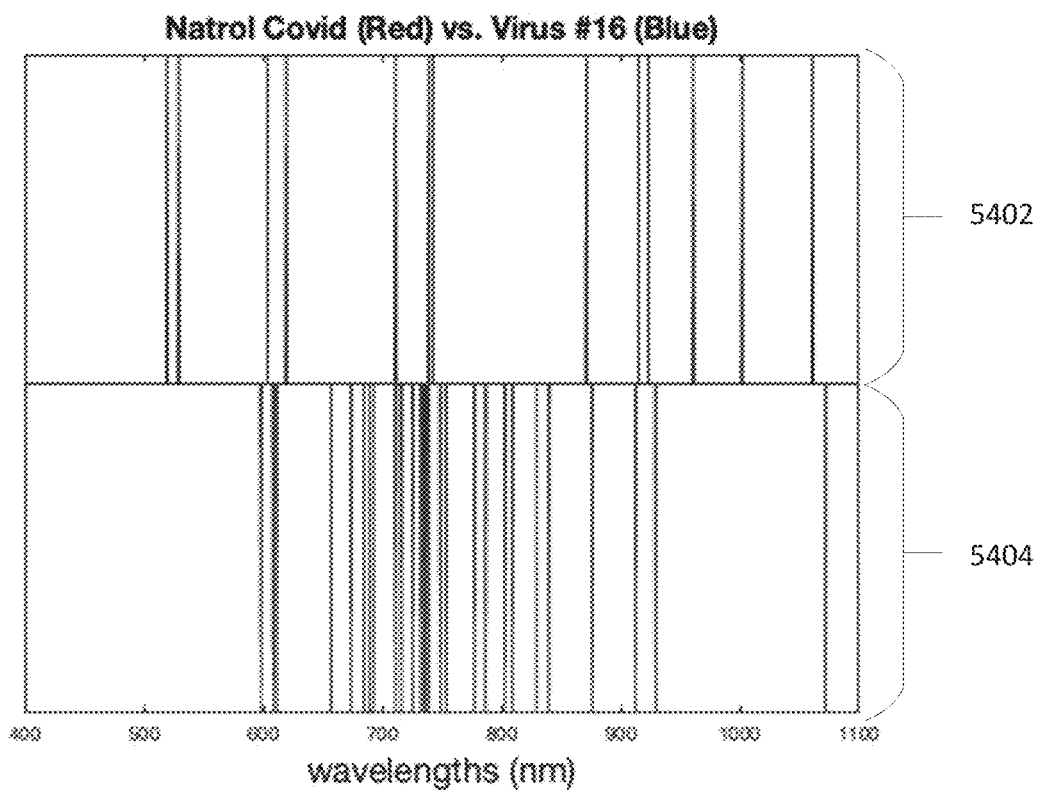
Figure 55:
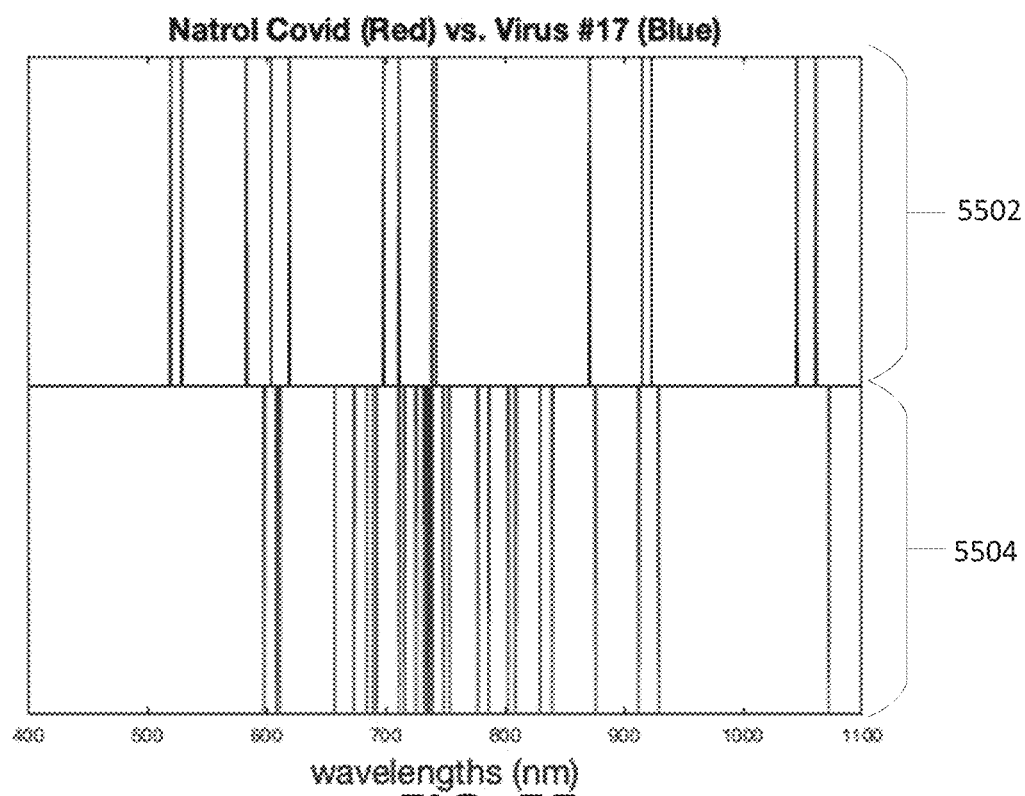
Figure 56:
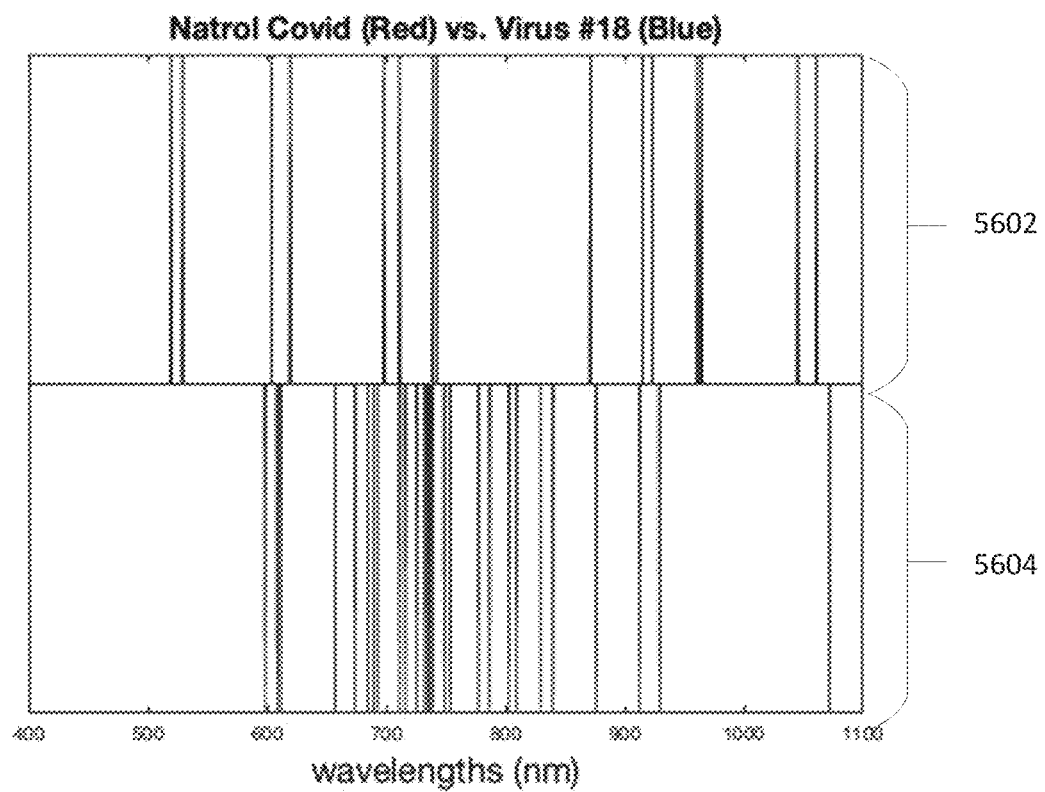
Figure 57:
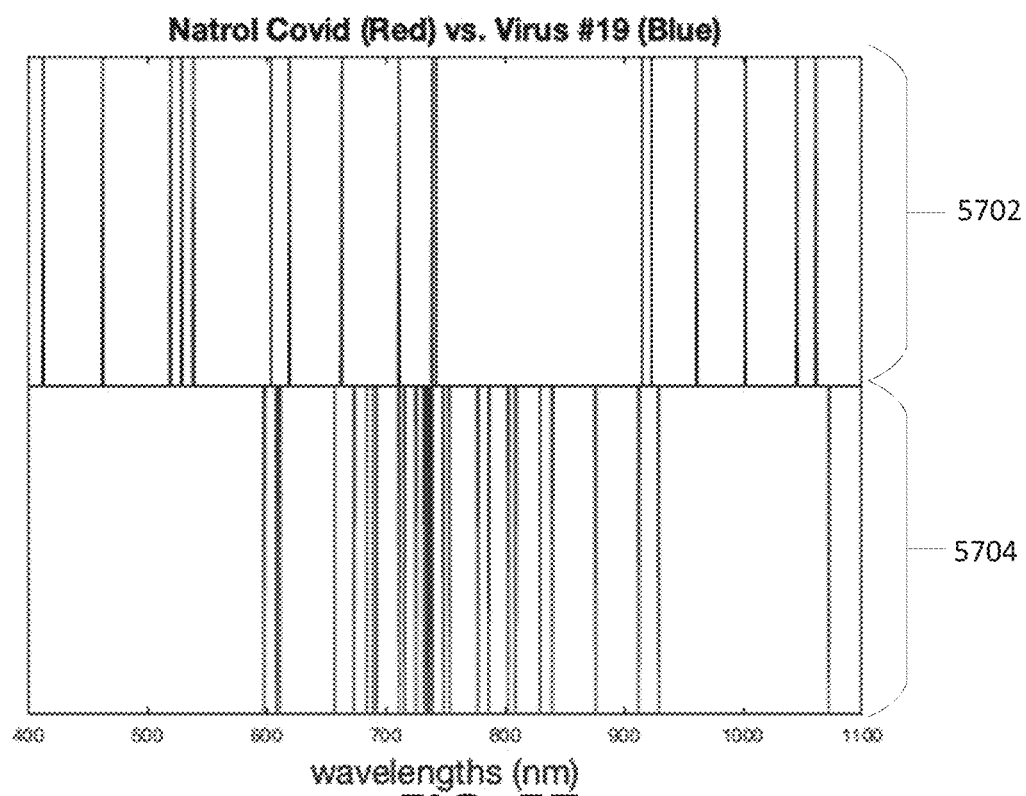
Figure 58:
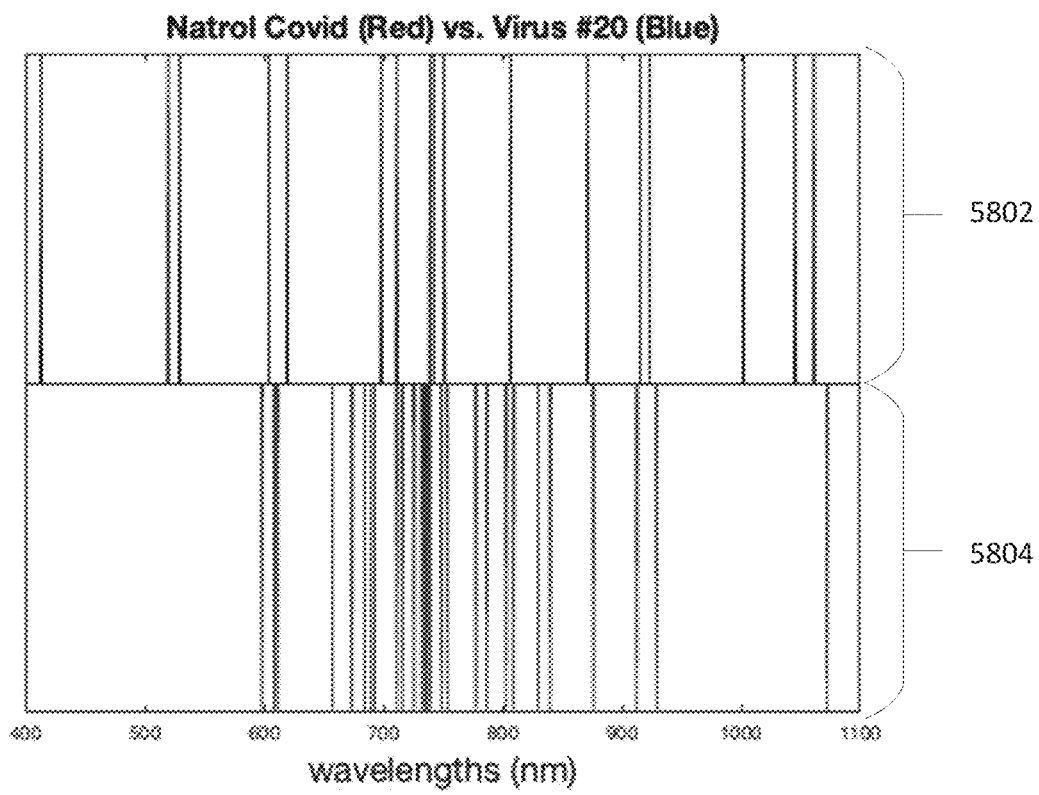
Figure 59:
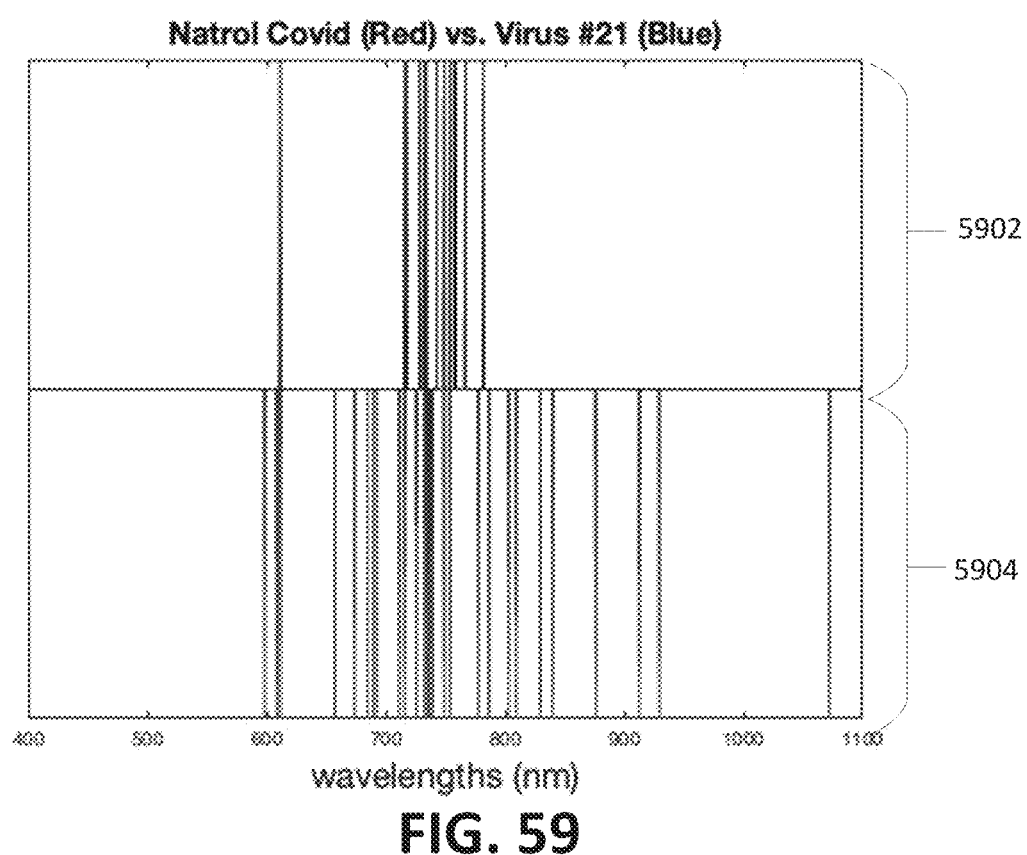

FIG. 39 is an example comparison of wavelength signature 3902 for natrol COVID and wavelength signature 3902 for human coronavirus 229E, strain 229E.

FIG. 40 is an example comparison of wavelength signature 4004 for natrol COVID and wavelength signature 4002 for betacoronavirus 1, strain OC43.

FIG. 41 is an example comparison of wavelength signature 4104 for natrol COVID and wavelength signature 4102 for Human adenovirus 5, Strain Adenoid 75.

FIG. 42 is an example comparison of wavelength signature 4204 for natrol COVID and wavelength signature 4202 for Influenza A virus (H3N2), Strain A/Aichi/2/68.

FIG. 43 is an example comparison of wavelength signature 4304 for natrol COVID and wavelength signature 4302 for Human parainfluenzavirus 3 (HPIV-3), Strain C 243.

FIG. 44 is an example comparison of wavelength signature 4404 for natrol COVID and wavelength signature 4402 for Influenza A virus (H1N1), Strain A/Virginia/ATCC1/2009.

FIG. 45 is an example comparison of wavelength signature 4504 for natrol COVID and wavelength signature 4502 for Influenza B virus, Strain B/Florida/78/2015.

FIG. 46 is an example comparison of wavelength signature 4604 for natrol COVID and wavelength signature 4602 for Human enterovirus 71, Strain H.

FIG. 47 is an example comparison of wavelength signature 4704 for natrol COVID and wavelength signature 4702 for Human respiratory syncytial virus, Strain A2.

FIG. 48 is an example comparison of wavelength signature 4804 for natrol COVID and wavelength signature 4802 for Human rhinovirus 17, Strain 33342.

FIG. 49 is an example comparison of wavelength signature 4904 for natrol COVID and wavelength signature 4902 for *Chlamydophila pneumoniae*, Strain TW-183.

FIG. 50 is an example comparison of wavelength signature 5004 for natrol COVID and wavelength signature 5002 for *Haemophilus influenzae.*

FIG. 51 is an example comparison of wavelength signature 5104 for natrol COVID and wavelength signature 5102 for *Legionella pneumophila*, subsp. *pneumophila.*

FIG. 52 is an example comparison of wavelength signature 5204 for natrol COVID and wavelength signature 5202 for *Streptococcus pneumoniae*, Strain NCTC 7465.

FIG. 53 is an example comparison of wavelength signature 5304 for natrol COVID and wavelength signature 5302 for *Streptococcus pyogenes*, Strain Bruno [CIP 104226].

FIG. 54 is an example comparison of wavelength signature 5404 for natrol COVID and wavelength signature 5402 for *Bordetella pertussis*, Strain F.

FIG. 55 is an example comparison of wavelength signature 5504 for natrol COVID and wavelength signature 5502 for *Mycoplasma pneumoniae*, FH Strain of Eaton Agent.

FIG. 56 is an example comparison of wavelength signature 5604 for natrol COVID and wavelength signature 5602 for *Candida albicans*, Strain NIH 3172.

FIG. 57 is an example comparison of wavelength signature 5704 for natrol COVID and wavelength signature 5702 for *Pseudomonas aeruginosa.*

FIG. 58 is an example comparison of wavelength signature 5804 for natrol COVID and wavelength signature 5802 for *Staphylococcus epidermidis*, Strain PCI1200.

FIG. 59 is an example comparison of wavelength signature 5804 for natrol COVID and wavelength signature 5802 for *Streptococcus salivarius*, subsp. *salivarius.*

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

It may be apparent to those skilled in the art that various modifications may be made and other embodiments may be used without departing from the broader scope of the discussion herein. Therefore, these and other variations upon the example embodiments are intended to be covered by the disclosure herein.

The invention claimed is:

1. A system comprising:

at least one light source configured to generate a light at specific wavelengths and project the light over an optical path;

a sample device, the sample device configured to receive a sample obtained from a person, the sample device being transparent and being at least partially within the optical path;

a diversifier including occlusions for scattering coherent light received from the light source along the optical path;

a first detector configured to receive the light over the optical path and from at least a portion of the diversifier, the detector configured to detect spectral intensities of the light; and a second detector configured to receive at least a portion of the light form the optical path before the light passes through the diversifier, the second detector configured to detect spectral intensities of the light.

2. The system of claim 1, further comprising a processor configured to compare results of spectral detection from the first detector and results of spectral detection of the second detector in view of the specific wavelengths present in the light to recognize spectral patterns caused by scattering from the diversifier.

3. The system of claim 2, wherein the processor generates filtering information to reconstruct spectral information based on the comparison, the filtering information including spectral intensities related to the light from the light source and not including at least some noise added during projection of the light along the light path.

4. The system of claim 3, wherein the system is configured to compare results comprises performing pattern recognition using a deep neural network.

5. The system of claim 3, wherein the processor is remote from the first detector and the second detector.

6. The system of claim 5, wherein the processor is further configured to compare results of spectral detection from a third detector and results of spectral detection of a fourth detector in view of specific wavelengths present in the other light projected by an other light source along an other light path to recognize spectral patterns caused by scattering from an other diversifier, the third detector configured to receive the other light after being projected through at least a part of an other diversifier, the fourth detector configured to receive the other light before being projected through the other diversifier.

7. The system of claim 6, wherein the processor is configured to generate other filtering information to reconstruct spectral information based on comparison of the results of spectral detection from a third detector and results of spectral detection of a fourth detector, the other spectral information including spectral intensities related to the other light from the other light source and not including at least some noise added during projection of the other light along the other light path.

8. The system of claim 3, wherein the processor is further configured to utilize the filtering information for subsequent spectral detection from the first detector to remove noise when a biological sample is contained within the sample device.

9. The system of claim 8, wherein the processor is further configured to detect pathogen signatures by recognizing spectral scattering and absorption caused by known pathogens in a plurality of samples using the first detector and the filtering information to reduce noise and improve spectral detection related to pathogen detection.

10. A method comprising:
projecting a light over an optical path by at least one light source at light at specific wavelengths and project the light over an optical path;
receiving, by a sample device, the light generated by the at least one light source, the sample device capable of receiving a sample obtained from a person, the sample device being transparent and being at least partially within the optical path;
receiving, by a diversifier, the light after passing through the sample device;
scattering at least some of the light by the diversifier, coherent light of the light being scattered by occlusions of the diversifier;
receiving light along the light path by a first detector after light has scattered by the diversifier;
detecting, by the first detector, spectral intensities of the light after having passed through the diversifier;
generating first measurements of the spectral intensities detected by the first detector;
receiving light along the light path by a second detector before light has scattered by the diversifier;
detecting, by the second detector, spectral intensities of the light; and
generating second measurements of the spectral intensities detected by the second detector.

11. The method of claim 10, further comprising comparing the first measurements and the second measurements in view of the specific wavelengths present in the light to recognize spectral patterns caused by scattering from the diversifier.

12. The method of claim 11, further comprising generating, by a processor, filtering information to reconstruct spectral information based on the comparison, the filtering information including spectral intensities related to the light from the light source and not including at least some noise added during projection of the light along the light path.

13. The method of claim 12, wherein comparing the first measurements and the second measurements comprises performing pattern recognition using a deep neural network.

14. The method of claim 12, wherein the processor is remote from the first detector and the second detector.

15. The method of claim 14, further comprising comparing, by the processor, third measurements of an other light by a third detector and four measurements of the light by a fourth detector in view of specific wavelengths present in the other light projected by an other light source along an other light path to recognize spectral patterns caused by scattering from an other diversifier, the third detector configured to receive the other light after being projected through at least a part of an other diversifier, the fourth detector configured to receive the other light before being projected through the other diversifier.

16. The method of claim 15, further comprising generating, by the processor, other filtering information to reconstruct spectral information based on comparison of the third measurements of spectral detection from the third detector and fourth measurements of spectral detection from the fourth detector, the other spectral information including spectral intensities related to the other light from the other light source and not including at least some noise added during projection of the other light along the other light path.

17. The method of claim 12, further comprising, utilizing, by the processor, the filtering information for subsequent spectral detection from the first detector to remove noise when a biological sample is contained within the sample device.

18. The method of claim 17, further comprising detecting pathogen signatures by recognizing spectral scattering and absorption caused by known pathogens in a plurality of samples using the first detector and the filtering information to reduce noise and improve spectral detection related to pathogen detection.

* * * * *